United States Patent
Charrier et al.

(10) Patent No.: US 8,969,360 B2
(45) Date of Patent: Mar. 3, 2015

(54) COMPOUNDS USEFUL AS INHIBITORS OF ATR KINASE

(71) Applicant: Vertex Pharmaceuticals Incorporated, Cambridge, MA (US)

(72) Inventors: Jean-Damien Charrier, Wantage (GB); Chris Davis, Salisbury (GB); Steven Durrant, Abingdon (GB); Damien Fraysse, Abingdon (GB); Juan-Miguel Jimenez, Abingdon (GB); David Kay, Purton (GB); Ronald Knegtel, Abingdon (GB); Michael O'Donnell, Abingdon (GB); Francoise Pierard, Abingdon (GB); Joanne Pinder, Abingdon (GB); Pierre-Henri Storck, Abingdon (GB); Heather Twin, Wantage (GB)

(73) Assignee: Vertex Pharmaceuticals Incorporated, Boston, MA (US)

(*) Notice: Subject to any disclaimer, the term of this patent is extended or adjusted under 35 U.S.C. 154(b) by 0 days.

(21) Appl. No.: 14/098,655

(22) Filed: Dec. 6, 2013

(65) Prior Publication Data

US 2014/0275021 A1    Sep. 18, 2014

Related U.S. Application Data

(60) Provisional application No. 61/788,644, filed on Mar. 15, 2013.

(51) Int. Cl.
| | |
|---|---|
| C07D 487/04 | (2006.01) |
| A61K 31/505 | (2006.01) |
| C07D 491/107 | (2006.01) |
| A61K 31/437 | (2006.01) |

(52) U.S. Cl.
CPC .......... *C07D 491/107* (2013.01); *C07D 487/04* (2013.01); *A61K 31/437* (2013.01)
USPC ...................... 514/259.31; 544/281

(58) Field of Classification Search
USPC ...................... 544/281; 514/259.31
See application file for complete search history.

(56) References Cited

U.S. PATENT DOCUMENTS

| | | | |
|---|---|---|---|
| 6,060,478 | A | 5/2000 | Gilligan et al. |
| 6,191,131 | B1 | 2/2001 | He et al. |
| 6,235,741 | B1 | 5/2001 | Bilodeau et al. |
| 7,528,138 | B2 | 5/2009 | Knegtel et al. |
| 7,550,470 | B2 | 6/2009 | Fraley et al. |
| 2002/0041880 | A1 | 4/2002 | DeFeo-Jones et al. |
| 2006/0156482 | A1 | 7/2006 | Lim et al. |
| 2009/0318436 | A1 | 12/2009 | Albrecht et al. |
| 2012/0046295 | A1 | 2/2012 | Charrier et al. |
| 2013/0017273 | A1 | 1/2013 | Everitt et al. |
| 2013/0018035 | A1 | 1/2013 | MacCormick et al. |
| 2013/0034616 | A1 | 2/2013 | Storck et al. |

FOREIGN PATENT DOCUMENTS

| | | |
|---|---|---|
| CN | 101537007 A | 9/2009 |
| CN | 103373996 | 10/2013 |
| CN | 101671336 | 11/2013 |
| JP | 2001302666 | 10/2001 |
| WO | WO9635690 A1 | 11/1996 |
| WO | WO2011022439 A1 | 11/1996 |
| WO | WO9835110 A1 | 1/1998 |
| WO | WO9833799 A1 | 8/1998 |
| WO | WO0053605 A1 | 9/2000 |
| WO | WO0140231 A1 | 6/2001 |

(Continued)

OTHER PUBLICATIONS

S. Ahmed et al., "Synthesis of some Pyrazolopyrimidines as Purine Analogues", J. Heterocyclic Chem., 44, 803 (2007).
O. Ahmed et al., "Synthesis and anti-tumor activities of some new pyridines and pyrazolo[1,5-a]pyrimidines", European Journal of Medicinal Chemistry 44 (2009) 3519-3523.
M. Elnagdi et al., "Synthesis of Substituted Azaindenes: Synthesis of New Pyrazolo[1,5-a]pyrimidine Derivatives", Bull. Chem. Soc. Jpn., 63, 1854-1856 (1990).

(Continued)

Primary Examiner — Bruck Kifle
(74) Attorney, Agent, or Firm — Rory C. Stewart

(57) ABSTRACT

The present invention relates to compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of this invention have formula I:

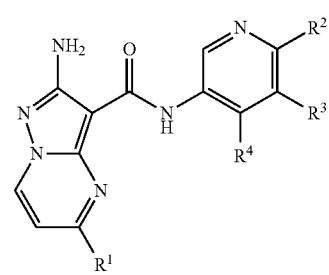

or a pharmaceutically acceptable salt, wherein the variables $R^1$, $R^2$, $R^3$, and $R^4$ are as defined herein.

70 Claims, No Drawings

(56) References Cited

FOREIGN PATENT DOCUMENTS

| | | |
|---|---|---|
| WO | WO0192257 A1 | 12/2001 |
| WO | WO0240485 A2 | 5/2002 |
| WO | WO02066481 A1 | 8/2002 |
| WO | WO03000187 A2 | 1/2003 |
| WO | WO03037900 A2 | 5/2003 |
| WO | WO03101993 A2 | 12/2003 |
| WO | WO2004022559 A1 | 3/2004 |
| WO | WO2004022560 A1 | 3/2004 |
| WO | WO2004022561 A1 | 3/2004 |
| WO | WO2004026229 A2 | 4/2004 |
| WO | WO2004052315 A2 | 6/2004 |
| WO | WO2004076458 A1 | 9/2004 |
| WO | WO2005028434 A2 | 3/2005 |
| WO | WO2005051906 A2 | 6/2005 |
| WO | WO2005077954 A2 | 8/2005 |
| WO | WO2005080396 A2 | 9/2005 |
| WO | WO2005117909 A2 | 12/2005 |
| WO | WO2006052913 A1 | 5/2006 |
| WO | WO2006071752 A1 | 7/2006 |
| WO | WO2006087120 A2 | 8/2006 |
| WO | WO2006128184 A2 | 11/2006 |
| WO | WO2007041712 A1 | 4/2007 |
| WO | WO2007044401 A2 | 4/2007 |
| WO | WO2007044407 A2 | 4/2007 |
| WO | WO2007044410 A1 | 4/2007 |
| WO | WO2007044420 A2 | 4/2007 |
| WO | WO2007044426 A1 | 4/2007 |
| WO | WO2007044441 A2 | 4/2007 |
| WO | WO2007044449 A2 | 4/2007 |
| WO | WO2007046548 A1 | 4/2007 |
| WO | WO2007048066 A2 | 4/2007 |
| WO | WO2007126841 A2 | 11/2007 |
| WO | WO2007139732 A1 | 12/2007 |
| WO | WO2007139856 A2 | 12/2007 |
| WO | WO2007139860 A2 | 12/2007 |
| WO | WO2008004698 A2 | 1/2008 |
| WO | WO2008008539 A2 | 1/2008 |
| WO | WO2008045266 A2 | 4/2008 |
| WO | WO2008045268 A2 | 4/2008 |
| WO | WO2008063671 A2 | 5/2008 |
| WO | WO2008130569 A1 | 10/2008 |
| WO | WO2008130570 A1 | 10/2008 |
| WO | WO2008151735 A2 | 12/2008 |
| WO | WO2009006580 A1 | 1/2009 |
| WO | WO2010002483 A1 | 1/2009 |
| WO | WO2010006086 A2 | 1/2009 |
| WO | WO2009017954 A1 | 2/2009 |
| WO | WO2009070567 A1 | 6/2009 |
| WO | WO2009075790 A1 | 6/2009 |
| WO | WO2009088986 | 7/2009 |
| WO | WO2009091374 A2 | 7/2009 |
| WO | WO2009095254 A1 | 8/2009 |
| WO | WO2009117157 A1 | 9/2009 |
| WO | WO2010017047 A1 | 2/2010 |
| WO | WO2010034738 A2 | 4/2010 |
| WO | WO2010051549 A1 | 5/2010 |
| WO | WO2010059836 A1 | 5/2010 |
| WO | WO2010086040 A1 | 8/2010 |
| WO | WO2010091409 A1 | 8/2010 |
| WO | WO2011003065 A2 | 1/2011 |
| WO | WO2011068667 A1 | 6/2011 |
| WO | WO2011121096 A1 | 6/2011 |
| WO | WO2011113606 A1 | 9/2011 |
| WO | WO2011163518 A1 | 12/2011 |
| WO | WO2012007375 A1 | 1/2012 |
| WO | WO2012022045 A1 | 2/2012 |
| WO | 2012/027236 A1 | 3/2012 |
| WO | WO2013010136 A1 | 3/2012 |
| WO | WO2012067822 A1 | 5/2012 |
| WO | WO2012078855 A1 | 6/2012 |
| WO | WO2012143510 A1 | 10/2012 |
| WO | WO2012143796 A2 | 10/2012 |
| WO | WO2012177997 A1 | 12/2012 |
| WO | WO2013010136 A2 | 1/2013 |
| WO | WO2013052263 A2 | 4/2013 |
| WO | WO2013138436 A1 | 10/2013 |
| WO | WO2013151930 A1 | 10/2013 |
| WO | WO2013151938 A1 | 10/2013 |
| WO | WO2013154878 | 10/2013 |
| WO | WO9854093 A1 | 11/2013 |
| WO | WO2013174930 A2 | 11/2013 |
| WO | WO2013174931 A1 | 11/2013 |
| WO | WO2014011911 A2 | 1/2014 |
| WO | WO2014015523 A1 | 1/2014 |
| WO | WO2014023691 A1 | 2/2014 |
| WO | WO2014025850 A1 | 2/2014 |
| WO | WO2014025852 A1 | 2/2014 |
| WO | WO2014025854 A1 | 2/2014 |
| WO | WO2014026984 A1 | 2/2014 |
| WO | WO2014029723 A1 | 2/2014 |
| WO | WO2014035140 A2 | 3/2014 |
| WO | WO2014039831 A1 | 3/2014 |
| WO | WO2014042433 A2 | 3/2014 |
| WO | WO2014044691 A1 | 3/2014 |
| WO | WO2014047648 A1 | 3/2014 |
| WO | WO2014066435 | 5/2014 |
| WO | WO2014066552 | 5/2014 |
| WO | WO2014089379 | 6/2014 |

OTHER PUBLICATIONS

Y. Ho, "Studies on the Synthesis of New 3-(3,5-Diamino-1-substituted-pyrazol-4-yl)azo-thieno[2,3-b]pyridines and 3-(2-Amino-5,7-disubstituted-pyrazolo[1,5-a]pyrimidine-3-yl)azo-thieno[2,3-b]pyridines", Journal of the Chinese Chemical Society, 1999, 46, 955-967.

A. Hussein, "Novel Synthesis of Some New Pyrimido[1,6-a]pyrimidine and Pyrazolo[1,5-a]pyrimidine Derivatives", J. Heterocyclic Chem., 49, 446, (2012).

International Search Report received in the corresponding PCT Application No. PCT/US/2005040344.

I. Otero et al., "Syntheses of Acyclo-C-nucleoside Analogs from 2,3:4,5-Di-Oisopropylidene-Di-O-isopropylidene-D-xylose", Journal of Carbohydrate Chemistry, 24:809-829, 2005.

I. Otero et al., "Synthesis of Iso-C-nucleoside Analogues from 1-(Methyl 2-O-benzyl]-4,6-O-benzylidene-3-deoxy-a-D-altropyranosid-3-yl)but-3-yn-2-ones", Z. Naturforsch. 60b, 1175-1185 (2005).

V. Ram et al., "Synthesis of bioisosteric pyrazolo[1,5-a]pyrimidines as leishmanicides", Indian Journal of Chemistry, vol. 34B, Jun. 1995, pp. 514-520.

V. Ried "Synthese neuer Heterocyclen ausgehend von Aminopyrazolen", Chemiker-Zeitung, 113. Jahrgang (1989) Nr. 5.

Non-Final Office Action dated Jun. 27, 2014 in U.S. Appl. No. 14/098,640.

COMPOUNDS USEFUL AS INHIBITORS OF ATR KINASE

CROSS-REFERENCE TO RELATED APPLICATIONS

The present application claims the benefit under 35 U.S.C. §119 of U.S. Provisional Application No. 61/788,644, filed Mar. 15, 2013.

SEQUENCE LISTING

The instant application contains a Sequence Listing in .txt format which has been submitted via EFS-Web and is hereby incorporated by reference in its entirety. The Sequence Listing, created on Jun. 2, 2014, is named VPI13112US.txt and is 854 bytes in size.

BACKGROUND OF THE INVENTION

ATR ("ATM and Rad3 related") kinase is a protein kinase involved in cellular responses to certain forms of DNA damage (e.g., double strand breaks and replication stress). ATR kinase acts with ATM ("ataxia telangiectasia mutated") kinase and many other proteins to regulate a cell's response to double strand DNA breaks and replication stress, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinases ATR and ATM. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

ATR peptide can be expressed and isolated using a variety of methods known in the literature (see e.g., Ünsal-Kaçmaz et al, *PNAS* 99: 10, pp 6673-6678, May 14, 2002; see also Kumagai et al. *Cell* 124, pp 943-955, Mar. 10, 2006; Unsal-Kacmaz et al. *Molecular and Cellular Biology*, February 2004, p 1292-1300; and Hall-Jackson et al. *Oncogene* 1999, 18, 6707-6713).

For all of these reasons, there is a need for the development of potent and selective ATR inhibitors for the treatment of cancer, either as single agents or as combination therapies with radiotherapy or genotoxic chemotherapy.

SUMMARY OF THE INVENTION

The present invention relates to compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of the invention are very potent ATR inhibitors. These compounds also show surprising synergy with other cancer agents, such as cisplatin and gemcitabine, in combination therapies.

DETAILED DESCRIPTION OF THE INVENTION

One aspect of the invention provides a compound of Formula I:

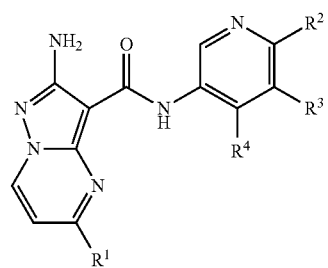

or a pharmaceutically acceptable salt or prodrug thereof, wherein:

$R^1$ is independently selected from $-(L^1)_n$-W or M;

M and $L^1$ are a $C_{1-8}$aliphatic wherein up to three methylene units are optionally replaced with —O—, —NR—, —C(O)—, or —S(O)$_z$—, each M and $L^1$ is optionally substituted with 0-3 occurrences of $J^{LM}$;

$J^{LM}$ is independently selected from halo, —CN, or a $C_{1-4}$aliphatic chain wherein up to two methylene units of the aliphatic chain are optionally replaced with —O—, —NR—, —C(O)—, or —S(O)$_z$—;

n is independently selected from 0 or 1;

W is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein W is optionally substituted with 0-5 occurrences of $J^W$;

$J^W$ is independently selected from —CN, halo, —CF$_3$; a $C_{1-4}$aliphatic wherein up to two methylene units are optionally replaced with —O—, —NR—, —C(O)—, or —S(O)$_z$—; or a 3-6 membered non-aromatic ring having 0-2 heteroatoms selected from oxygen, nitrogen, or sulfur;

two occurrences of $J^W$ on the same atom, together with atom to which they are joined, form a 3-6 membered ring having 0-2 heteroatoms selected from oxygen, nitrogen, or sulfur; or two occurrences of $J^W$, together with W, form a 6-10 membered saturated or partially unsaturated bridged ring system;

$R^2$ is independently selected from H; halo; —CN; a $C_{1-2}$alkyl optionally substituted with 1-3 occurrences of fluoro; or a $C_{1-3}$aliphatic chain wherein up to two methylene units of the aliphatic chain are optionally replaced with —O—, —NR—, —C(O)—, or —S(O)$_z$—;

$R^3$ is independently selected from H; halo; $C_{1-4}$alkyl optionally substituted with 1-3 occurrences of halo; $C_{3-4}$cycloalkyl; 3-4 membered heterocyclyl —CN; or a $C_{1-3}$aliphatic chain wherein up to two methylene units of the aliphatic chain are optionally replaced with —O—, —NR—, —C(O)—, or —S(O)$_z$—;

$R^4$ is independently selected from -(L$^2$)$_k$-Q$^1$ or T;

$L^2$ and T are each independently a $C_{1-10}$aliphatic chain wherein up to three methylene units of the aliphatic chain are optionally replaced with —O—, —NR—, —C(O)—, or —S(O)$_z$—; each $L^2$ and T is optionally substituted with 0-5 occurrences of $J^{LT}$;

$J^{LT}$ is independently selected from —CN; halo or a $C_{1-4}$aliphatic chain wherein up to two methylene units of the aliphatic chain are optionally replaced with —O—, —NR—, —C(O)—, or —S(O)$_z$—;

k is 0 or 1;

$Q^1$ is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein $Q^1$ is independently substituted with 0-5 occurrences of $J^Q$;

$J^Q$ is independently selected from —CN; halo; =O; Q$^2$; or a $C_{1-8}$aliphatic chain wherein up to three methylene units of the aliphatic chain are optionally replaced with —O—, —NR—, —C(O)—, or —S(O)$_z$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with Q$^1$, form a 6-10 membered saturated or partially unsaturated bridged ring system;

$Q^2$ is independently a 3-7 membered fully saturated, partially unsaturated, or aromatic monocyclic ring having 0-3 heteroatoms selected from oxygen, nitrogen, or sulfur; or a 7-12 membered fully saturated, partially unsaturated, or aromatic bicyclic ring having 0-5 heteroatoms selected from oxygen, nitrogen, or sulfur $J^R$ is independently selected from —CN, halo; =O; →O; Q$^3$; or a $C_{1-6}$aliphatic chain wherein up to two methylene units of the aliphatic chain are optionally replaced with —O—, —NR—, —S—, —C(O)—, or —S(O)$_z$—; each $J^R$ is optionally substituted with 0-3 occurrences of $J^P$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with Q$^2$, form a 6-10 membered saturated or partially unsaturated bridged ring system;

$Q^3$ is a 3-7 membered fully saturated, partially unsaturated, or aromatic monocyclic ring having 0-3 heteroatoms selected from oxygen, nitrogen, or sulfur; or a 7-12 membered fully saturated, partially unsaturated, or aromatic bicyclic ring having 0-5 heteroatoms selected from oxygen, nitrogen, or sulfur;

$J^X$ is independently selected from —CN, halo or a $C_{1-4}$aliphatic chain wherein up to two methylene units of the aliphatic chain are optionally replaced with —O—, —NR—, —C(O)—, or —S(O)$_z$—; or $J^P$ is independently selected from —CN; =O; halo; a $C_{1-6}$aliphatic chain wherein up to two methylene units of the aliphatic chain are optionally replaced with —O—, —NR—, —C(O)—, or —S(O)$_z$—; or a 3-6 membered non-aromatic ring having 0-2 heteroatoms selected from oxygen, nitrogen, or sulfur; each $J^P$ is optionally substituted with 0-3 occurrences of $J^M$; or two occurrences of $J^P$ on the same atom, together with the atom to which they are joined, form a 3-6 membered ring having 0-2 heteroatoms selected from oxygen, nitrogen, or sulfur; or two occurrences of $J^P$, together with Q$^3$, form a 6-10 membered saturated or partially unsaturated bridged ring system;

$J^M$ is independently selected from halo or $C_{1-6}$aliphatic;

z is 0, 1 or 2; and

R is independently selected from H or $C_{1-4}$aliphatic.

One aspect of the invention provides a compound of Formula I:

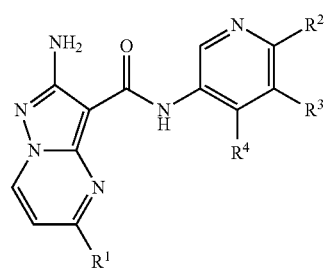

or a pharmaceutically acceptable salt or prodrug thereof, wherein:

$R^1$ is independently selected from -(L$^1$)$_n$-W or M;

M and $L^1$ are a $C_{1-8}$aliphatic wherein up to three methylene units are optionally replaced with —O—, —NR—, —C(O)—, or —S(O)$_z$—, each $L^1$ is optionally substituted with 0-3 occurrences of $J^{LM}$;

$J^{LM}$ is independently selected from halo, —CN, or a $C_{1-4}$aliphatic chain wherein up to two methylene units of the aliphatic chain are optionally replaced with —O—, —NR—, —C(O)—, or —S(O)$_z$—;

n is independently selected from 0 or 1;

W is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein W is optionally substituted with 0-5 occurrences of $J^W$;

$J^W$ is independently selected from —CN, halo, —CF$_3$; a $C_{1-4}$aliphatic wherein up to two methylene units are optionally replaced with —O—, —NR—, —C(O)—, or —S(O)$_z$—; or a 3-6 membered non-aromatic ring having 0-2 heteroatoms selected from oxygen, nitrogen, or sulfur;

two occurrences of $J^W$ on the same atom, together with atom to which they are joined, form a 3-6 membered ring having 0-2 heteroatoms selected from oxygen, nitrogen, or sulfur; or two occurrences of $J^W$, together with W, form a 6-10 membered saturated or partially unsaturated bridged ring system;

$R^2$ is independently selected from H; halo; —CN; a $C_{1-2}$alkyl optionally substituted with 1-3 occurrences of fluoro; or a $C_{1-3}$aliphatic chain wherein up to two methylene units of the aliphatic chain are optionally replaced with —O—, —NR—, —C(O)—, or —S(O)$_z$;

$R^3$ is independently selected from H; halo; $C_{1-4}$alkyl optionally substituted with 1-3 occurrences of halo; $C_{3-4}$cycloalkyl; —CN; or a $C_{1-3}$aliphatic chain wherein up to two methylene units of the aliphatic chain are optionally replaced with —O—, —NR—, —C(O)—, or —S(O)$_z$;

$R^4$ is independently selected from -($L^2$)$_k$-$Q^1$ or T;

$L^2$ and T are each independently a $C_{1-10}$aliphatic chain wherein up to three methylene units of the aliphatic chain are optionally replaced with —O—, —NR—, —C(O)—, or —S(O)$_z$—; each $L^2$ and T is optionally substituted with 0-5 occurrences of $J^{LT}$;

$J^{LT}$ is independently selected from —CN; halo or a $C_{1-4}$aliphatic chain wherein up to two methylene units of the aliphatic chain are optionally replaced with —O—, —NR—, —C(O)—, or —S(O)$_z$—;

k is 0 or 1;

$Q^1$ is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein $Q^1$ is independently substituted with 0-5 occurrences of $J^Q$;

$J^Q$ is independently selected from —CN; halo; =O; $Q^2$; or a $C_{1-8}$aliphatic chain wherein up to three methylene units of the aliphatic chain are optionally replaced with —O—, —NR—, —C(O)—, or —S(O)$_z$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with $Q^1$, form a 6-10 membered saturated or partially unsaturated bridged ring system;

$Q^2$ is independently a 3-7 membered fully saturated, partially unsaturated, or aromatic monocyclic ring having 0-3 heteroatoms selected from oxygen, nitrogen, or sulfur; or a 7-12 membered fully saturated, partially unsaturated, or aromatic bicyclic ring having 0-5 heteroatoms selected from oxygen, nitrogen, or sulfur $J^R$ is independently selected from —CN, halo; =O; →O; $Q^3$; or a $C_{1-6}$aliphatic chain wherein up to two methylene units of the aliphatic chain are optionally replaced with —O—, —NR—, —S—, —C(O)—, or —S(O)$_z$—; each $J^R$ is optionally substituted with 0-3 occurrences of $J^P$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from oxygen, nitrogen, or sulfur; or a 7-12 membered fully saturated, partially unsaturated, or aromatic bicyclic ring having 0-5 heteroatoms selected from oxygen, nitrogen, or sulfur;

$J^X$ is independently selected from —CN, halo or a $C_{1-4}$aliphatic chain wherein up to two methylene units of the aliphatic chain are optionally replaced with —O—, —NR—, —C(O)—, or —S(O)$_z$—; or $J^P$ is independently selected from —CN; =O; halo; a $C_{1-6}$aliphatic chain wherein up to two methylene units of the aliphatic chain are optionally replaced with —O—, —NR—, —C(O)—, or —S(O)$_z$—; or a 3-6 membered non-aromatic ring having 0-2 heteroatoms selected from oxygen, nitrogen, or sulfur; or two occurrences of $J^P$ on the same atom, together with the atom to which they are joined, form a 3-6 membered ring having 0-2 heteroatoms selected from oxygen, nitrogen, or sulfur; or two occurrences of $J^P$, together with $Q^3$, form a 6-10 membered saturated or partially unsaturated bridged ring system;

z is 0, 1 or 2; and

R is independently selected from H or $C_{1-4}$aliphatic.

For purposes of this application, it will be understood that when two occurrences of $J^Q$, together with $Q^1$, form a bridged ring system, the two occurrences of $J^Q$ are attached to separate atoms of $Q^1$. Additionally, when two occurrences of $J^R$, together with $Q^2$, form a bridged ring system, the two occurrences of $J^R$ are attached to separate atoms of $Q^2$. Moreover, when two occurrences of $J^P$, together with $Q^3$, form a bridged ring system, the two occurrences of $J^P$ are attached to separate atoms of $Q^3$. Finally, when two occurrences of $J^W$, together with W, form a bridged ring system, the two occurrences of $J^W$ are attached to separate atoms of W.

Moreover, it will be understood by those skilled in the art that the arrow in →O represents a dative bond.

In one or more aspects of the present invention, $R^1$ is M. In another aspect of the present invention, M is a $C_{1-8}$aliphatic wherein up to three methylene units are optionally replaced with —O— or —NR—. In some aspects, M is $C_{1-4}$alkyl, —($C_{1-4}$alkyl)O($C_{1-3}$aliphatic), —($C_{1-3}$alkyl)OH, —O($C_{1-4}$alkyl)N($C_{1-2}$alkyl)$_2$, —NH($C_{1-4}$alkyl), or —($C_{1-4}$alkyl)NH($C_{1-4}$alkyl). In yet another aspect of the present invention, M is $C_{1-4}$alkyl.

In one or more embodiments of the present invention, $J^{LM}$ is halo.

In some embodiments of the present invention, $R^1$ is -($L^1$)$_n$-W.

In another example, n is 1. In other examples n is 0.

In one or more aspects of the present invention, $L^1$ is a $C_{1-8}$aliphatic wherein up to three methylene units are optionally replaced with —O— or —NR—. In other aspects of the invention, $L^1$ is —O—, —O(C1-4aliphatic)-, or —NR($C_{1-3}$alkyl)-.

In one or more embodiments, W is a 3-7 membered fully saturated, partially unsaturated, or aromatic monocyclic ring having 0-3 heteroatoms selected from oxygen, nitrogen or sulfur. In some embodiments, W is a 3-7 membered heterocyclyl. In another embodiment, W is independently selected from pyrrolidinyl, piperidinyl, piperazinyl, oxetanyl, or azetidinyl.

In other embodiments, W is a 7-12 membered fully saturated, partially unsaturated, or aromatic bicyclic ring having 0-5 heteroatoms selected from oxygen, nitrogen, or sulfur. In yet another embodiment, W is octahydropyrrolo[1,2-a]pyrazine.

In some aspects of the present invention, $J^W$ is selected form $C_{1-3}$alkyl or $CF_3$. In other aspects of the invention, two occurrences of $J^W$ on the same atom, together with atom to which they are joined, form a 3-6 membered ring having 0-2 heteroatoms selected from oxygen, nitrogen, or sulfur. In yet another aspect of the invention, the ring formed by the two occurrences of $J^W$ on the same atom is oxetanyl.

In another embodiment, $R^2$ is H or chloro. In some embodiments, $R^2$ is H.

In yet another example, $R^3$ is H or chloro. In other examples, $R^3$ is H.

In some embodiments, $R^4$ is $-(L^2)_k-Q^1$.

In one or more aspects of the present invention, k is 1. In other aspects of the invention, k is 0.

In some embodiments, $L^2$ is —O—.

In one or more examples, $Q^1$ is independently selected from a 3-7 membered fully saturated, partially unsaturated, or aromatic monocyclic ring having 0-3 heteroatoms selected from oxygen, nitrogen or sulfur.

In another example, $Q^1$ is a 3-7 membered heterocyclyl or carbocycle. In other examples, $Q^1$ is independently selected from cyclopropyl, cyclobutyl, cyclopentyl, cyclohexyl, cycloheptyl, pyrrolidinyl, piperidinyl, azepanyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, dihydroimidazolyl, 1,3-tetrahydropyrimidinyl, dihydropyrimidinyl, 1,4-diazepanyl, 1,4-oxazepanyl, 1,4-thiazepanyl, and azetidinyl. In still other examples, $Q^1$ is independently selected from pyrrolidinyl, cyclopropyl, cyclohexyl, piperidinyl or piperazinyl.

In some aspects of the present invention, $Q^1$ is a 5-6 membered aryl or heteroaryl. In another aspect of the present invention, $Q^1$ is independently selected from phenyl, pyridinyl, pyrazinyl, pyrimidinyl, tetrahydropyridinyl, pyrrolyl, imidazolyl, pyrazolyl, 1,2,3-triazolyl, or 1,2,4-triazolyl. In yet another aspect of the invention, $Q^1$ is pyridinyl.

In one or more embodiments, $Q^1$ is a 7-12 membered fully saturated, partially unsaturated, or aromatic bicyclic ring having 1-5 heteroatoms selected from oxygen, nitrogen, or sulfur. In some embodiments, $Q^1$ is independently selected from octahydropyrrolo[1,2-a]pyrazinyl, 5,6,7,8-tetrahydroimidazo[1,2-a]pyridinyl, octahydro-1H-pyrazino[1,2-a]pyrazinyl, 5,6,7,8-tetrahydroimidazo[1,5-a]pyrazinyl, 2,5-diazabicyclo[4.1.0]heptane, or octahydropyrazino[2,1-a][1,4]oxazinyl.

In one or more embodiments, $J^Q$ is $C_{1-6}$aliphatic chain wherein up to two methylene units of the aliphatic chain are optionally replaced with —O—, —NR—, or —C(O)—. In some embodiments, $J^Q$ is independently selected from —C(O)—, $C_{1-4}$alkyl, —($C_{0-4}$alkyl)$NH_2$, —($C_{0-4}$alkyl)NH($C_{1-4}$alkyl), —($C_{0-4}$alkyl)N($C_{1-4}$alkyl)$_2$, —($C_{0-4}$alkyl)OH, —($C_{0-4}$alkyl)O($C_{1-4}$alkyl), —C(O)OH, —C(O)O($C_{1-4}$alkyl), N($C_{1-4}$alkyl)$_2$, —C(O)N($C_{1-4}$alkyl)$_2$, or —($C_{1-3}$alkyl)O($C_{1-2}$alkyl)N($C_{1-3}$alkyl)$_2$. In still other embodiments, $J^Q$ is independently selected from —C(O)—, $C_{1-4}$alkyl, or —($C_{0-4}$alkyl)$NH_2$.

In some aspects of the present invention, $J^Q$ is $Q^2$. In other aspects of the present invention, $Q^2$ is a 3-7 membered fully saturated, partially unsaturated, or aromatic monocyclic ring having 0-3 heteroatoms selected from oxygen, sulfur, or nitrogen. In another aspect of the present invention, $Q^2$ is independently selected from selected from cyclopropyl, cyclobutyl, cyclopentyl, cyclohexyl, oxetanyl, tetrahydropyranyl, tetrahydrofuranyl, azetidinyl, pyrrolidinyl, piperidinyl, piperazinyl, thiomorpholinyl, or morpholinyl. In yet another aspect of the invention, $Q^2$ is oxetanyl, pyrrolidinyl, or tetrahydropyranyl.

In one or more embodiments, $Q^2$ is a 7-12 membered fully saturated, partially unsaturated, or aromatic bicyclic ring having 0-5 heteroatoms selected from oxygen, nitrogen, or sulfur. In still other embodiments, $Q^2$ is independently selected from 5,6,7,8-tetrahydroimidazo[1,5-a]pyrazinyl or 5,6,7,8-tetrahydroimidazo[1,2-a]pyrazinyl.

In one or more examples, two occurrences of $J^Q$, together with $Q^1$, form a bridged ring system.

In other embodiments, $J^Q$ is =O, halo, or →O.

In yet another embodiment, two occurrences of $J^Q$ on the same atom, taken together with the atom to which they are joined, form a 3-6 membered non-aromatic ring having 0-2 heteroatoms selected from oxygen, nitrogen, or sulfur. In still other embodiments, the two occurrences of $J^Q$ on the same atom, taken together with the atom to which they are joined, is selected from oxetanyl, cyclobutyl, or azetidinyl.

In one or more embodiments, $J^R$ is a 3-6 membered heterocyclyl having 1-3 heteroatoms selected from oxygen, nitrogen, or sulfur. In other embodiments, $J^R$ is independently selected from oxetanyl, piperadinyl, azetidinyl, piperazinyl, pyrrolidinyl, or morpholinyl. In some embodiments, $J^R$ is a piperazinyl.

In one or more aspects of the invention, $J^R$ is independently selected from halo, =O, —OH, $C_{1-4}$alkyl, —($C_{0-4}$alkyl)N($C_{1-4}$alkyl)$_2$, or —($C_{0-4}$alkyl)O($C_{1-4}$alkyl).

In another aspect of the invention, two occurrences of $J^R$ on the same atom, together with the atom to which they are joined, form a 3-6 membered aromatic or non-aromatic ring having 0-2 heteroatoms selected from oxygen, nitrogen, or sulfur.

In some embodiments, $J^P$ is —$C_{1-4}$alkyl.

In other embodiments, $R^4$ is T. In still other embodiments, T is independently selected from —($C_{1-4}$alkyl), —($C_{1-4}$alkyl)N($C_{1-4}$alkyl)$_2$, —($C_{1-3}$alkyl)O($C_{1-2}$alkyl)N($C_{1-3}$alkyl)$_2$, —($C_{1-4}$alkyl)OH, —($C_{1-4}$alkyl)$NH_2$, or —($C_{1-4}$alkyl)O($C_{1-4}$alkyl).

In one or more examples, $J^{LT}$ is halo or $C_{1-3}$alkyl.

One aspect of the present invention comprises a process for preparing a compound of formula I:

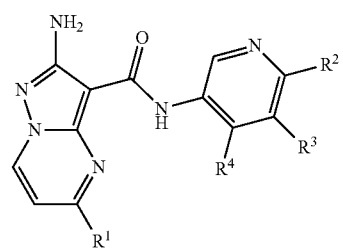

comprising reacting a compound of formula 6:

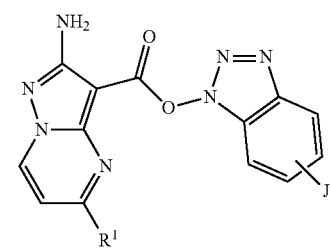

under suitable conditions to form an amide bond, wherein J, $R^1$, $R^2$, $R^3$ and $R^4$ are as defined in herein.

In some examples, the suitable conditions for forming the amide bond comprises reacting the compound of formula 6 with a substituted 3-amino pyridine in an aprotic solvent under heat. In other examples, the aprotic solvent is selected from NMP, optionally substituted pyridine, or DMF. In another embodiment, the aprotic solvent is optionally substituted pyridine. In still other embodiments, the reaction temperature is at least 80° C. In another embodiment, the reaction temperature is at least 100° C.

Another aspect of the present invention comprises a process for preparing a compound of formula 6:

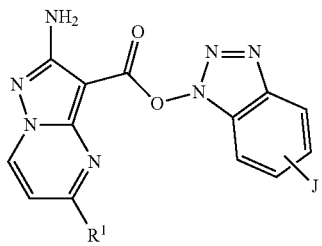

6 by reacting a compound of formula 5:

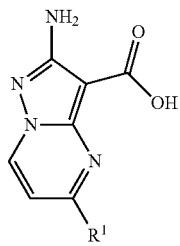

5 under suitable conditions to form an activated ester, wherein $R^1$ and J are as defined herein.

In some embodiments, suitable conditions for forming the activated ester comprises reacting the compound of formula 5 with an amide coupling agent in the presence of an organic base. In another embodiment, the organic basis is an aliphatic amine. In still other embodiments, the organic base is independently selected from triethylamine or DIPEA. In one or more embodiments, the amide coupling agent is independently selected from EDCI, TBTU, TCTU, HATU, T3P, or COMU. In yet another embodiment, the amide coupling agent is independently selected from TBTU or TCTU. In another embodiment, the amide coupling agent is TCTU.

Yet another aspect of the present invention comprises a process for preparing a compound of formula I:

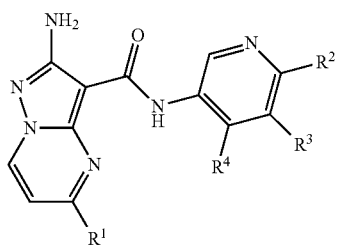

I comprising reacting a compound of formula 5:

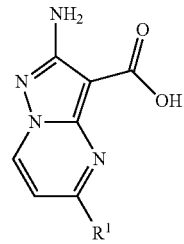

5 under suitable conditions to form an amide bond, wherein $R^1$, $R^2$, $R^3$ and $R^4$ are as defined herein.

Another embodiment of the invention comprises a process for preparing a compound of formula 5:

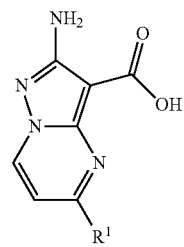

5 by reacting a compound of formula 4:

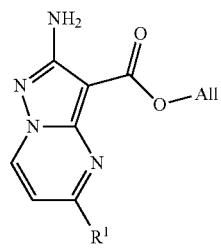

4 under suitable deprotection conditions.

In some embodiments, suitable deprotection conditions comprises reacting the compound of formula 4 under suitable hydrolytic conditions. In another embodiment, suitable hydrolytic conditions comprise reacting the compound of formula 4 with a silane in the presence of a metal catalyst. In other embodiments, the silane is a phenylsilane. In another embodiment, the metal catalyst is a palladium catalyst. In yet another embodiment, the palladium catalyst is $Pd(PPh_3)_4$. In another embodiment suitable hydrolytic conditions comprise reacting the compound of formula 4 with 4-methylbenzenesulfinate in the presence of a metal catalyst.

In still other embodiments, suitable hydrolytic conditions comprise reacting the compound of formula 4 with an aqueous alkali. In some embodiments, the aqueous alkali is selected from LiOH, NaOH or KOH.

Still another embodiment of the invention comprises a process for preparing a compound of formula 4:

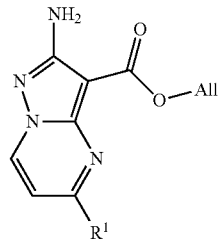

4 by reacting a compound of formula 3:

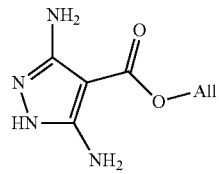

3 under suitable condensation conditions to form a pyrimidine ring.

In some embodiments, suitable condensation conditions to form a pyrimidine ring comprise reacting the compound of formula 3 with a 1,3-dielectrophilic species in the presence of a solvent. In another embodiment, the 1,3-dielectrophilic species is selected from methylprop-2-ynoate. In still other embodiments, the solvent is selected from DMF or DMSO in water. In other embodiments, the 1,3-dielectrophilic species is generated in situ from a protected 1,3-dielectrophilic species. In another embodiment, the protected 1,3-dielectrophilic species is 3-(1,3-dioxolan-2-yl)-1,1,1-trifluoropropan-2-one. In yet another embodiment, the 1,3 dielectrophilic species is generated by reacting 3-(1,3-dioxolan-2-yl)-1,1,1-trifluoropropan-2-one with sulfonic acid. In some embodiments, the sulfonic acid is PTSA.

Other embodiments of the invention comprise a process for preparing the compound of formula 3:

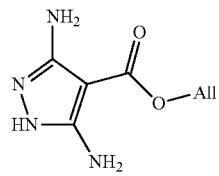

3 by reacting a compound of formula 2:

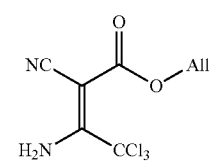

2 under suitable condensation conditions to form a pyrazole ring.

In some embodiments, suitable condensation conditions to form a pyrazole ring comprise reacting the compound of formula 2 with a hydrazine or hydrazine hydrate in the presence of an aprotic solvent under basic conditions. In another embodiment, the aprotic solvent is DMF. In yet another embodiment, the basic conditions comprise reacting the compound of formula 2 in the presence of potassium acetate or sodium acetate.

Another aspect of the present invention comprises a process for preparing a compound of formula 2:

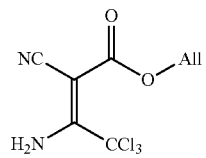

2 by reacting a compound of formula 1:

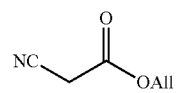

1 under suitable anion condensation conditions.

In some embodiments, suitable anion condensation conditions comprise 1) reacting the compound of formula 1 with a base, in the presence of a solvent, to generate the anion of the compound of formula 1; and 2) reacting the anion of the compound of formula 1 with trichloroacetonitrile. In still other embodiments, the base is potassium acetate. In yet another embodiment, the solvent is an alcohol. In other embodiments, the solvent is isopropylalcohol.

One embodiment of the present invention comprises a process for preparing a compound of formula I:

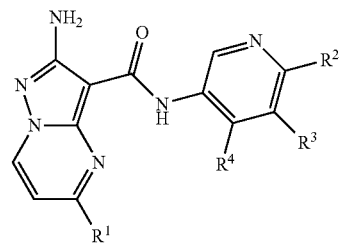

I comprising reacting a compound of formula 9:

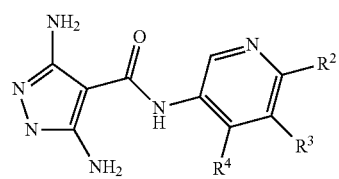

9 under suitable condensation conditions to form a pyrimidine ring, wherein R¹, R², R³ and R⁴ are as defined herein.

In some embodiments, suitable condensation conditions to form a pyrimidine ring comprise reacting the compound of formula 9 with a 1,3-dielectrophilic species in the presence of a solvent. In another embodiment, the 1,3-dielectrophilic species is selected from 3-(1,3-dioxolan-2-yl)-1,1,1-trifluoropropan-2-one. In still other embodiments, the solvent is selected from iPrOH in water, DMF, or DMSO in water. In other embodiments, the 1,3-dielectrophilic species is generated in situ from a protected 1,3-dielectrophilic species. In another embodiment the 1,3-dielectrophilic species is generated from a ketal in the presence of a sulfonic acid. In yet another embodiment, the sulfonic acid is PTSA.

Another embodiment of the present invention comprises a process for preparing a compound of formula 9:

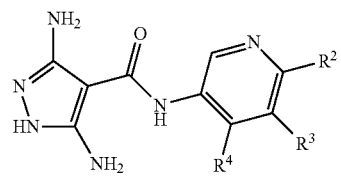
9 by reacting a compound of formula 8:

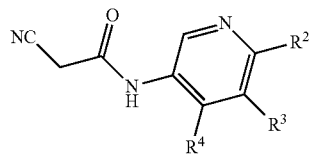
8 under suitable condensation conditions to form a pyrazole ring.

In some embodiments, suitable condensation conditions to form a pyrazole ring comprise 1) reacting the compound of formula 8 with a base, in the presence of a solvent, to generate the anion of the compound of formula 8; 2) reacting the anion with trichloroacetonitrile; and 3) reacting the product from 2) with a hydrazine or hydrazine hydrate in the presence of an aprotic solvent. In another embodiment, the aprotic solvent is NMP or DMF. In some embodiments, the base is selected from sodium acetate or potassium acetate.

Yet another embodiment comprises a process for preparing a compound of formula 8:

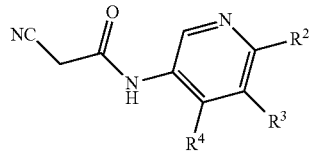
8 by reacting a compound of formula 7:

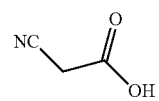
7 under suitable conditions to form an amide bond.

In some examples, the suitable conditions for forming the amide bond comprises reacting the compound of formula 7 with a substituted 3-amino pyridine and an amide coupling agent in the presence of an aprotic solvent and an organic base. In other examples, the aprotic solvent is selected from NMP or DMF. In another embodiment, the organic base is an aliphatic amine. In still other embodiments, the organic base is independently selected from triethylamine or DIPEA. In yet another embodiment, the amide coupling agent is independently selected from TBTU or TCTU. In still other embodiments, the reaction temperature is at least 80° C. In another embodiment, the reaction temperature is at least 100° C.

For purposes of this application, it will be understood that the terms embodiment, example, and aspect are used interchangeably.

In one or more aspects of the invention, the compounds of this invention are as represented in Table 1, below. It will be appreciated by those skilled in the art that the compounds of the present invention may be represented in varying tautomeric forms.

TABLE 1

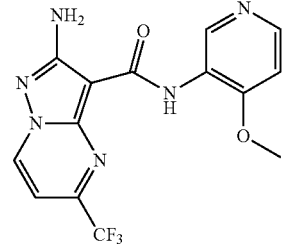 [SMILES: COc1ccncc1NC(=O)c1c(N)nn2ccc(C(F)(F)F)nc12]
I-O-1

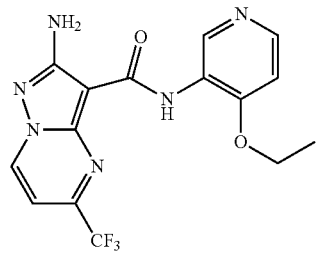 [SMILES: CCOc1ccncc1NC(=O)c1c(N)nn2ccc(C(F)(F)F)nc12]
I-O-2

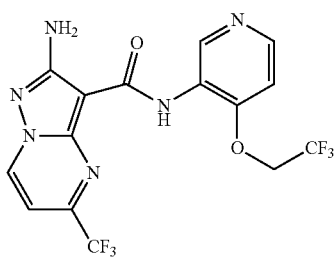 [SMILES: Nc1nn2ccc(C(F)(F)F)nc2c1C(=O)Nc1cnccc1OCC(F)(F)F]
I-O-3

TABLE 1-continued
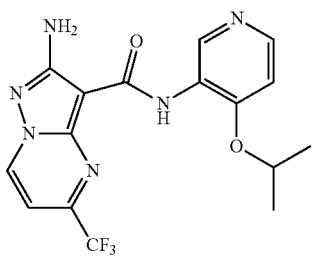 [SMILES: CC(C)Oc1ccncc1NC(=O)c1c(N)nn2ccc(C(F)(F)F)nc12] I-O-4
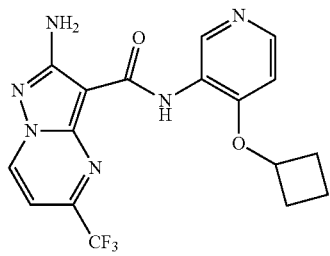 [SMILES: Nc1nn2ccc(C(F)(F)F)nc2c1C(=O)Nc1cnccc1OC1CCC1] I-O-5
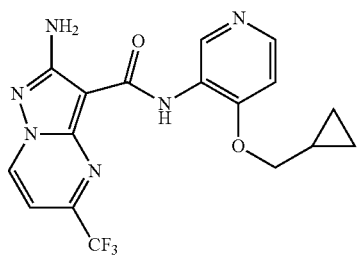 [SMILES: Nc1nn2ccc(C(F)(F)F)nc2c1C(=O)Nc1cnccc1OCC1CC1] I-O-6
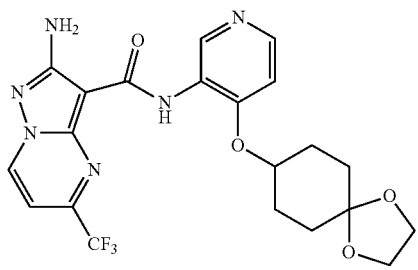 [SMILES: Nc1nn2ccc(C(F)(F)F)nc2c1C(=O)Nc1cnccc1OC1CCC2(CC1)OCCO2] I-O-7
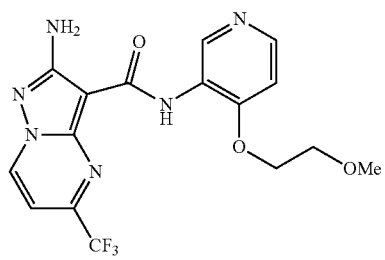 [SMILES: COCCOc1ccncc1NC(=O)c1c(N)nn2ccc(C(F)(F)F)nc12] I-O-8
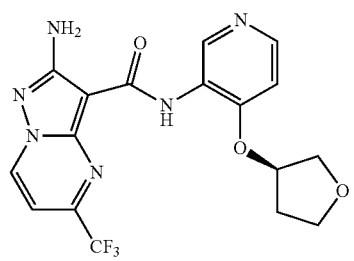 [SMILES: Nc1nn2ccc(C(F)(F)F)nc2c1C(=O)Nc1cnccc1O[C@@H]1CCOC1] I-O-9
TABLE 1-continued
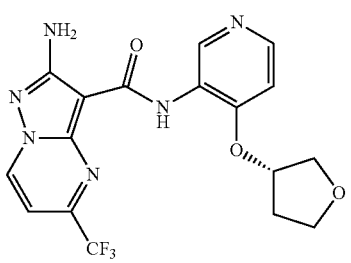 [SMILES: Nc1nn2ccc(C(F)(F)F)nc2c1C(=O)Nc1cnccc1O[C@H]1CCOC1] I-O-10
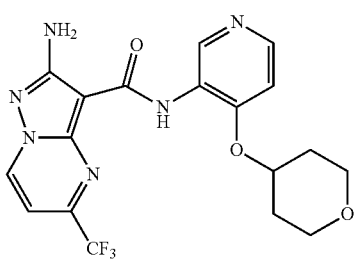 [SMILES: Nc1nn2ccc(C(F)(F)F)nc2c1C(=O)Nc1cnccc1OC1CCOCC1] I-O-11
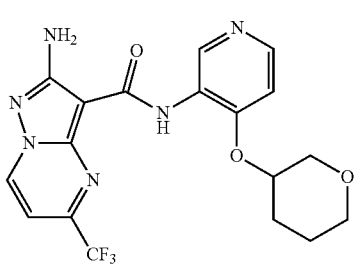 [SMILES: Nc1nn2ccc(C(F)(F)F)nc2c1C(=O)Nc1cnccc1OC1CCCOC1] I-O-12
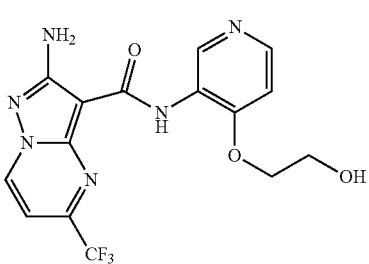 [SMILES: Nc1nn2ccc(C(F)(F)F)nc2c1C(=O)Nc1cnccc1OCCO] I-O-13
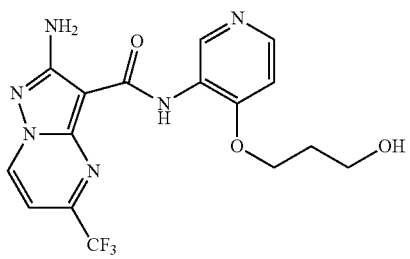 [SMILES: Nc1nn2ccc(C(F)(F)F)nc2c1C(=O)Nc1cnccc1OCCCO] I-O-14
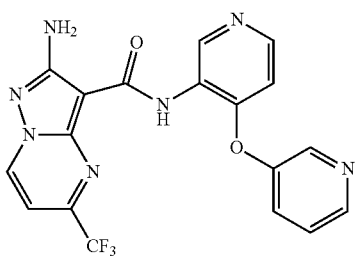 [SMILES: Nc1nn2ccc(C(F)(F)F)nc2c1C(=O)Nc1cnccc1Oc1cccnc1] I-O-15

TABLE 1-continued
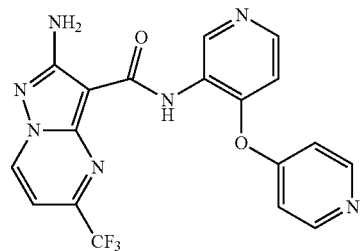 [SMILES: Nc1nn2ccc(C(F)(F)F)nc2c1C(=O)Nc1cnccc1Oc1ccncc1] I-O-16
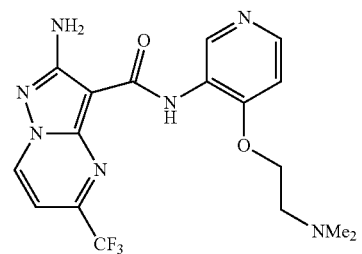 [SMILES: CN(C)CCOc1ccncc1NC(=O)c1c(N)nn2ccc(C(F)(F)F)nc12] I-O-17
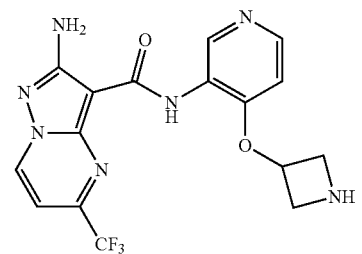 [SMILES: Nc1nn2ccc(C(F)(F)F)nc2c1C(=O)Nc1cnccc1OC1CNC1] I-O-18
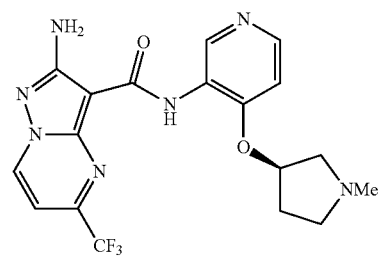 [SMILES: CN1CC[C@@H](Oc2ccncc2NC(=O)c2c(N)nn3ccc(C(F)(F)F)nc23)C1] I-O-19
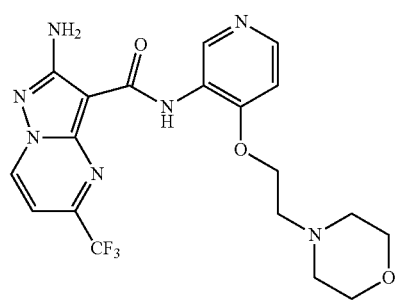 [SMILES: Nc1nn2ccc(C(F)(F)F)nc2c1C(=O)Nc1cnccc1OCCN1CCOCC1] I-O-20
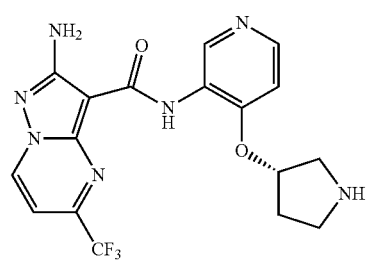 [SMILES: Nc1nn2ccc(C(F)(F)F)nc2c1C(=O)Nc1cnccc1O[C@H]1CCNC1] I-O-21
TABLE 1-continued
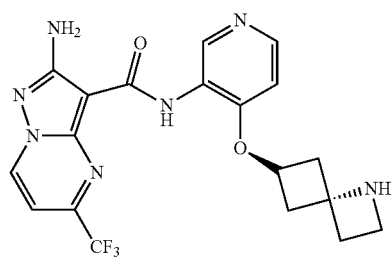 I-O-22
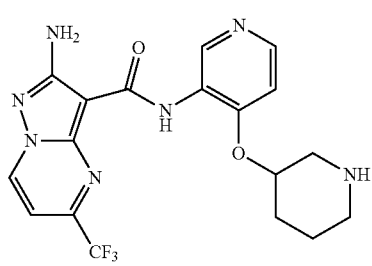 [SMILES: Nc1nn2ccc(C(F)(F)F)nc2c1C(=O)Nc1cnccc1OC1CCCNC1] I-O-23
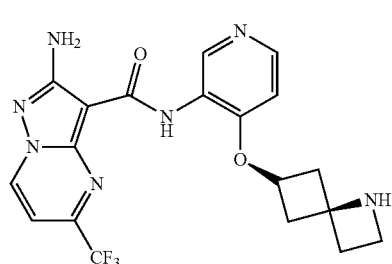 I-O-24
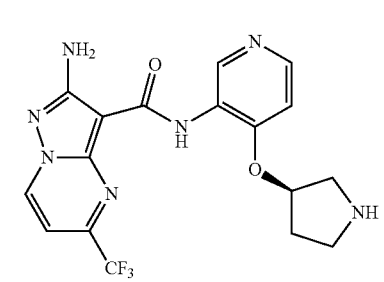 [SMILES: Nc1nn2ccc(C(F)(F)F)nc2c1C(=O)Nc1cnccc1O[C@@H]1CCNC1] I-O-25
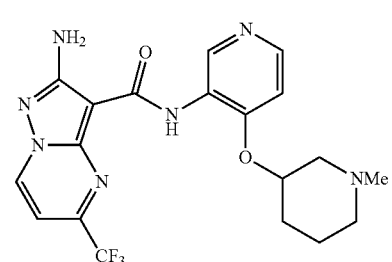 I-O-26
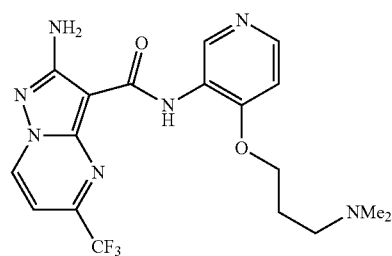 [SMILES: CN(C)CCCOc1ccncc1NC(=O)c1c(N)nn2ccc(C(F)(F)F)nc12] I-O-27

TABLE 1-continued
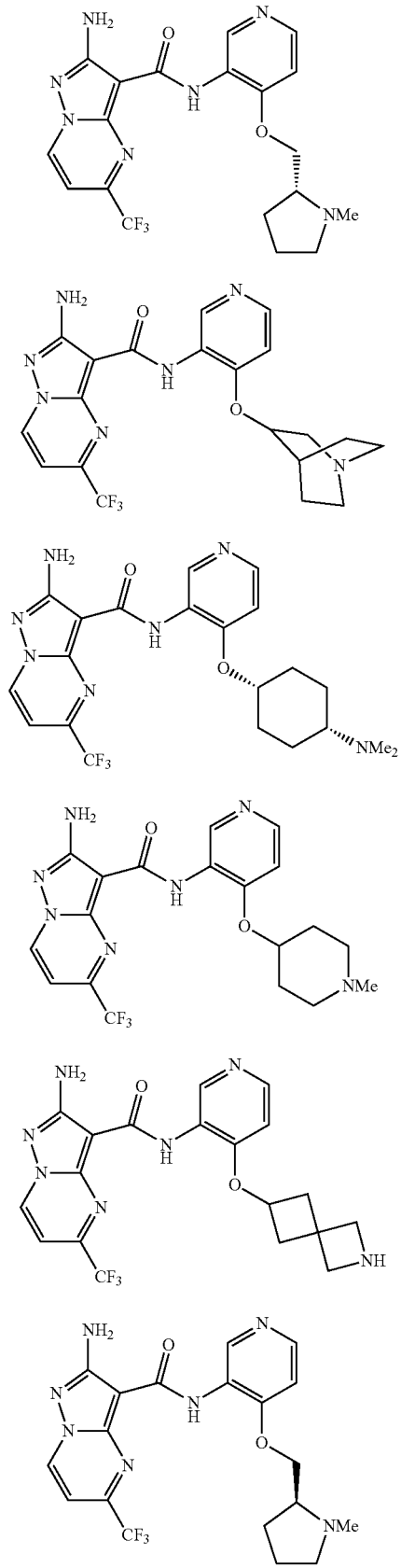
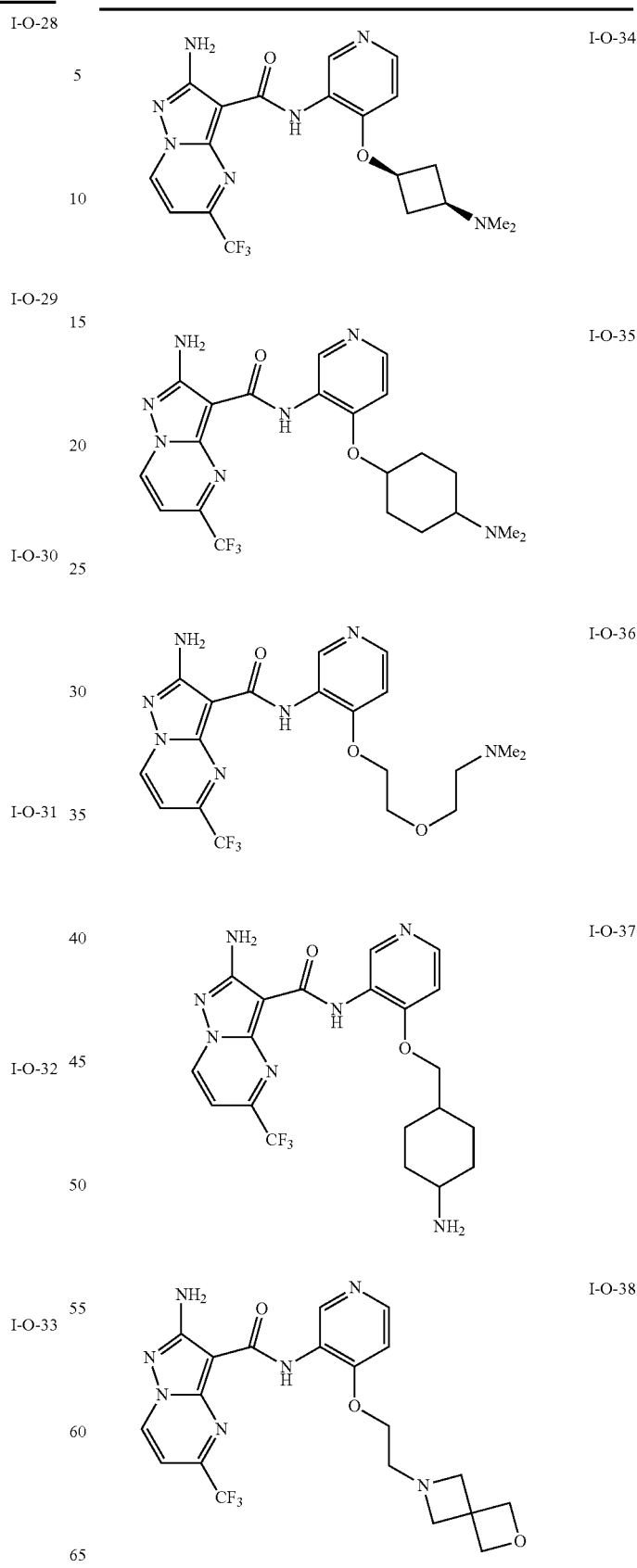

TABLE 1-continued

TABLE 1-continued
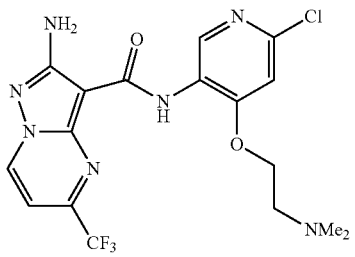 [SMILES: CN(C)CCOc1cc(Cl)ncc1NC(=O)c1c(N)nn2ccc(C(F)(F)F)nc12] I-O-50
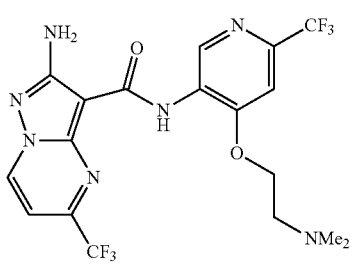 [SMILES: CN(C)CCOc1cc(C(F)(F)F)ncc1NC(=O)c1c(N)nn2ccc(C(F)(F)F)nc12] I-O-51
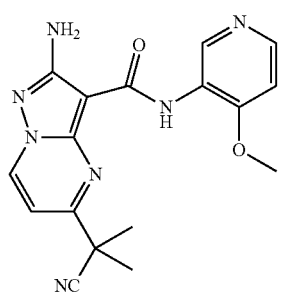 [SMILES: COc1ccncc1NC(=O)c1c(N)nn2ccc(C(C)(C)C#N)nc12] I-O-52
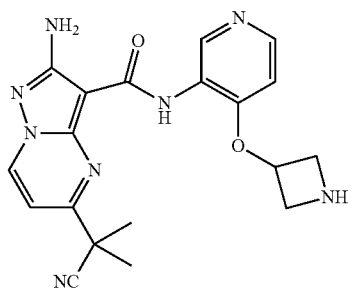 [SMILES: CC(C)(C#N)c1ccn2nc(N)c(C(=O)Nc3cnccc3OC3CNC3)c2n1] I-O-53
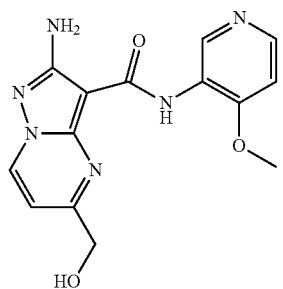 [SMILES: COc1ccncc1NC(=O)c1c(N)nn2ccc(CO)nc12] I-O-54
TABLE 1-continued
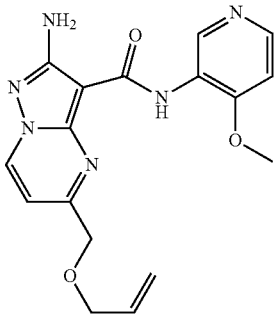 [SMILES: C=CCOCc1ccn2nc(N)c(C(=O)Nc3cnccc3OC)c2n1] I-O-55
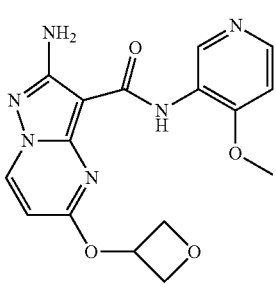 [SMILES: COc1ccncc1NC(=O)c1c(N)nn2ccc(OC3COC3)nc12] I-O-56
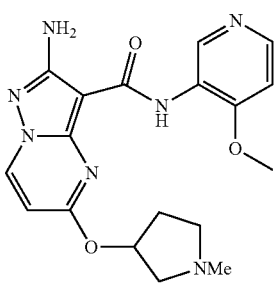 [SMILES: COc1ccncc1NC(=O)c1c(N)nn2ccc(OC3CCN(C)C3)nc12] I-O-57
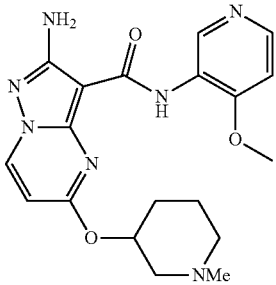 [SMILES: COc1ccncc1NC(=O)c1c(N)nn2ccc(OC3CCCN(C)C3)nc12] I-O-58
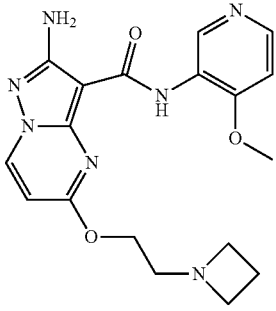 [SMILES: COc1ccncc1NC(=O)c1c(N)nn2ccc(OCCN3CCC3)nc12] I-O-59

TABLE 1-continued
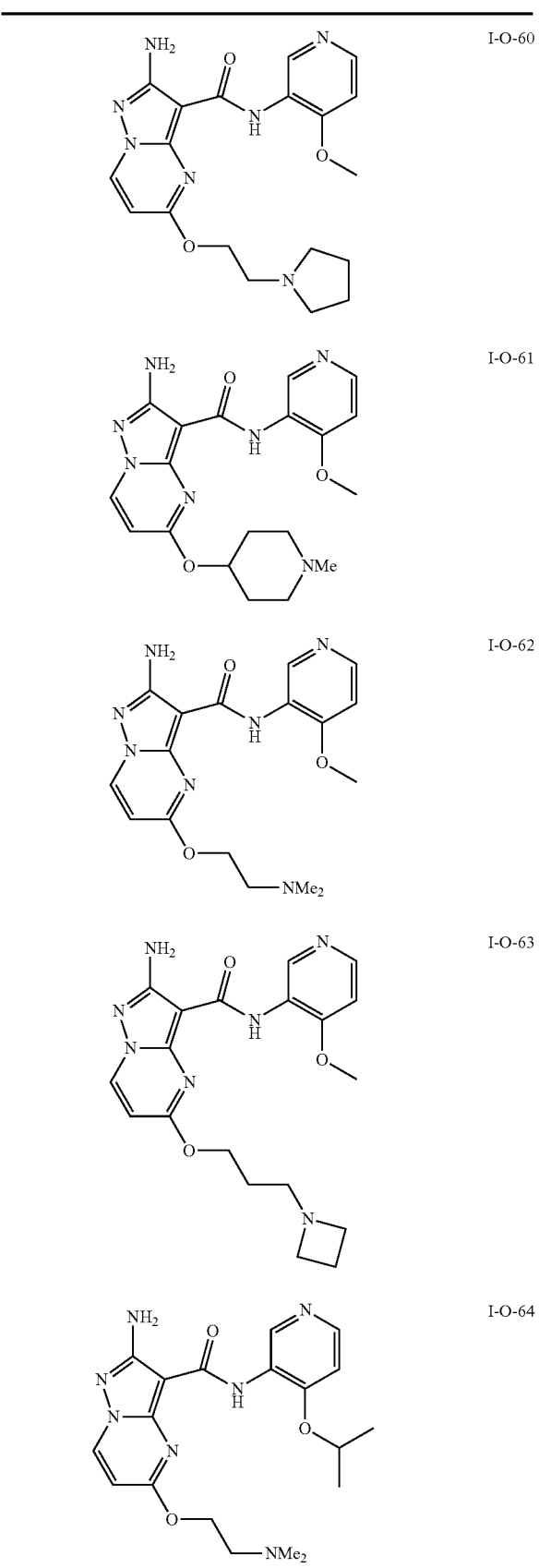
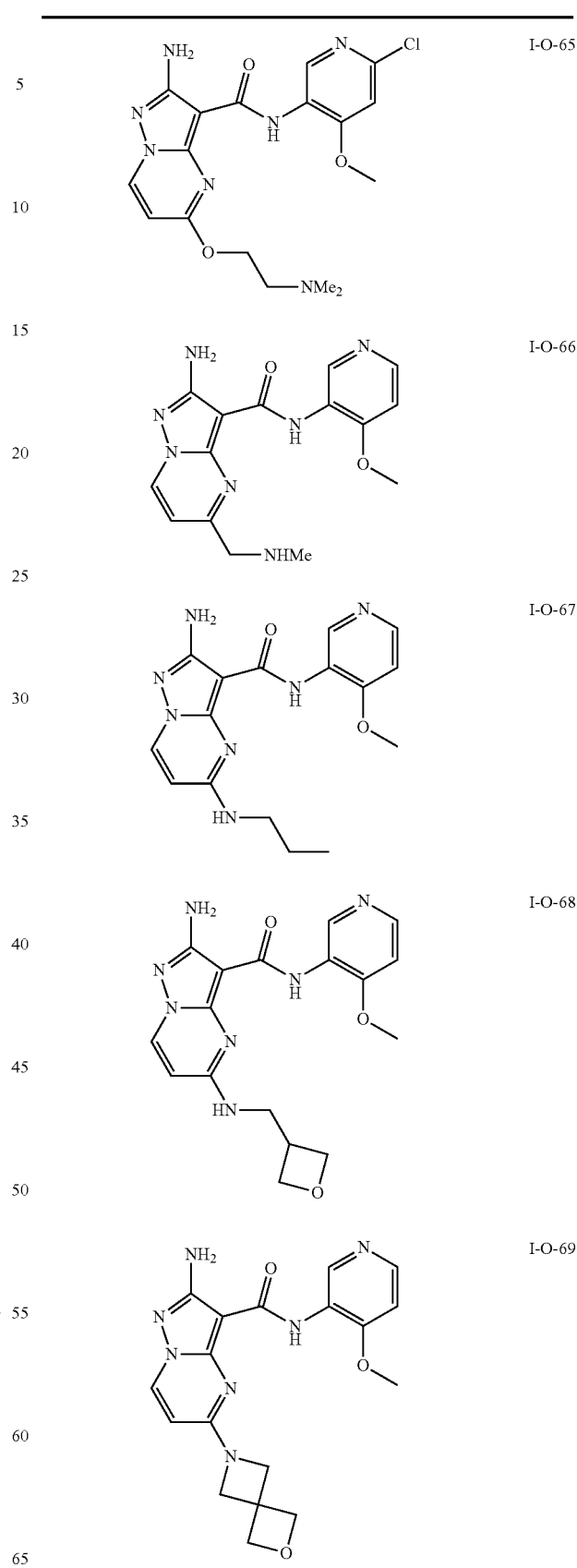

TABLE 1-continued
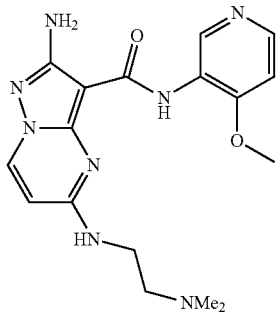 [SMILES: COc1ccncc1NC(=O)c1c(N)nn2ccc(NCCN(C)C)nc12] I-O-70
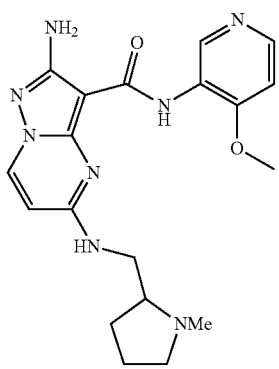 [SMILES: COc1ccncc1NC(=O)c1c(N)nn2ccc(NCC3CCCN3C)nc12] I-O-71
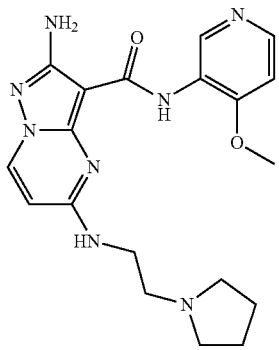 [SMILES: COc1ccncc1NC(=O)c1c(N)nn2ccc(NCCN3CCCC3)nc12] I-O-72
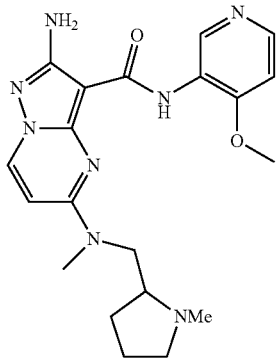 [SMILES: COc1ccncc1NC(=O)c1c(N)nn2ccc(N(C)CC3CCCN3C)nc12] I-O-73
TABLE 1-continued
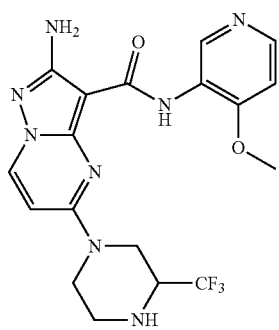 [SMILES: COc1ccncc1NC(=O)c1c(N)nn2ccc(N3CCNC(C(F)(F)F)C3)nc12] I-O-74
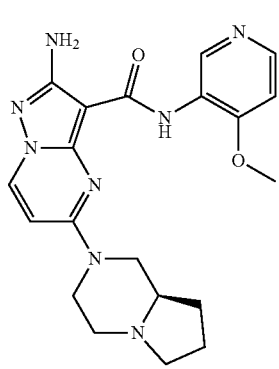 [SMILES: COc1ccncc1NC(=O)c1c(N)nn2ccc(N3CCN4CCC[C@@H]4C3)nc12] I-O-75
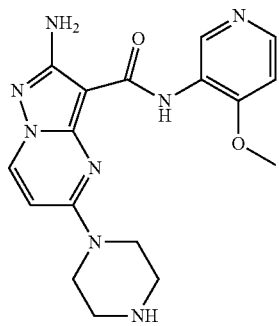 [SMILES: COc1ccncc1NC(=O)c1c(N)nn2ccc(N3CCNCC3)nc12] I-O-76
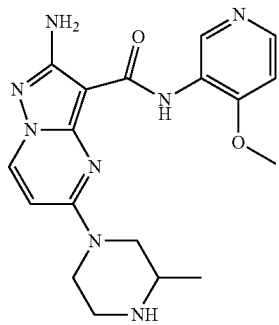 [SMILES: COc1ccncc1NC(=O)c1c(N)nn2ccc(N3CCNC(C)C3)nc12] I-O-77

TABLE 1-continued

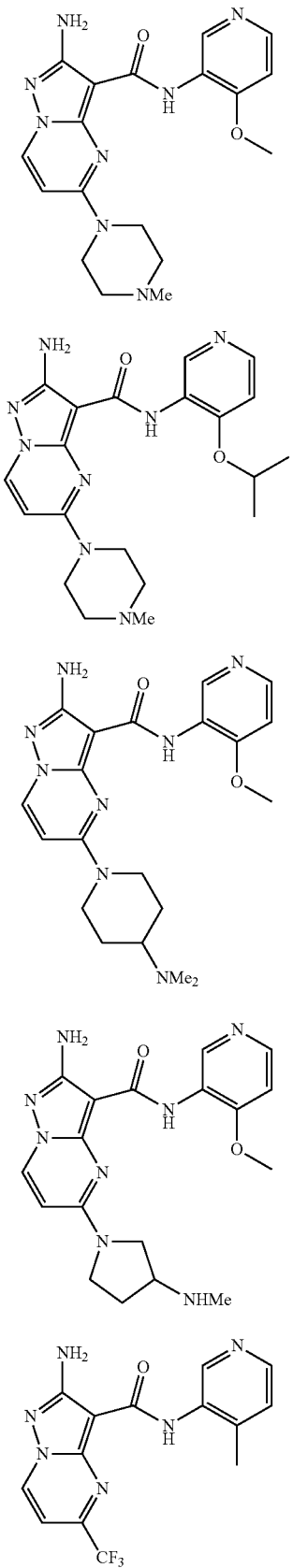

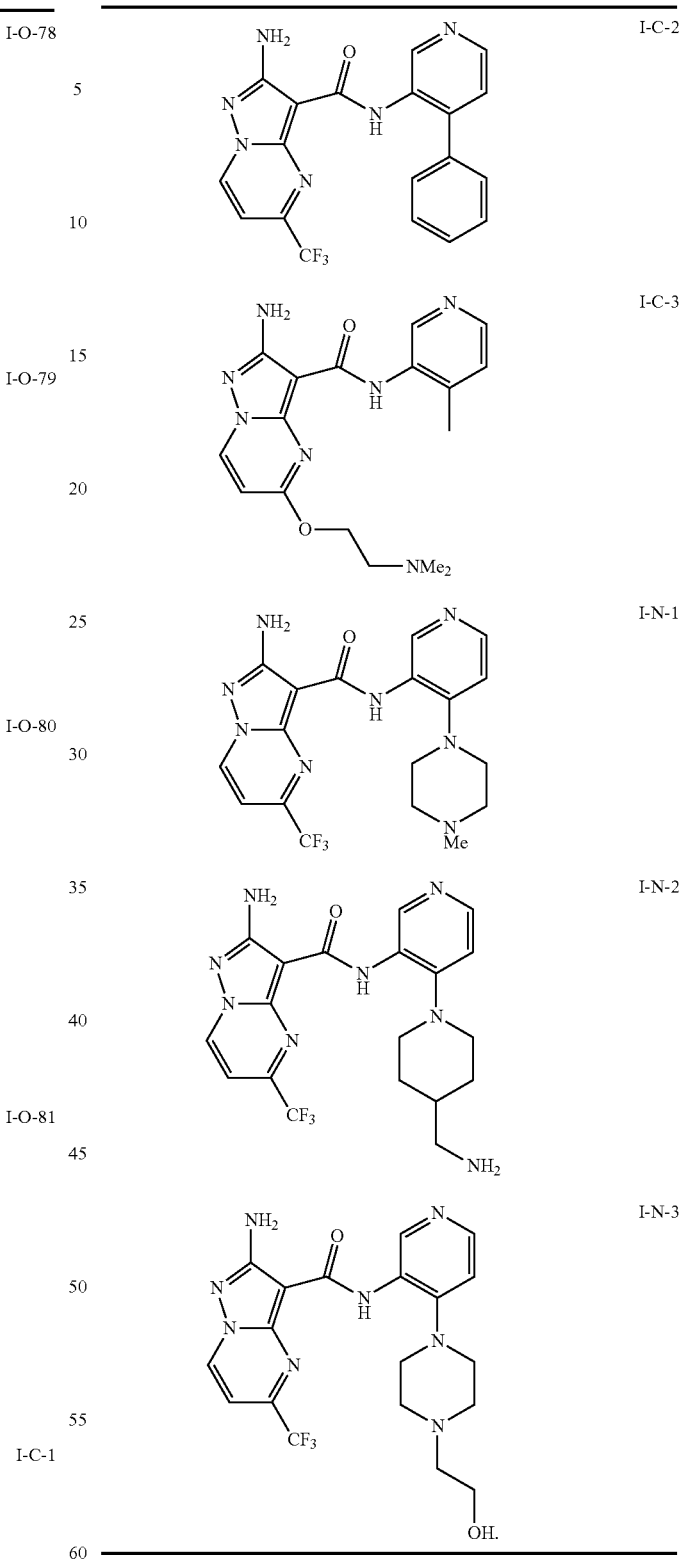

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, $J^A$ can be bonded to any position on the pyridyl ring. For bicyclic rings, a bond drawn through both rings indicates that the substituent can be bonded from any position of the bicyclic ring. In example ii below, for instance, $J^A$ can be bonded to the 5-membered ring (on the nitrogen atom, for instance), and to the 6-membered ring.

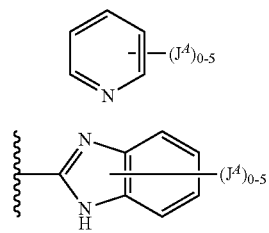

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "dative bond", as used herein, is defined as the coordination bond formed upon interaction between molecular species, one of which serves as a donor and the other as an acceptor of the electron pair to be shared in the complex formed.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —$CH_2$-cyclopropyl, $CH_2CH_2CH(CH_3)$-cyclohexyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —$CF_3$ and —$CF_2CF_3$.

The terms "halogen", "halo", and "hal" mean F, Cl, Br, or I.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroarylalkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

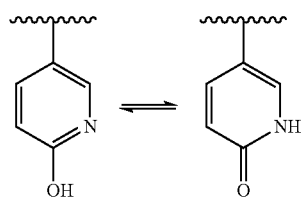 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference. Preferred oxygen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —$SO_2$—. These atoms or groups can be combined to form larger groups. Examples of such larger groups include, but are not limited to, —OC(O)—, —C(O)CO—, —$CO_2$—, —C(O)NR—, —C(=N—CN), —NRCO—, —NRC(O)O—, —$SO_2$NR—, —$NRSO_2$—, —NRC(O)NR—, —OC(O)NR—, and —$NRSO_2$NR—, wherein R is, for example, H or $C_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —$CH_2CH=N—CH_3$. In some cases, especially on the terminal end, an optional replacement can be bonded to the aliphatic group via a triple bond. One example of this would be $CH_2CH_2CH_2C\equiv N$. It should be understood that in this situation, the terminal nitrogen is not bonded to another atom.

It should also be understood that, the term "methylene unit" can also refer to branched or substituted methylene units. For example, in an isopropyl moiety [—$CH(CH_3)_2$], a nitrogen atom (e.g. NR) replacing the first recited "methylene unit" would result in dimethylamine [—$N(CH_3)_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a $C_3$ aliphatic can be optionally replaced by 2 nitrogen atoms to form —C—N≡N. The optional replacements can also completely replace all of the carbon atoms in a chain. For example, a $C_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —$CH_2CH_2CH_3$ were optionally replaced with —O—, the resulting compound could be —$OCH_2CH_3$, —$CH_2OCH_3$, or —$CH_2CH_2OH$. In another example, if a methylene unit of —$CH_2CH_2CH_3$ was optionally replaced with —NH—, the resulting compound could be —$NHCH_2CH_3$, —$CH_2NHCH_3$, or —$CH_2CH_2NH_2$. It should be understood that if the terminal atom does not contain any free valence electrons, then a hydrogen atom is not required at the terminal end (e.g., —$CH_2CH_2CH$=O or —$CH_2CH_2C$≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

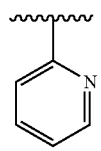

also represents

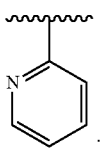

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester, or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

ABBREVIATIONS

The following abbreviations are used:
DMSO dimethyl sulfoxide
DCM dichloromethane
ATP adenosine triphosphate
$^1$HNMR proton nuclear magnetic resonance
HPLC high performance liquid chromatography
LCMS liquid chromatography-mass spectrometry
Rt retention time
RT room temperature
NMP N-methylpyrrolidone
TFA trifluoroacetic acid
Bp Boiling point
THF tetrahydrofuran
T3P Propylphosphonic anhydride
COMU 1-[(1-(Cyano-2-ethoxy-2-oxoethylideneaminooxy)-dimethylamino-morpholino)]uroniumhexafluorophosphate
TCTU [(6-chlorobenzotriazol-1-yl)oxy-(dimethylamino) methylene]-dimethyl-ammonium tetrafluoroborate
HBTU O-Benzotriazole-N,N,N',N'-tetramethyl-uronium-hexafluoro-phosphate
TBTU 2-(1H-benzotriazole-1-yl)-1,1,3,3-tetramethyluronium tetrafluoroborate
HBTU O-Benzotriazole-N,N,N',N'-tetramethyl-uronium-hexafluoro-phosphate
TBME tert-butyl methyl ether
DMF dimethylformamide
DIPEA N,N-diisopropylethylamine
EDCI 1-Ethyl-3-(3-dimethylaminopropyl)carbodiimide
Compound Uses One aspect of this invention provides compounds that are inhibitors of ATR kinase, and thus are useful for treating or lessening the severity of a disease, condition, or disorder in a subject or patient where ATR is implicated in the disease, condition, or disorder.

As used herein, the terms "subject" and "patient" are used interchangeably. The terms "subject" and "patient" refer to an animal, and more specifically a human. In one embodiment, the subject is a non-human animal such as a rat or dog. In a preferred embodiment, the subject is a human.

Another aspect of this invention provides compounds that are useful for the treatment of diseases, disorders, and conditions characterized by excessive or abnormal cell proliferation. Such diseases include a proliferative or hyperproliferative disease. Examples of proliferative and hyperproliferative diseases include, without limitation, cancer and myeloproliferative disorders.

In some embodiments, said compounds are selected from the group consisting of a compound of formula I. The term "cancer" includes, but is not limited to the following cancers. Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological/Female: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from a cancer of the lung or the pancreas. In other embodiments, the cancer is selected from lung cancer, head and neck cancer, pancreatic cancer, gastric cancer, or brain cancer. In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

Thus, the term "cancerous cell" as provided herein, includes a cell afflicted by any one of the above-identified conditions. In some embodiments, the cancer is selected from colorectal, thyroid, or breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Pharmaceutical Compositions

The present invention also provides compounds and compositions that are useful as inhibitors of ATR kinase.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound or a pharmaceutically acceptable salt thereof, and the additional therapeutic agent.

As used herein, the term "in combination" or "co-administration" can be used interchangeably to refer to the use of more than one therapy (e.g., one or more therapeutic agents). The use of the term does not restrict the order in which therapies (e.g., therapeutic agents) are administered to a subject.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensitizers. In yet other embodiments, said additional therapeutic agent is ionizing radiation.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used in combination with compounds of this invention include, but are not limited to Platinating agents, such as Carboplatin, Nedaplatin, Satraplatin and other derivatives; Topo I inhibitors, such as Topotecan, irinotecan/SN38, rubitecan and other derivatives; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mercaptopurine, 5-Fluorouracil (5FU) and relatives); Alkylating agents, such as Nitrogen mustards (Cyclophosphamide, Melphalan, Chlorambucil, mechlorethamine, Ifosfamide and relatives); nitrosoureas (e.g., Carmustine); Triazenes (Dacarbazine, temozolomide); Alkyl sulphonates (e.g., Busulfan); Procarbazine and Aziridines; Antibiotics, such as Hydroxyurea, Anthracyclines (doxorubicin, daunorubicin, epirubicin and other derivatives); Anthracenediones (Mitoxantrone and relatives); Streptomyces family (Bleomycin, Mitomycin C, actinomycin); and Ultraviolet light.

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); mechlorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Compositions for Administration into a Subject

The ATR kinase inhibitors or pharmaceutical salts thereof may be formulated into pharmaceutical compositions for administration to animals or humans. These pharmaceutical compositions, which comprise an amount of the ATR inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the disorder, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Combination Therapies" section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per dose, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/dose of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent

Depending upon the particular protein kinase-mediated conditions to be treated or prevented, additional drugs, which are normally administered to treat or prevent that condition, may be administered together with the compounds of this invention.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from Platinating agents, such as Cisplatin, Oxaliplatin, Carboplatin, Nedaplatin, or Satraplatin and other derivatives; Topo I inhibitors, such as Camptothecin, Topotecan, irinotecan/SN38, rubitecan and other derivatives; Antimetabolites, such as Folic family (Methotrexate, Pemetrexed and relatives); Purine family (Thioguanine, Fludarabine, Cladribine, 6-Mercaptopurine and relatives); Pyrimidine family (Cytarabine, Gemcitabine, 5-Fluorouracil and relatives); Alkylating agents, such as Nitrogen mustards (Cyclophosphamide, Melphalan, Chlorambucil, mechlorethamine, Ifosfamide, and relatives); nitrosoureas (e.g. Carmustine); Triazenes (Dacarbazine, temozolomide); Alkyl sulphonates (e.g. Busulfan); Procarbazine and Aziridines; Antibiotics, such as Hydroxyurea; Anthracyclines (doxorubicin, daunorubicin, epirubicin and other derivatives); Anthracenediones (Mitoxantrone and relatives); *Streptomyces* family (Bleomycin, Mitomycin C, actinomycin) and Ultraviolet light.

Another embodiment provides administering a compound of this invention with an additional therapeutic agent that inhibits or modulates a base excision repair protein. In some embodiments, the base excision repair protein is selected from UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin. In other embodiments, the base excision repair protein is selected from PARP1, PARP2, or PolB. In yet other embodiments, the base excision repair protein is selected from PARP1 or PARP2. In some embodiments, the agent is selected from Olaparib (also known as AZD2281 or KU-0059436), Iniparib (also known as BSI-201 or SAR240550), Veliparib (also known as ABT-888), Rucaparib (also known as PF-01367338), CEP-9722, INO-1001, MK-4827, E7016, BMN673, or AZD2461.

Biological Samples

As inhibitors of ATR kinase, the compounds and compositions of this invention are also useful in biological samples. One aspect of the invention relates to inhibiting ATR kinase activity in a biological sample, which method comprises contacting said biological sample with a compound described herein or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. The term "compounds described herein" includes compounds of formula I.

Inhibition of ATR kinase activity in a biological sample is useful for a variety of purposes that are known to one of skill in the art. Examples of such purposes include, but are not limited to, blood transfusion, organ-transplantation, and biological specimen storage.

Study of Protein Kinases

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of ATR is set forth in the Examples below.

Another aspect of the invention provides a method for modulating enzyme activity by contacting a compound described herein with ATR kinase.

Methods of Treatment

In one aspect, the present invention provides a method for treating or lessening the severity of a disease, condition, or disorder where ATR kinase is implicated in the disease state. In another aspect, the present invention provides a method for treating or lessening the severity of an ATR kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the ATR kinase. Another aspect provides a method for treating or lessening the severity of a kinase disease, condition, or disorder by inhibiting enzymatic activity of ATR kinase with an ATR kinase inhibitor. One aspect of the invention relates to a method of inhibiting ATR kinase activity in a patient, which method comprises administering to the patient a compound described herein, or a composition comprising said compound. In some embodiments, said method is used to treat or prevent a condition selected from proliferative and hyperproliferative diseases, such as cancer.

Another aspect of this invention provides a method for treating, preventing, or lessening the severity of proliferative or hyperproliferative diseases comprising administering an effective amount of a compound, or a pharmaceutically acceptable composition comprising a compound, to a subject in need thereof. In some embodiments, said method is used to treat or prevent cancer. In some embodiments, said method is used to treat or prevent a type of cancer with solid tumors. In yet another embodiment, said cancer is selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological/Female: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from the cancers described herein. In some embodiments, said cancer is lung cancer, head and neck cancer, pancreatic cancer, gastric cancer, or brain cancer. In other embodiments, the cancer is selected from a cancer of the lung or the pancreas.

In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting ATR in a patient comprising administering a compound described herein as described herein. Another embodiment provides a method of treating cancer comprising administering to a patient a compound described herein, wherein the variables are as defined herein.

Some embodiments comprising administering to said patient an additional therapeutic agent selected from a DNA-damaging agent; wherein said additional therapeutic agent is appropriate for the disease being treated; and said additional therapeutic agent is administered together with said compound as a single dosage form or separately from said compound as part of a multiple dosage form.

In some embodiments, said DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, said DNA-damaging agent is selected from ionizing radiation, a platinating agent, a Topo I inhibitor, a Topo II inhibitor, or an antibiotic.

Examples of Platinating agents include Cisplatin, Oxaliplatin, Carboplatin, Nedaplatin, Satraplatin and other derivatives. Other platinating agents include Lobaplatin, and Triplatin. Other platinating agents include Tetranitrate, Picoplatin, Satraplatin, ProLindac and Aroplatin.

Examples of Topo I inhibitor include Camptothecin, Topotecan, irinotecan/SN38, rubitecan and other derivatives. Other Topo I inhibitors include Belotecan.

Examples of Topo II inhibitors include Etoposide, Daunorubicin, Doxorubicin, Aclarubicin, Epirubicin, Idarubicin, Amrubicin, Pirarubicin, Valrubicin, Zorubicin and Teniposide.

Examples of Antimetabolites include members of the Folic family, Purine family (purine antagonists), or Pyrimidine family (pyrimidine antagonists). Examples of the Folic family include methotrexate, pemetrexed and relatives; examples of the Purine family include Thioguanine, Fludarabine, Cladribine, 6-Mercaptopurine, and relatives; examples of the Pyrimidine family include Cytarabine, gemcitabine, 5-Fluorouracil (5FU) and relatives.

Some other specific examples of antimetabolites include Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea.

Examples of alkylating agents include Nitrogen mustards, Triazenes, alkyl sulphonates, Procarbazine and Aziridines. Examples of Nitrogen mustards include Cyclophosphamide, Melphalan, Chlorambucil and relatives; examples of nitrosoureas include Carmustine; examples of triazenes include Dacarbazine and temozolomide; examples of alkyl sulphonates include Busulfan.

Other specific examples of alkylating agents include Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

Examples of antibiotics include Mitomycin, Hydroxyurea; Anthracyclines, Anthracenediones, *Streptomyces* family. Examples of Anthracyclines include doxorubicin, daunorubicin, epirubicin and other derivatives; examples of Anthracenediones include Mitoxantrone and relatives; examples of *Streptomyces* family include Bleomycin, Mitomycin C, and actinomycin.

In certain embodiments, said platinating agent is Cisplatin or Oxaliplatin; said Topo I inhibitor is Camptothecin; said Topo II inhibitor is Etoposide; and said antibiotic is Mitomycin. In other embodiments, said platinating agent is selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from a member of the Folic Family, the Purine Family, or the Pyrimidine Family; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or *Streptomyces* family.

In some embodiments, the additional therapeutic agent is ionizing radiation. In other embodiments, the additional therapeutic agent is Cisplatin or Carboplatin. In yet other embodiments, the additional therapeutic agent is Etoposide. In yet other embodiments, the additional therapeutic agent is Temozolomide.

In certain embodiments, the additional therapeutic agent is selected from one or more of the following: Cisplatin, Carboplatin, gemcitabine, Etoposide, Temozolomide, or ionizing radiation.

Another embodiment provides methods for treating pancreatic cancer by administering a compound described herein in combination with another known pancreatic cancer treatment. One aspect of the invention includes administering a compound described herein in combination with gemcitabine. In some embodiments, the pancreatic cancer comprises one of the following cell lines: PSN-1, MiaPaCa-2 or Panc-1. According to another aspect, the cancer comprises one of the following primary tumor lines: Panc-M or MRCS.

Another aspect of the invention includes administering a compound described herein in combination with radiation therapy. Yet another aspect provides a method of abolishing radiation-induced G2/M checkpoint by administering a compound described herein in combination with radiation treatment.

Another aspect provides a method of treating pancreatic cancer by administering to pancreatic cancer cells a compound described herein in combination with one or more cancer therapies. In some embodiments, the compound is combined with chemoradiation, chemotherapy, and/or radiation therapy. As would be understood by one of skill in the art, chemoradiation refers to a treatment regime that includes both chemotherapy (such as gemcitabine) and radiation. In some embodiments, the chemotherapy is gemcitabine.

Yet another aspect provides a method of increasing the sensitivity of pancreatic cancer cells to a cancer therapy selected from gemcitabine or radiation therapy by administering a compound described herein in combination with the cancer therapy.

In some embodiments, the cancer therapy is gemcitabine. In other embodiments, the cancer therapy is radiation therapy. In yet another embodiment the cancer therapy is chemoradiation.

Another aspect provides a method of inhibiting phosphorylation of Chk1 (Ser 345) in a pancreatic cancer cell comprising administering a compound described herein after treatment with gemcitabine (100 nM) and/or radiation (6 Gy) to a pancreatic cancer cell.

Another aspect provides method of radiosensitizing hypoxic PSN-1, MiaPaCa-2 or PancM tumor cells by administering a compound described herein to the tumor cell in combination with radiation therapy.

Yet another aspect provides a method of sensitizing hypoxic PSN-1, MiaPaCa-2 or PancM tumor cells by administering a compound described herein to the tumor cell in combination with gemcitabine.

Another aspect provides a method of sensitizing PSN-1 and MiaPaCa-2 tumor cells to chemoradiation by administering a compound described herein to the tumor cells in combination with chemoradiation.

Another aspect provides a method of disrupting damage-induced cell cycle checkpoints by administering a compound described herein in combination with radiation therapy to a pancreatic cancer cell.

Another aspect provides a method of inhibiting repair of DNA damage by homologous recombination in a pancreatic cancer cell by administering a compound described herein in combination with one or more of the following treatments: chemoradiation, chemotherapy, and radiation therapy.

In some embodiments, the chemotherapy is gemcitabine.

Another aspect provides a method of inhibiting repair of DNA damage by homologous recombination in a pancreatic cancer cell by administering a compound described herein in combination with gemcitabine and radiation therapy.

In some embodiments, the pancreatic cancer cells are derived from a pancreatic cell line selected from PSN-1, MiaPaCa-2 or Panc-1.

In other embodiments, the pancreatic cancer cells are in a cancer patient.

Another aspect of the invention provides a method of treating non-small cell lung cancer comprising administering to a patient a compound described herein in combination with one or more of the following additional therapeutic agents: Cisplatin or Carboplatin, Etoposide, and ionizing radiation. Some embodiments comprise administering to a patient a compound described herein in combination with Cisplatin or Carboplatin, Etoposide, and ionizing radiation. In some embodiments the combination is Cisplatin, Etoposide, and ionizing radiation. In other embodiments the combination is Carboplatin, Etoposide, and ionizing radiation.

Another embodiment provides a method of promoting cell death in cancer cells comprising administering to a patient a compound described herein, or a composition comprising said compound.

Yet another embodiment provides a method of preventing cell repair of DNA damage in cancer cells comprising administering to a patient a compound described herein, or a composition comprising said compound. Yet another embodiment provides a method of preventing cell repair caused by of DNA damage in cancer cells comprising administering to a patient a compound of formula I, or composition comprising said compound.

Another embodiment provides a method of sensitizing cells to DNA damaging agents comprising administering to a patient a compound described herein, or a composition comprising said compound.

In some embodiments, the method is used on a cancer cell having defects in the ATM signaling cascade. In some embodiments, said defect is altered expression or activity of one or more of the following: ATM, p53, CHK2, MRE11, RAD50, NBS1, 53BP1, MDC1, H2AX, MCPH1/BRIT1, CTIP, or SMC1. In other embodiments, said defect is altered expression or activity of one or more of the following: ATM, p53, CHK2, MRE11, RAD50, NBS1, 53BP1, MDC1 or H2AX. According to another embodiment, the method is used on a cancer, cancer cell, or cell expressing DNA damaging oncogenes.

In another embodiment, the cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

According to another embodiment, the method is used on a cancer, cancer cell, or cell has a defect in a protein involved in base excision repair ("base excision repair protein"). There are many methods known in the art for determining whether a tumor has a defect in base excision repair. For example, sequencing of either the genomic DNA or mRNA products of each base excision repair gene (e.g., UNG, PARP1, or LIG1) can be performed on a sample of the tumor to establish whether mutations expected to modulate the function or expression of the gene product are present (Wang et al., Cancer Research 52:4824 (1992)). In addition to the mutational inactivation, tumor cells can modulate a DNA repair gene by hypermethylating its promoter region, leading to reduced gene expression. This is most commonly assessed using methylation-specific polymerase chain reaction (PCR) to quantify methylation levels on the promoters of base excision repair genes of interest. Analysis of base excision repair gene promoter methylation is available commercially (http://www.sabiosciences.com/dna_methylation_product/HTML/MEAH-421A.html).

Finally, the expression levels of base excision repair genes can be assessed by directly quantifying levels of the mRNA and protein products of each gene using standard techniques such as quantitative reverse transcriptase-coupled polymerase chain reaction (RT-PCR) and immunhohistochemistry (IHC), respectively (Shinmura et al., Carcinogenesis 25: 2311 (2004); Shinmura et al., Journal of Pathology 225:414 (2011)).

In some embodiments, the base excision repair protein is UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin.

In some embodiments, the base excision repair protein is PARP1, PARP2, or PolB. In other embodiments, the base excision repair protein is PARP1 or PARP2.

The methods described above (gene sequence, promoter methylation and mRNA expression) may also be used to characterize the status (e.g., expression or mutation) of other genes or proteins of interesting, such DNA-damaging oncogenes expressed by a tumor or defects in the ATM signaling cascade of a cell.

Yet another embodiment provides use of a compound described herein as a radio-sensitizer or a chemo-sensitizer.

Yet other embodiment provides use of a compound of formula I as a single agent (monotherapy) for treating cancer. In some embodiments, the compounds of formula I are used for treating patients having cancer with a DNA-damage response (DDR) defect. In other embodiments, said defect is a mutation or loss of ATM, p53, CHK2, MRE11, RAD50, NBS1, 53BP1, MDC1, or H2AX.

Compounds and Compositions for Use

One embodiment provides a compound or composition as described herein for use as a radio-sensitizer or a chemo-sensitizer. Another embodiment provides a compound or composition as described herein for use as a single agent (monotherapy) for treating cancer.

Another embodiment provides a compound or composition as described herein for treating patients having cancer with a DNA-damage response (DDR) defect. In some embodiments, said defect is a mutation or loss of ATM, p53, CHK2, MRE11, RAD50, NBS1, 53BP1, MDC1, or H2AX. In other embodiments, said defect is a mutation or loss of ATM, p53, CHK2, MRE11, RAD50, NBS1, 53BP1, MDC1, H2AX, MCPH1/BRIT1, CTIP, or SMC1.

Another embodiment provides compounds or compositions described herein for treating cancer. In some embodiments, the compound or composition is further combined with an additional therapeutic agent described herein. In some embodiments, the compound or composition is further combined with a DNA damaging agent described herein.

In some embodiments, the cancer has a defect in a pathway described herein.

Manufacture of Medicaments

One embodiment provides the use of a compound or composition described herein for the manufacture of a medicament for use as a radio-sensitizer or a chemo-sensitizer. Another embodiment provides the use of a compound or composition described herein for the manufacture of a medicament for the manufacture of a medicament for use as a single agent (monotherapy) for treating cancer.

Yet another embodiment provides the use of a compound or composition described herein for the manufacture of a medicament for the manufacture of a medicament for treating patients having cancer with a DNA-damage response (DDR) defect.

In some embodiments, said defect is a mutation or loss of ATM, p53, CHK2, MRE11, RAD50, NBS1, 53BP1, MDC1, or H2AX. In other embodiments, said defect is a mutation or loss of ATM, p53, CHK2, MRE11, RAD50, NBS1, 53BP1, MDC1, H2AX, MCPH1/BRIT1, CTIP, or SMC1.

Another embodiment provides the use of a compound or composition described herein for the manufacture of a medicament for treating cancer. In some embodiments, the compound or composition is combined with an additional therapeutic agent, such as a DNA damaging agent, described herein. In another embodiment, the cancer has a defect in a pathway described herein.

Experimental Materials and Methods

All commercially available solvents and reagents were used as received. Microwave reactions were carried out using a CEM Discovery microwave. Flash chromatography was carried out on an ISCO© Combiflash® Companion™ system eluting with a 0 to 100% EtOAc/petroleum ether gradient. Other methods known in the art were also utilized to perform Flash Chromotography. Samples were applied pre-absorbed on silica. Where stated, supercritical fluid chromatography (SFC) was performed on a Berger Minigram SFC machine. All $^1$H NMR spectra were recorded using a Bruker Avance III 500 instrument at 500 MHz. MS samples were analyzed on a Waters SQD mass spectrometer with electrospray ionization operating in positive and negative ion mode. Samples were introduced into the mass spectrometer using chromatography. All final products had a purity ≥95%, unless specified otherwise in the experimental details. HPLC purity was measured on a Waters Acquity UPLC system with a Waters SQD MS instrument equipped with a Waters UPLC BEH C8 1.7 μm, 2.1×50 mm column and a Vanguard BEH C8 1.7 μm, 2.1×5 mm guard column.

As used herein, the term "Rt(min)" refers to the HPLC retention time, in minutes, associated with the compound. Unless otherwise indicated, the HPLC methods utilized to obtain the reported retention times are as described below:

HPLC Method
Instrument: Waters Acquity UPLC-MS;
Column: Waters UPLC BEH C8 1.7 μm, 2.1×50 mm with Vanguard BEH C8 1.7 μm, 2.1×5 mm guard column;
Column temperature: 45° C.;
Mobile Phase A: 10 mM ammonium formate in water:acetonitrile 95:5, pH 9;
Mobile Phase B: acetonitrile;
Detection: 210-400 nm;
Gradient: 0-0.40 min: 2% B, 0.40-4.85 min: 2% B to 98% B, 4.85-4.90 min: 98% B to 2% B, 4.90-5.00 min: hold at 2% B;
Flow rate: 0.6 mL/minute.

EXAMPLES AND SCHEMES

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance). The following generic schemes and examples illustrate how to prepare the compounds of the present disclosure. The examples are for the purpose of illustration only and are not to be construed as limiting the scope of the invention in any way.

Scheme 1: General approach for the preparation of compounds of formula I

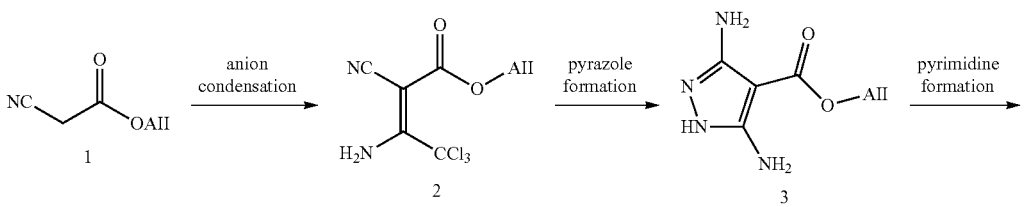

-continued

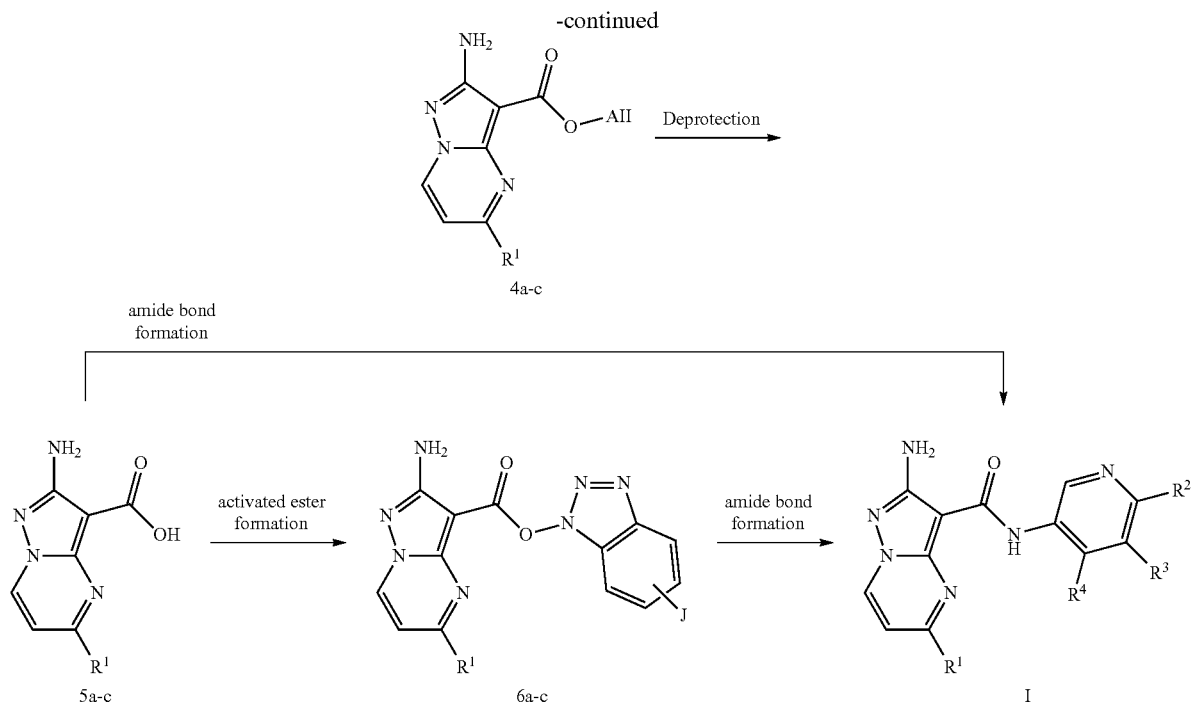

Compounds of this invention can be synthesised according to methods similar to the one depicted in Scheme 1.

The anion of commercially available allyl cyanoacetate 1 can react with trichloroacetonitrile to provide intermediate 2. In the anion condensation step, the anion of commercially available allyl cyanoacetate 1 can be generated with a base such as potassium acetate in an appropriate solvent such as an alcohol (e.g., isopropylalcohol). The anion then reacts with trichloroacetonitrile at room temperature.

In the pyrazole formation step, intermediate 2 is reacted with hydrazine (or its hydrate) in an aprotic solvent, such as DMF, to provide the diaminopyrazole 3. The reaction occurs under basic conditions (e.g., in the presence of potassium acetate or AcONa) with heating (e.g., 110° C.) to ensure complete cyclisation. Intermediate 3 can further be condensed with a dielectrophilic coupling partner to form the pyrimidine 4a-c.

In the pyrimidine formation step, intermediate 3 is reacted with a 1,3-dielectrophilic species (e.g., methyl prop-2-ynoate) in various types of solvents (e.g., DMF, or DMSO/water) to furnish the bicyclic cores 4a-c. In some instances, the reaction is carried out in the presence of a strong base, e.g., KOH. When one or two of the electrophilic centers is protected/masked (e.g., 3-(1,3-dioxolan-2-yl)-1,1,1-trifluoropropan-2-one), introduction of a sulfonic acid (e.g., PTSA) may be required to liberate the reactive functional group.

Deprotection, e.g., via hydrolysis, of the allyl ester leads to the carboxylic acids 5a-c. In the deprotection step, compounds 4a-c are subjected to hydrolytic conditions that are known to those skilled in the art. For example, treatment of 4a-c with phenylsilane or methylbenzenesulfinate in the presence of a catalytic amount of palladium (e.g., $Pd(PPh_3)_4$) leads to the formation of the corresponding carboxylic acid 5. Alternatively, compounds 4a-c could be treated with aqueous alkali (e.g., NaOH or KOH) to produce acids 5a-c.

In the activated ester formation step, the carboxylic acids 5a-c are reacted with amide coupling agents known to those skilled in the art. When the coupling agent is chosen appropriately, the reactions can proceed rapidly (~1 h) at room temperature in the presence of an organic base (e.g., triethylamine or DIPEA) to provide the activated esters 6a-c. For example, when the amide coupling agents TBTU [J=H] or TCTU [J=Cl] are used, compounds 6a-c are obtained readily by filtration of the reaction mixture.

Formation of the activated esters 6a-c prior to the amide bond formation to prepare compounds of formula I is sometimes preferred, although a direct conversion of 5a-c into the compounds of formula I of this invention is also possible. Alternative activated esters can also be utilised (isolated or formed in situ) and will be known to those skilled in the art (e.g., using TCTU, HATU, T3P, COMU coupling agents).

In the amide bond formation step, activated esters 6a-c can react with a substituted 3-aminopyridine to provide compounds of formula I of this invention. The reaction conditions for the amide coupling are generally in an aprotic solvent (e.g., NMP, pyridine, DMF, etc) with heating (e.g., ≥90° C.).

Alternatively, the two steps described above can be combined: carboxylic acids 5 can be used as starting points for the amide bond formation, the activated esters being generated in situ, using the same amide couplings agents as those described above. Compounds of formula I of this invention are isolated in a similar manner to the one described above.

Scheme 2: Alternative approach for the preparation of compounds of formula I

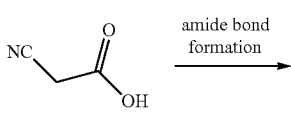

7

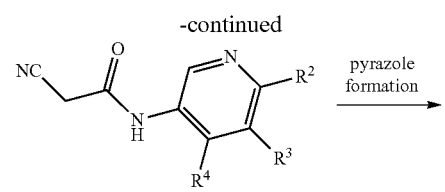

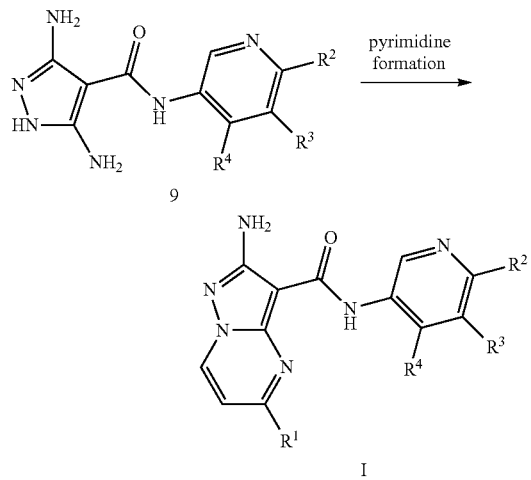

Alternatively, compounds of the present disclosure can be prepared according to methods similar to the one depicted in Scheme 2.

The amide 8 can readily be prepared from commercially available cyanoacetic acid 7. In the amide bond formation step, cyanoacetic acid 7 can react with a substituted 3-aminopyridine to provide compounds 8 of this invention. The reaction conditions for the amide coupling are generally in an aprotic solvent (e.g., DCM, NMP, DMF, etc), in the presence of an organic base such as an aliphatic amine (e.g., triethylamine or DIPEA) and an amide coupling agent known to those skilled in the art: for example EDCI, TBTU, COMU, T3P, etc.

In the pyrazole formation step, the anion of cyanoamide 8 can be generated with a base (such as potassium or sodium acetate) in an appropriate solvent such as an alcohol (e.g., ethanol). The anion then reacts with trichloroacetonitrile at room temperature (specific details are given in Examples below). The resulting solid, which can be collected by filtration, is then reacted with hydrazine (or its hydrate) in an aprotic solvent, such as DMF or NMP, to provide the diaminopyrazole 9.

Intermediate 9 is further condensed with a dielectrophilic coupling partner to form the pyrimidine portion of the compounds of formula I of this invention. In the pyrimidine formation step, intermediate 9 is reacted with an optionally protected 1,3-dielectrophilic species (e.g., 3-(1,3-dioxolan-2-yl)-1,1,1-trifluoropropan-2-one) in various types of solvents (e.g., iPrOH/water, DMF, or DMSO/water) to furnish the desired products of formula I. When one or two of the electrophilic centers is protected (e.g., aldehyde protected as a ketal), introduction of a sulfonic acid (e.g., PTSA) is required to liberate the reactive functional group.

Preparation 1: Allyl 3,5-diamino-1H-pyrazole-4-carboxylate 3

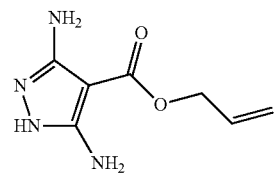

Step 1: allyl 3-amino-4,4,4-trichloro-2-cyanobut-2-enoate 2

To a solution of KOAc (589.4 g, 6.006 mol) in isopropanol (3 L) was added allyl cyanoacetate (429.4 g, 403.2 mL, 3.432 mol) and the reaction mixture was cooled to 5° C. Trichloroacetonitrile (495.5 g, 3.432 mol) was added in 50 mL portions, maintaining temperature below 15° C. The reaction mixture was then allowed to warm to 20° C. and stirred for 3 h. Water (~4 L) was added to dissolve the inorganic materials and precipitate out the desired product. The mixture was stirred for 20 minutes and the solid was isolated by filtration under vacuum. This solid was filtered, washed with water (2×0.5 L) and dried in a vacuum oven overnight at 40° C. to afford allyl 3-amino-4,4,4-trichloro-2-cyanobut-2-enoate 2 as an off-white powder (787 g, 85%). $^1$H NMR (500 MHz, CDCl$_3$) δ 10.17 (br s, 1H), 6.97 (m, 1H), 5.99 (m, 1H), 5.44 (m, 1H), 5.31 (m, 1H), 4.76 (m, 2H).

Step 2: Allyl 3,5-diamino-1H-pyrazole-4-carboxylate 3

To a suspension of allyl 3-amino-4,4,4-trichloro-2-cyanobut-2-enoate 2 (619 g, 2.297 mol) and KOAc (676.3 g, 6.891 mol) in DMF (2.476 L) at 0° C. was slowly added hydrazine hydrate (172.5 g, 167.6 mL, 3.446 mol) over 15 min. The reaction mixture was then stirred at ambient temperature for 2 h, at which stage $^1$H NMR shows complete consumption of the starting material. Reaction mixture was then heated overnight at 110° C. before being allowed to cool to ambient and stirred for another 48 h. The mixture was filtered through a sintered glass funnel to remove the precipitated solid and the filtrate was evaporated under reduced pressure to give a thick liquid. DCM (approx 2 L) was added, and the mixture filtered again to remove additional solids that have precipitated. The filtrate was purified through a 1 kg silica gel plug (gradient of DCM/MeOH as an eluent), and the solvent was removed to afford an orange solid which was suspended in acetonitrile and heated at about 70° C. until all the solid went into solution, at which point the solution was allowed to cool to ambient temperature, then to 2° C. The precipitate that formed was isolated by filtration under vacuum, washed with chilled MeCN (~50 mL) and dried to constant mass in a vacuum oven to furnish the title compound as an off-white powder (171.2 g, 41%). LC-MS (M+H)+ 183.0; ¹H NMR (300 MHz, DMSO) δ 10.60 (br s, 1H), 5.95-6.05 (m, 1H), 5.17-5.40 (m, 6H), 4.60 (d, 2H).

Preparation 2: 2-amino-5-(trifluoromethyl)pyrazolo[1,5-a]pyrimidine-3-carboxylic acid 5a

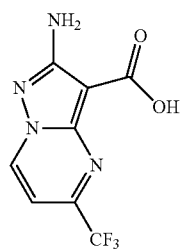

5a

Step 1: 3-(1,3-dioxolan-2-yl)-1,1,1-trifluoropropan-2-one

4-Methylbenzenesulfonic acid monohydrate (500.1 mg, 467.4 µL, 2.629 mmol) was added to a solution of 4-ethoxy-1,1,1-trifluoro-but-3-en-2-one (200.97 g, 1.195 mol) and ethylene glycol (77.27 g, 69.42 mL, 1.245 mol) in toluene (502.5 mL). The reaction mixture was heated to reflux for 90 min (oil bath). Then, the reflux was continued with simultaneous distillation of ethanol/toluene. The Dean-Stark was removed and the flask was connected to a distillation apparatus. 3-(1,3-Dioxolan-2-yl)-1,1,1-trifluoro-propan-2-one was distilled using a KNF pump (Bp 81° C.) as a light yellow oil (148 g, 67% yield). ¹H NMR (500 MHz, CDCl₃) δ 5.38-5.40 (t, 1H), 4.02-4.05 (m, 2H), 3.93-3.95 (m, 2H), 3.10 (d, 2H).

Step 2: allyl 2-amino-5-(trifluoromethyl)pyrazolo[1,5-a]pyrimidine-3-carboxylate 4a 3-(1,3-Dioxolan-2-yl)-1,1,1-trifluoro-propan-2-one (55.58 g, 301.9 mmol) and allyl 3,5-diamino-1H-pyrazole-4-carboxylate 3 (55 g, 301.9 mmol) were dissolved in 1,4-dioxane (330 mL). KOH (1.694 g, 30.19 mmol) was added and the yellow suspension was stirred at room temperature for 4 h30 min. The reaction mixture was heated at 90° C. for 16 h. The mixture was cooled down to room temperature. The reaction mixture was concentrated and purified by column chromatography (CombiFlash Companion XL, 1.5 kg column, 0.5 to 40% EtOAc in DCM) to afford allyl 2-amino-5-(trifluoromethyl)pyrazolo[1,5-a]pyrimidine-3-carboxylate 4a as a bright yellow solid (68 g, 79% yield). LC-MS (M+H)+ 287.2; ¹H NMR (500 MHz, DMSO-d6) δ 9.18 (m, 1H), 7.46 (m, 1H), 6.77 (s, 2H), 6.05 (m, 1H), 5.62 (m, 1H), 5.26 (m, 1H), 4.78 (m, 2H).

Step 3: 2-amino-5-(trifluoromethyl)pyrazolo[1,5-a]pyrimidine-3-carboxylic acid 5a Allyl 2-amino-5-(trifluoromethyl)pyrazolo[1,5-a]pyrimidine-3-carboxylate 4a (67.45 g, 235.7 mmol) in dioxane (670 mL)/water (670 mL) was treated with lithium hydroxide (16.93 g, 707.1 mmol). The resulting light brown suspension was stirred at 70° C. for 1 h45 min. The bright yellow suspension was cooled down to ambient temperature and concentrated in vacuo. The crude mixture was cooled down in a water bath containing ice (T°~10° C.) and the pH was adjusted to ~3 with 2M HCl. The mixture was stirred for 2 h and the yellow solid was filtered, washed with water and dried on the sinter to give 63.6 g of a wet yellow solid. The solid was dried overnight in a vacuum oven at 40° C. (KNF pump) to afford 2-amino-5-(trifluoromethyl)pyrazolo[1,5-a]pyrimidine-3-carboxylic acid 5a as a yellow solid (55.2 g, 95% yield). LC-MS (M+H)+ 247.0; ¹H NMR (500 MHz, DMSO-d6) δ 12.5 (br s, 1H), 9.10 (d, 1H), 7.34 (d, 1H), 6.75 (s, 2H).

Alternatively, 2-amino-5-(trifluoromethyl)pyrazolo[1,5-a]pyrimidine-3-carboxylic acid 5a can be prepared as follows:

Allyl 2-amino-5-(trifluoromethyl)pyrazolo[1,5-a]pyrimidine-3-carboxylate 4a (240 mg, 0.8385 mmol) and phenylsilane (181.5 mg, 206.7 µL, 1.677 mmol) were dissolved in dry DCM (6 mL). Pd(PPh₃)₄ (38.76 mg, 0.03354 mmol) was added and the resulting solution was stirred at RT for 2 hrs. The suspension was filtered and the collected solid was washed with DCM (3×1 mL). The solid was dried under vacuum at 40° C. to yield compound 5a (117 mg, 56%).

The following intermediate was prepared using a methodology similar to the one described in Preparation 2:

2-amino-5-(2-cyanopropan-2-yl)pyrazolo[1,5-a]pyrimidine-3-carboxylic acid 5c.

Preparation 3: 1H-benzo[d][1,2,3]triazol-1-yl 2-amino-5-(trifluoromethyl)pyrazolo[1,5-a]pyrimidine-3-carboxylate 6a

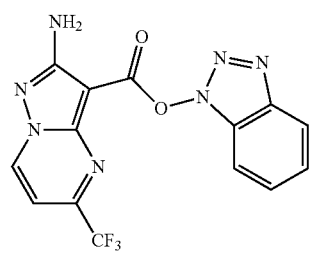

6a

Triethylamine (994.9 mg, 1.370 mL, 9.832 mmol) was added to a suspension of 2-amino-5-(trifluoromethyl)pyrazolo[1,5-a]pyrimidine-3-carboxylic acid 5a (2.2 g, 8.938 mmol) in chloroform (22 mL). TBTU (2.870 g, 8.938 mmol) was added to the solution and the reaction mixture was heated at 50° C. for 20 min, during which time a yellow precipitate formed. The reaction mixture was cooled to ambient temperature. The precipitate was isolated by filtration and washed with chloroform to leave the product (benzotriazol-1-yl 2-amino-5-(trifluoromethyl)pyrazolo[1,5-a]pyrimidine-3-carboxylate) 6a as an off-white solid (2.8 g, 86% yield).). LC-MS (M+H)+ 364.0; ¹H NMR (500 MHz, DMSO-d6) δ 9.40-9.28 (m, 1H), 8.19 (dt, J=8.5, 0.9 Hz, 1H), 7.80 (dt, J=8.4, 0.9 Hz, 1H), 7.72-7.63 (m, 2H), 7.55 (m, J=8.5, 6.9, 1.0 Hz, 1H), 7.13 (s, 2H).

Preparation 4: 2-amino-5-(2-(dimethylamino)ethoxy) pyrazolo[1,5-a]pyrimidine-3-carboxylic acid 5b

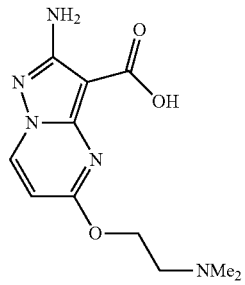

Step 1: allyl 2-amino-5-oxo-4,5-dihydropyrazolo[1,5-a]pyrimidine-3-carboxylate To a mixture of allyl 3,5-diamino-1H-pyrazole-4-carboxylate 3 (1 g, 5.489 mmol) and Cs$_2$CO$_3$ (2.504 g, 7.685 mmol) in EtOH (10 mL) was added methyl prop-2-ynoate (553.8 mg, 586.0 µL, 6.587 mmol), dropwise, over 15 minutes. The reaction mixture was stirred overnight at room temperature. The deep red reaction mixture was then filtered, washing through with a small amount of ethanol. The filtrate was cooled on an ice-bath and ether (100 ml) was slowly added; the mixture stirred at 0° C. for 20 mins. A yellow solid precipitated out of solution and was filtered off to afford a solid which was triturated in ether and filtered (3 cycles) to yield pure product as a yellow solid (yield 54%) LC-MS (M+H)$^+$=235.1

Step 2: allyl 2-amino-5-(2-(dimethylamino)ethoxy) pyrazolo[1,5-a]pyrimidine-3-carboxylate 4b To a mixture of allyl 2-amino-5-oxo-4H-pyrazolo[1,5-a]pyrimidine-3-carboxylate (1 g, 4.270 mmol) in MeCN (15 mL) was added 2,3,4,6,7,8,9,10-octahydropyrimido[1,2-a]azepine (975.1 mg, 957.9 µL, 6.405 mmol) and benzotriazol-1-yloxy(tripyrrolidin-1-yl)phosphonium (Phosphorus Hexafluoride Ion) (2.666 g, 5.124 mmol). After 5 minutes, 2-dimethylaminoethanol (3.806 g, 4.291 mL, 42.70 mmol) and cesium carbonate (5 g) were added and the mixture was stirred at room temperature for 30 minutes, followed by heating to 50° C. for 30 minutes. After cooling to room temperature the mixture was filtered and the solid washed with acetonitrile. The combined filtrate was concentrated in vacuo to an orange oil and purified by column chromatography using 4% MeOH/DCM as eluent to provide 4b (yield 35%) LC-MS (M+H)$^+$=306.2.

Step 3: 2-amino-5-(2-(dimethylamino)ethoxy)pyrazolo[1,5-a]pyrimidine-3-carboxylic acid 5b Palladium triphenylphosphane (170.3 mg, 0.1474 mmol) was added to a solution of phenylsilane (478.5 mg, 550 µL, 4.422 mmol) and allyl 2-amino-5-[2-(dimethylamino)ethoxy]pyrazolo[1,5-a]pyrimidine-3-carboxylate 4b (900 mg, 2.948 mmol) in DCM (5 mL). The reaction mixture was stirred at room temperature for 3 h. Ether was slowly added and the white solid was then filtered off, washed with small amount of diethyl ether and dried to afford pure product as off-white solid (yield 67%); LC-MS (M+H)$^+$=266.1; $^1$H NMR (500 MHz, DMSO-d6) δ 12.35 (brs, 1H), 9.65 (brs, 1H), 8.72 (d, 1H), 6.55 (d, 1H), 6.25-6.15 (m, 2H), 4.73-4.70 (m, 2H), 3.58-3.55 (m, 2H), 2.90 (s, 6H);

Preparation 5: 3,5-diamino-N-(4-methoxypyridin-3-yl)-1H-pyrazole-4-carboxamide 9

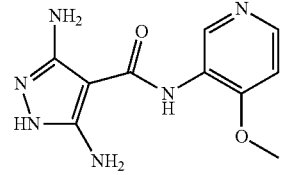

Step 1: 2-cyano-N-(4-methoxypyridin-3-yl)acetamide 8

4-Methoxypyridin-3-amine (22 g, 177.2 mmol) and 2-cyanoacetic acid (19.60 g, 230.4 mmol) were slurried in THF (1 L). The mixture was cooled in an ice bath and DMAP (28.15 g, 230.4 mmol) was added followed by 3-(ethyliminomethyleneamino)-N,N-dimethyl-propan-1-amine hydrochloride (50.95 g, 265.8 mmol). The mixture was allowed to warm to ambient temperature and stirred overnight. The mixture was partially concentrated, then diluted with ethyl acetate/water. The organic phase was isolated and washed with saturated NaHCO$_3$, then brine, dried (MgSO$_4$), filtered and concentrated. The residue was slurried in ether/petrol to give 2-cyano-N-(4-methoxypyridin-3-yl)acetamide 8 as a yellow solid (26.4 g, 78%). LC-MS (M+H)$^+$ 192.0; $^1$H NMR (500 MHz, DMSO-d6) δ 9.81 (s, 1H), 8.86 (s, 1H), 8.28 (d, 1H), 7.15 (d, 1H), 4.00 (s, 2H), 3.92 (s, 3H).

Step 2: 3,5-diamino-N-(4-methoxypyridin-3-yl)-1H-pyrazole-4-carboxamide 9

2-Cyano-N-(4-methoxy-3-pyridyl)acetamide 8 (26.4 g, 138.1 mmol) was slurried in ethanol (300 mL). Sodium acetate (23.56 g, 287.2 mmol) was added followed by trichloroacetonitrile (23.92 g, 16.85 mL, 165.7 mmol). The mixture was stirred at room temperature overnight. The suspension was filtered and the solids washed with ethanol. The solids (46.5 g) were slurried for 90 minutes in 10% aqueous ethanol, filtered and dried to afford 3-amino-4,4,4-trichloro-2-cyano-N-(4-methoxy-3-pyridyl)but-2-enamide (37.2 g, 80%). LC-MS (M+H)$^+$ 336.9; $^1$H NMR (500 MHz, DMSO-d6) δ 8.44 (d, 1H), 7.43-7.47 (m, 1H), 6.35-6.39 (m, 1H), 4.04 (s, 3H).

3-Amino-4,4,4-trichloro-2-cyano-N-(4-methoxy-3-pyridyl)but-2-enamide (37.2 g, 110.9 mmol) was dissolved in N-methylpyrrolidinone (200 mL). Hydrazine hydrate (14.43 g, 14.02 mL, 288.3 mmol) was added portionwise, then the mixture heated to 80° C. for 20 hr. The mixture was cooled to ambient and concentrated in vacuo. The viscous red oil was stirred as TBME (180 ml)/DCM (20 ml) was added. The yellow solid that precipitated was filtered, washed with TBME and dried to afford the title compound (26.9 g, 98%). LC-MS (M+H)$^+$ 249.0; $^1$H NMR (500 MHz, DMSO-d6) δ 11.90 (br s, 1H), 9.32 (s, 1H), 9.14 (s, 1H), 8.15 (d, 1H), 7.10 (d, 1H), 3.92 (s, 3H).

Preparation 6: 2-amino-N-(4-methoxypyridin-3-yl)-5-oxo-4,5-dihydropyrazolo[1,5-a]pyrimidine-3-carboxamide

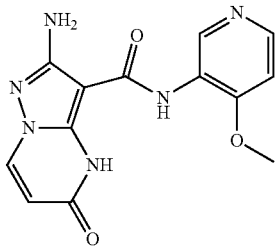 [SMILES: COc1ccncc1NC(=O)c1c(N)nn2ccc(=O)[nH]c12]

To a mixture of 3,5-diamino-N-(4-methoxy-3-pyridyl)-1H-pyrazole-4-carboxamide 9 (300 mg, 1.209 mmol) and Cs$_2$CO$_3$ (591 mg, 1.814 mmol) in EtOH (5 mL) was added methyl prop-2-ynoate (203.3 mg, 215.1 µL, 2.418 mmol), dropwise, over 15 minutes and the reaction mixture was stirred overnight at room temperature. The mixture was filtered and product purified by preparative HPLC. Solvents were evaporated in vacuo to afford the product as a yellow solid (yield 27%). LC-MS (M+H)$^+$=301.1; $^1$H NMR (500 MHz, DMSO-d6) δ 10.18 (s, 1H), 9.58 (s, 1H), 8.71 (d, 1H), 8.58 (d, 1H), 7.68 (d, 1H), 6.45 (d, 1H), 6.38-6.28 (m, 2H), 4.25 (s, 3H);

Example 1

2-amino-N-(4-methoxypyridin-3-yl)-5-(trifluoromethyl)pyrazolo[1,5-a]pyrimidine-3-carboxamide (Compound I-O-1)

2-Amino-5-(trifluoromethyl)pyrazolo[1,5-a]pyrimidine-3-carboxylic acid 5a (100 mg, 0.4063 mmol), 4-methoxypyridin-3-amine (50.44 mg, 0.4063 mmol) and DIPEA (52.51 mg, 70.77 µL, 0.4063 mmol) were dissolved in dry NMP (812.6 µL) in a microwave tube. TBTU (130.5 mg, 0.4063 mmol) was added in one portion and the resulting mixture was stirred at RT for ~10 minutes and at 100° C. for ~2 h under microwave conditions. The reaction mixture was allowed to cool to RT and filtered through a SCX-2 cartridge (5 g). The cartridge was washed with MeOH/DCM and eluted with 2M NH$_3$ in MeOH (3×10 mL). The eluate was concentrated under reduced pressure. The residue was purified by column chromatography on silica (7.5% MeOH in DCM, ~75 mL) to give the desired Compound I-O-1 as a bright yellow solid (87.9 mg, 61% Yield). LC-MS (M+H)$^+$353.1; $^1$H NMR (500 MHz, DMSO-d6) δ 9.93 (s, 1H), 9.55 (s, 1H), 9.26 (dd, 1H), 8.24 (dd, 1H), 7.50-7.51 (d, 1H), 7.17-7.18 (d, 1H), 6.99 (s, 2H), 4.00 (s, 3H).

Example 2

2-amino-N-(4-methylpyridin-3-yl)-5-(trifluoromethyl)pyrazolo[1,5-a]pyrimidine-3-carboxamide (Compound I-C-1)

To a solution of benzotriazol-1-yl 2-amino-5-(trifluoromethyl)pyrazolo[1,5-a]pyrimidine-3-carboxylate 6a (150 mg, 0.4129 mmol) in NMP (1.666 mL) was added 4-methylpyridin-3-amine (44.65 mg, 0.4129 mmol) and the reaction mixture was stirred at 100° C. for 17 hours in a sealed tube. The solid precipitate was filtered and dried under vacuum to afford the desired Compound I-C-1 as a yellow powder (60.4 mg, 42%). LC-MS (M+H)$^+$ 337.2; $^1$H NMR (500 MHz, DMSO-d6) δ 9.45 (s, 1H), 9.40 (s, 1H), 9.30 (dd, J=6.9, 0.6 Hz, 1H), 8.22 (d, J=4.7 Hz, 1H), 7.52 (d, J=6.9 Hz, 1H), 7.33 (d, J=4.8 Hz, 1H), 7.01 (s, 2H), 2.42 (s, 3H).

Example 3

2-amino-N-(4-(piperidin-4-yloxy)pyridin-3-yl)-5-(trifluoromethyl)pyrazolo[1,5-a]pyrimidine-3-carboxamide (Compound I-O-41)

The Boc-protected precursor of I-O-41 (130 mg) was dissolved in DCM (550 µL) and TFA (21.55 mg, 14.56 µL, 0.189 mmol) was added. The reaction mixture was stirred at ambient temperature for 1 hour and then filtered through a SCX-2 cartridge (2 g) which was washed with DCM/Methanol (1:1, 3×8 mL) and then eluted with 2 M ammonia in methanolic solution (2×8 mL). The eluate was evaporated and the residue was purified by HPLC to afford the desired compound I-O-41 as a bright yellow solid (51 mg, 64%). LC-MS (M+H)+ 422.1; $^1$H NMR (500 MHz, DMSO-d6) δ 9.34 (d, J=8.5 Hz, 2H), 9.26 (d, J=6.9 Hz, 1H), 8.19 (d, J=5.6 Hz, 1H), 7.50 (d, J=6.9 Hz, 1H), 7.24 (d, J=5.7 Hz, 1H), 7.02 (s, 2H), 4.67 (tt, J=9.4, 4.2 Hz, 1H), 2.95 (dt, J=12.4, 4.2 Hz, 2H), 2.60 (ddd, J=13.0, 10.7, 2.7 Hz, 2H), 1.97 (dq, J=11.8, 3.8 Hz, 2H), 1.55 (dtd, J=14.1, 10.3, 4.0 Hz, 2H); $^{19}$F NMR (471 MHz, DMSO) δ −66.51.

Example 4

5-((allyloxy)methyl)-2-amino-N-(4-methoxypyridin-3-yl)pyrazolo[1,5-a]pyrimidine-3-carboxamide (Compound I-O-55)

3,5-Diamino-N-(4-methoxy-3-pyridyl)-1H-pyrazole-4-carboxamide 9 (250 mg, 1.007 mmol), 1-allyloxy-3-(1,3-dioxolan-2-yl)propan-2-one (187.5 mg, 1.007 mmol) and KOH (5.650 mg, 0.1007 mmol) were suspended in dry EtOH (5 mL) and stirred at RT for 2 hr. The light brown suspension was filtered and the collected solid was purified by column chromatography on silica (7.5% MeOH in DCM, ~75 mL) to give the desired Compound I-O-55 as a light yellow solid (206.5 mg, 58% Yield). LC-MS (M+H)+ 355.2; $^1$H NMR (500 MHz, DMSO-d6) δ 10.19 (s, 1H), 9.52 (s, 1H), 8.95 (d, J=6.9 Hz, 1H), 8.21 (d, J=5.5 Hz, 1H), 7.16 (d, J=5.5 Hz, 1H), 7.09 (d, J=6.9 Hz, 1H), 6.62 (s, 2H), 6.01 (ddt, J=17.3, 10.6, 5.4 Hz, 1H), 5.37 (dq, J=17.3, 1.8 Hz, 1H), 5.24 (ddt, J=10.5, 2.0, 1.3 Hz, 1H), 4.71 (s, 2H), 4.18 (dt, J=5.4, 1.5 Hz, 2H), 4.03 (s, 3H).

Example 5

2-amino-5-(hydroxymethyl)-N-(4-methoxypyridin-3-yl)pyrazolo[1,5-a]pyrimidine-3-carboxamide (Compound I-O-54)

5-(Allyloxymethyl)-2-amino-N-(4-methoxy-3-pyridyl)pyrazolo[1,5-a]pyrimidine-3-carboxamide I-O-55 (50 mg, 0.1411 mmol) and Pd(PPh$_3$)$_4$ (11.41 mg, 0.009877 mmol) were suspended in dry DCM (0.75 mL). A solution of sodium 4-methylbenzenesulfinate (50.28 mg, 0.2822 mmol) and HCl (23.52 µL of 12 M, 0.2822 mmol) in dry DCM (0.75 mL) were added and the resulting mixture was stirred at RT for ~90 mins. The bright yellow suspension was added to a pre-wetted (MeOH) SCX-2 cartridge (5 g) and the cartridge was washed with MeOH/DCM. The cartridge was then eluted with 2M NH₃ in MeOH (3×10 mL) and the eluate was concentrated under reduced pressure. The residue was purified by column chromatography on silica (7.5% MeOH/1% NH₄OH in DCM, ~75 mL) to the desired Compound I-O-54 as an off-white solid (17.6 mg, 33%). LC-MS (M+H)+ 315.2; $^1$H NMR (500 MHz, DMSO-d6) δ 10.23 (s, 1H), 9.52 (s, 1H), 8.94 (d, J=6.9 Hz, 1H), 8.21 (d, J=5.5 Hz, 1H), 7.16 (d, J=5.5 Hz, 1H), 7.14 (d, J=6.9 Hz, 1H), 6.58 (s, 2H), 5.77 (t, J=6.0 Hz, 1H), 4.71 (d, J=6.0 Hz, 2H), 4.03 (s, 3H).

Example 6

2-amino-N-(4-methoxypyridin-3-yl)-5-((methylamino)methyl)pyrazolo[1,5-a]pyrimidine-3-carboxamide (Compound I-O-66)

Step 1: 5-((allyloxy)methyl)-N-(4-methoxypyridin-3-yl)-2-(2,2,2-trifluoroacetamido)pyrazolo[1,5-a]pyrimidine-3-carboxamide 5-(Allyloxymethyl)-2-amino-N-(4-methoxy-3-pyridyl)pyrazolo[1,5-a]pyrimidine-3-carboxamide I-O-55 (120 mg, 0.3386 mmol) and Et₃N (51.39 mg, 70.79 μL, 0.5079 mmol) were suspended in dry DCM (3 mL) and cooled in an ice-bath. Trifluoroacetic anhydride (78.24 mg, 51.78 μL, 0.3725 mmol) was added dropwise and the resulting mixture was stirred over 72 h, allowing the ice-bath to melt. The ochre suspension was cooled in an ice-bath and further DCM (3 mL) and Et₃N (51.39 mg, 70.79 μL, 0.5079 mmol) were added, followed by trifluoroacetic anhydride (78.24 mg, 51.78 μL, 0.3725 mmol). The mixture was stirred at 0° C. for ~55 mins and at RT for ~30 mins. The suspension was diluted with 10% MeOH in DCM and washed with saturated NaHCO₃. The organic layer was dried over Na₂SO₄, filtered and concentrated under reduced pressure to give a yellow solid which was purified by column chromatography on silica (7.5% MeOH/1% NH₄OH in DCM, ~75 mL) to give the desired product as an off-white solid (74.7 mg, 49%). LC-MS (M+H)+ 451.2; $^1$H NMR (500 MHz, DMSO-d6) δ 11.68 (s, 1H), 10.29 (s, 1H), 9.46 (s, 1H), 9.39 (s, 1H), 8.31-8.26 (m, 1H), 7.42 (s, 1H), 7.22 (d, J=5.5 Hz, 1H), 6.02 (ddt, J=17.3, 10.6, 5.4 Hz, 1H), 5.43-5.32 (m, 1H), 5.25 (ddt, J=10.4, 2.0, 1.3 Hz, 1H), 4.82 (s, 2H), 4.21 (dt, J=5.4, 1.5 Hz, 2H), 4.05 (d, J=8.2 Hz, 3H).

Step 2: 5-(hydroxymethyl)-N-(4-methoxypyridin-3-yl)-2-(2,2,2-trifluoroacetamido)pyrazolo[1,5-a]pyrimidine-3-carboxamide 5-(Allyloxymethyl)-N-(4-methoxy-3-pyridyl)-2-[(2,2,2-trifluoroacetyl)amino]pyrazolo[1,5-a]pyrimidine-3-carboxamide (70 mg, 0.1554 mmol), 1,3-dimethylbarbituric acid (48.53 mg, 0.3108 mmol) and Pd(PPh₃)₄ (17.96 mg, 0.01554 mmol) were suspended in DCM/MeOH (1.4 mL/0.35 mL) in a pressure tube. The mixture was stirred at 60° C. for ~2.5 hrs. Further DCM (1.4 mL), MeOH (0.35 mL) and Pd(PPh₃)₄ (17.96 mg, 0.01554 mmol) were added and the resulting mixture was stirred at 60° C. overnight. The reaction was allowed to cool to RT, the suspended solid was collected by filtration and washed with DCM (2×1 mL) and ether (3×1 mL) to give a purple powder (53.7 mg, 84% Yield) which was used directly into next step without further purification. LC-MS (M+H)+ 411.2; $^1$H NMR (500 MHz, DMSO-d6) δ 11.66 (s, 1H), 10.34 (s, 1H), 9.45 (s, 1H), 9.37 (d, J=7.1 Hz, 1H), 8.29 (d, J=5.5 Hz, 1H), 7.46 (d, J=7.1 Hz, 1H), 7.23 (d, J=5.6 Hz, 1H), 5.93 (t, J=6.1 Hz, 1H), 4.81 (d, J=6.0 Hz, 2H), 4.06 (s, 3H).

Step 3: 5-(chloromethyl)-N-(4-methoxypyridin-3-yl)-2-(2,2,2-trifluoroacetamido)pyrazolo[1,5-a]pyrimidine-3-carboxamide The crude 5-(hydroxymethyl)-N-(4-methoxy-3-pyridyl)-2-[(2,2,2-trifluoroacetyl)amino]pyrazolo[1,5-a]pyrimidine-3-carboxamide prepared in step 2 above (50 mg, 0.1219 mmol) and DMF (44.55 mg, 47.19 μL, 0.6095 mmol) were suspended in dry DCM (1.25 mL). SOCl₂ (72.51 mg, 44.46 μL, 0.6095 mmol) was added dropwise and the resulting mixture was stirred at RT for ~2 h. The bright yellow suspension was filtered and the collected solid was washed with DCM (1 mL) and ether (3×1 mL) to give a light yellow powder (49.6 mg). LC-MS (M+H)+ 429.1; $^1$H NMR (500 MHz, DMSO-d6) δ 11.78 (s, 1H), 10.60 (s, 1H), 9.63 (s, 1H), 9.50 (d, J=7.1 Hz, 1H), 8.71 (d, J=6.4 Hz, 1H), 7.80 (d, J=6.6 Hz, 1H), 7.62 (d, J=7.1 Hz, 1H), 5.07 (s, 2H), 4.34 (s, 3H).

Step 4: 2-amino-N-(4-methoxypyridin-3-yl)-5-((methylamino)methyl)pyrazolo[1,5-a]pyrimidine-3-carboxamide (Compound I-O-66)

5-(Chloromethyl)-N-(4-methoxy-3-pyridyl)-2-[(2,2,2-trifluoroacetyl)amino]pyrazolo[1,5-a]pyrimidine-3-carboxamide (45 mg, 0.105 mmol) and sodium iodide were dissolved in MeNH₂ (10 mL of 2M in) in a sealed tube and stirred at 50° C. for 48 hours. The reaction mixture was concentrated under reduced pressure. The residue was filtered through SCX-2 cartridge (5 g) and the eluate was concentrated under reduced pressure. The residue was purified by column chromatography on silica (7.5% MeOH/1% NH₄OH in DCM, ~75 mL) to give a solid which was triturated in ether and collected by filtration to give compound I-O-66 as an off-white powder (16.6 mg, 29% Yield). LC-MS (M+H)+ 328.2; $^1$H NMR (500 MHz, DMSO) δ 9.86 (s, 1H), 9.40 (s, 1H), 9.25 (s, 2H), 9.11 (d, J=6.9 Hz, 1H), 8.54 (d, J=6.2 Hz, 1H), 7.56 (d, J=6.1 Hz, 1H), 7.19 (d, J=6.9 Hz, 1H), 6.77 (s, 2H), 4.48 (s, 2H), 4.16 (s, 3H), 2.78 (s, 3H).

Example 7

2-amino-5-(2-(dimethylamino)ethoxy)-N-(4-methylpyridin-3-yl)pyrazolo[1,5-a]pyrimidine-3-carboxamide (Compound I-C-3)

To a suspension of 2-amino-5-[2-(dimethylamino)ethoxy]pyrazolo[1,5-a]pyrimidine-3-carboxylic acid (100 mg, 0.377 mmol) in NMP (667 μL) was added Et₃N (46.54 mg, 64.1 μL, 0.4599 mmol) in one portion. The mixture was stirred for 10 minutes before adding TBTU (Boron Tetrafluoride Ion) (136.3 mg, 0.4245 mmol), portionwise, over 5 minutes. The mixture was allowed to stir at room temperature for 20 mins. 4-Methylpyridin-3-amine (40.77 mg, 0.377 mmol) was added and the mixture was heated to 100° C. for 4 hours. The mixture was filtered through a silica gel pad and eluted with DCM initially followed by 20/80 MeOH/DCM. The residue was further purified by preparative HPLC to provide compound I-C-3 (42% yield). LC-MS (M+H)+=356.2; $^1$H NMR (500 MHz, DMSO-d6) δ 9.80 (s, 1H), 9.38 (brs, 1H), 9.20 (brs, 1H), 8.82 (d, 1H), 8.50-8.43 (m, 1H), 7.66-7.6 (m, 1H), 6.62 (d, 1H), 6.50 (brs, 2H), 4.81-4.78 (m, 2H), 3.63-3.60 (m, 2H), 2.95 (s, 6H), 2.55 (s, 3H);

Example 8

2-amino-N-(4-methoxypyridin-3-yl)-5-((1-methylpyrrolidin-3-yl)oxy)pyrazolo[1,5-a]pyrimidine-3-carboxamide (Compound I-O-57)

To a mixture of 2-amino-N-(4-methoxy-3-pyridyl)-5-oxo-4H-pyrazolo[1,5-a]pyrimidine-3-carboxamide (15 mg, 0.04995 mmol) in MeCN (3 mL) was added 2,3,4,6,7,8,9,10-octahydropyrimido[1,2-a]azepine (15.21 mg, 14.94 µL, 0.0999 mmol) and benzotriazol-1-yloxy(tripyrrolidin-1-yl)phosphonium (Phosphorus Hexafluoride) (38.99 mg, 0.07492 mmol). After 5 minutes, 1-methylpyrrolidin-3-ol (25.27 mg, 27.44 µL, 0.2498 mmol) and cesium carbonate (32.55 mg, 0.0999 mmol) were added and the mixture was stirred at RT for 1 h. The mixture was filtered and purified directly by preparative HPLC to yield compound I-O-57 (44% yield). LC-MS (M+H)$^+$=384.2; $^1$H NMR (500 MHz, DMSO-d6) δ 10.35 (s, 1H), 9.60 (s, 1H), 9.55 (s, 1H), 8.90 (d, 1H), 8.55 (d, 1H), 7.66-7.60 (m, 1H), 6.62-6.40 (m, 3H), 5.80 (brs, 1H), 4.20 (s, 3H), 4.02-3.98 (m, 1H), 3.70-3.65 (m, 1H), 3.40-3.35 (m, 1H), 3.30-3.20 (m, 1H), 2.95 (s, 3H), 2.80-2.70 (m, 1H), 2.30-2.20 (m, 1H);

Example 9

2-amino-N-(4-methoxypyridin-3-yl)-5-((2-(pyrrolidin-1-yl)ethyl)amino)pyrazolo[1,5-a]pyrimidine-3-carboxamide (Compound I-O-72)

To a mixture of 2-amino-N-(4-methoxy-3-pyridyl)-5-oxo-4H-pyrazolo[1,5-a]pyrimidine-3-carboxamide (15 mg, 0.04995 mmol) in MeCN (1 mL) was added 2,3,4,6,7,8,9,10-octahydropyrimido[1,2-a]azepine (15.21 mg, 14.94 µL, 0.0999 mmol) and bromo(tripyrrolidin-1-yl)phosphonium (Phosphorus Hexafluoride) (27.94 mg, 0.05994 mmol). A few drops of DMF were added to dissolve the mixture. 2-Pyrrolidin-1-ylethanamine (11.41 mg, 0.0999 mmol) was added and the mixture was stirred at RT for 30 minutes. The mixture was concentrated in vacuo and the residue was purified by preparative HPLC to yield compound I-O-72 (12 mg, 93% yield). LC-MS (M+H)$^+$=397.3; $^1$H NMR (500 MHz, DMSO-d6) δ 9.85 (s, 1H), 9.63 (s, 1H), 8.52 (d, 1H), 8.40 (d, 1H), 8.20 (s, 1H), 7.65 (d, 1H), 6.25 (d, 1H), 6.20-6.10 (brs, 1H), 4.15 (s, 3H), 3.93-3.87 (m, 2H), 3.61-3.55 (m, 2H), 3.48-3.42 (m, 2H), 3.10-3.00 (m, 2H), 2.00-1.90 (m, 2H), 1.90-1.80 (m, 2H);

The novel aminopyridines required for the preparation of some of the compounds described in this patent application have been prepared using a methodology similar to the one described below in 'Preparation 7' for 4-(oxetan-3-yloxy)pyridin-3-amine Preparation 7: 4-(oxetan-3-yloxy)pyridin-3-amine

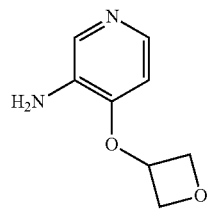 [SMILES: Nc1cnccc1OC1COC1]

Step 1: 3-nitro-4-(oxetan-3-yloxy)pyridine

NaH (164.0 mg, 4.100 mmol) was added portionwise to a stirred solution of oxetan-3-ol (280.4 mg, 3.785 mmol) in THF (10.00 mL) to form a white suspension. The reaction mixture was stirred at ambient temperature for 10 mins then was added dropwise to a suspension of 4-chloro-3-nitro-pyridine (500 mg, 3.154 mmol) in THF (3 mL). The reaction mixture was stirred at ambient temperature for 1 hour. The reaction was quenched with water (20 mL) and partitioned with ethyl acetate (3×20 mL). The combined organics were washed with brine, dried (MgSO$_4$), filtered and evaporated to dryness to afford the desired product as a beige solid (499 mg, 81%). LC-MS (M+H)+ 198.1; $^1$H NMR (500 MHz, DMSO-d6) δ 9.06 (s, 1H), 8.66 (d, J=5.9 Hz, 1H), 7.09 (d, J=5.9 Hz, 1H), 5.60 (tt, J=6.0, 4.7 Hz, 1H), 4.99 (ddd, J=7.9, 6.0, 1.1 Hz, 2H), 4.61 (ddd, J=7.7, 4.7, 1.1 Hz, 2H).

Step 2: 4-(oxetan-3-yloxy)pyridin-3-amine

3-Nitro-4-(oxetan-3-yloxy)pyridine (499 mg) was dissolved in methanol (10 mL) and Pd on C, wet, Degussa was added. The reaction mixture was flushed nitrogen twice and then stirred under a hydrogen atmosphere for 3 hours. The reaction mixture was filtered through a prewetted (methanol, 5 mL) Celite cartridge (2.5 g) and washed with methanol (25 mL). The filtrate was concentrated in vacuo to afford the desired product as a pale orange oil (432 mg, 97.7%). LC-MS (M+H)+ 196.3; $^1$H NMR (500 MHz, DMSO-d6) δ 7.91 (s, 1H), 7.67 (d, J=5.3 Hz, 1H), 6.45 (d, J=5.3 Hz, 1H), 5.32 (tt, J=6.0, 4.8 Hz, 1H), 4.96 (s, 2H), 4.95 (ddd, J=7.1, 6.0, 1.0 Hz, 2H), 4.59 (ddd, J=7.3, 4.8, 1.0 Hz, 2H).

Preparation 8: (1-(3-amino-5-fluoropyridin-4-yl)piperidin-4-yl)(4-methylpiperazin-1-yl)methanone (hydrobromide) 17

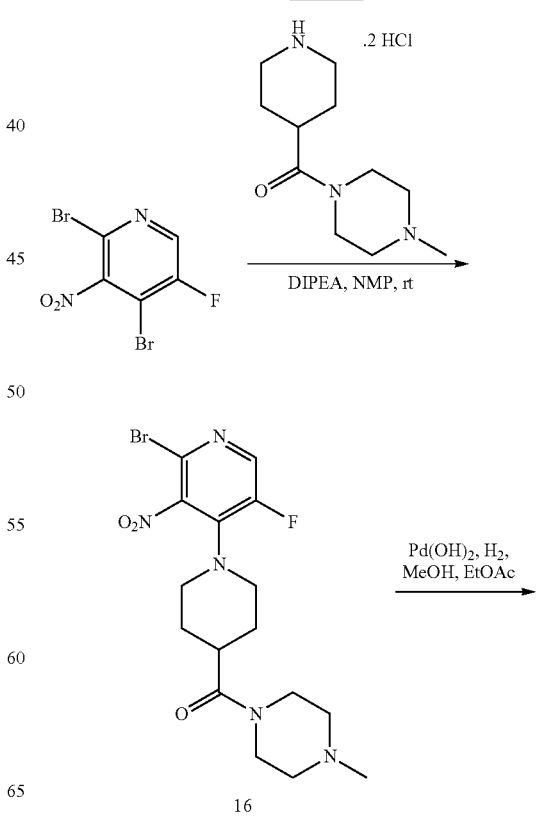

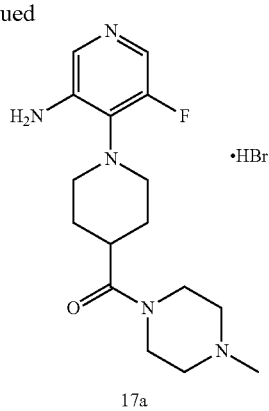

17a

Step 1: (1-(2-bromo-5-fluoro-3-nitropyridin-4-yl)piperidin-4-yl)(4-methylpiperazin-1-yl)methanone 16

A round-bottomed flask was charged with (4-methylpiperazin-1-yl)-(4-piperidyl)methanone dihydrochloride (16.45 g, 57.89 mmol) and DIPEA (23.20 g, 31.27 mL, 179.5 mmol) in NMP (160 mL). 2,4-Dibromo-5-fluoro-3-nitro-pyridine (17.36 g, 57.89 mmol) was added and the reaction mixture was stirred overnight at room temperature under a nitrogen atmosphere. Additional (4-methylpiperazin-1-yl)-(4-piperidyl)methanone dihydrochloride (1.65 g, 0.1 eq) and DIPEA (1 mL, 0.1 eq) was added and stirred at room temperature for a further 3 h. The mixture diluted with EtOAc, washed with water (3×). The aqueous layer was extracted with EtOAc (3×) and the combined organic extracts were combined, washed with brine, dried (sodium sulfate), filtered and concentrated in vacuo. The crude product was purified by chromatography (330 g $SiO_2$, 0 to 5% MeOH (containing 10% ammonium hydroxide)/DCM) to afford product as a yellow solid (20.24 g, 81%). MS (ES+) 432.0.

Step 2: (1-(3-amino-5-fluoropyridin-4-yl)piperidin-4-yl)(4-methylpiperazin-1-yl)methanone hydrobromide 17a

[1-(2-Bromo-5-fluoro-3-nitro-4-pyridyl)-4-piperidyl]-(4-methylpiperazin-1-yl)methanone 16 (20.24 g, 47.04 mmol) was dissolved/suspended in MeOH (389 mL)/EtOAc (78 mL) and $Pd(OH)_2$ (1.651 g, 2.352 mmol) was added. The resulting mixture was degassed by vacuum/nitrogen cycles (×5) and the atmosphere was exchanged by vacuum/hydrogen cycles (×5). The reaction mixture was stirred vigorously under a hydrogen atmosphere (balloon) for 6 hrs. Additional $Pd(OH)_2$ (4.95 g) was added and the reaction mixture was stirred overnight under hydrogen. The mixture was filtered through celite, washing through with methanol. The filtrate was concentrated in vacuo to leave an orange gum. Approx. 150 mL of ethanol was added and the mixture rotated on buchii for 10 mins, a yellow precipitate had formed during this time. The suspension was sonicated for 5 mins and the solid was then collected by filtration, washed with minimal ethanol and dried by suction for 1 h to afford product as a pale yellow solid. A second crop of product was obtained by concentrating the filtrate in vacuo. The residue was then slurried in minimal ethanol and sonicated for 5 mins then solid collected by filtration, dried by suction to leave second crop of product as a yellow solid. Both crops of product were combined to afford product as a yellow solid (15.8 g, 79%). MS (ES+) 322.2.

Preparation 9: (1-(3-amino-5-fluoropyridin-4-yl)piperidin-4-yl)(4-methylpiperazin-1-yl)methanone (hydrochloride) 17

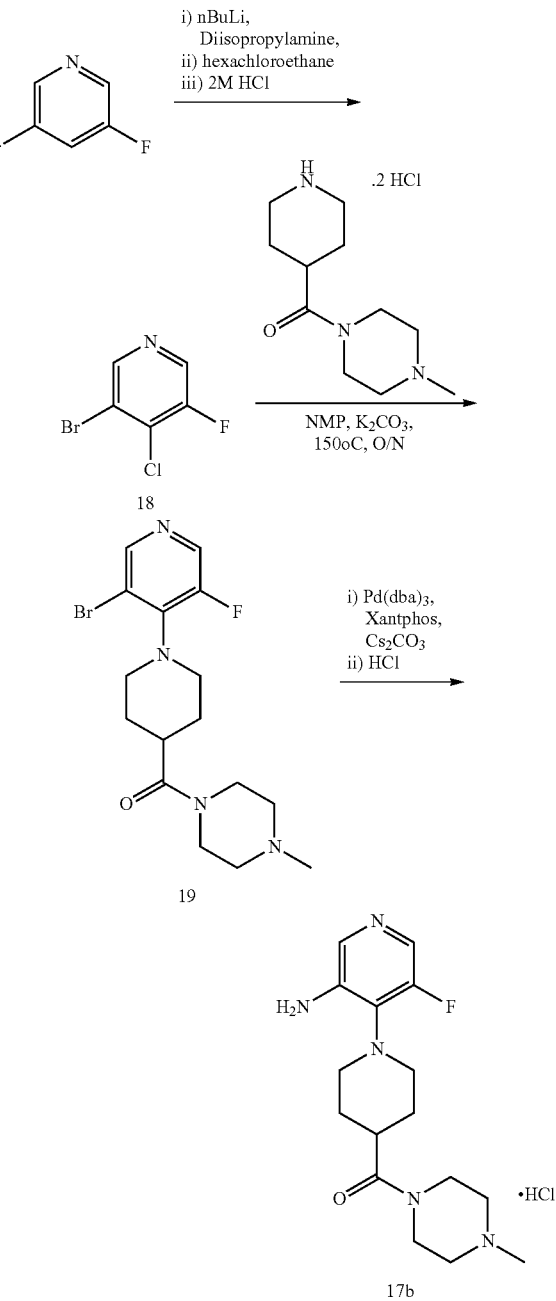

Scheme 4

Step 1: 3-bromo-4-chloro-5-fluoropyridine hydrochloride 18

To a solution of diisopropylamine (6.899 g, 9.555 mL, 68.18 mmol) in THF (75 mL) cooled to −78° C., was added butyllithium (25 mL of 2.5 M in hexanes, 62.5 mmol). The reaction mixture was allowed to warm to −20° C. then cooled back down to −78° C. A solution of 3-bromo-5-fluoro-pyridine (10 g, 56.82 mmol) in THF (25 mL) was added dropwise keeping temperature below −70° C. (approx 30 mins). The reaction mixture was stirred at −78° C. for 30 min and a solution of 1,1,1,2,2,2-hexachloroethane (14.8 g, 62.5 mmol) in THF (20 mL) was then added dropwise, keeping temperature below −70° C. (over approx 30 mins). The mixture was stirred at −78° C. for 20 minutes, allowed to warm to room temperature, cooled back to 0° C. and quenched with water (100 mL). EtOAc (400 mL) was then added, and organic layer separated, washed with water (2×), brine (1×), dried (MgSO$_4$), filtered and concentrated in vacuo to leave a brown solid. The solid was triturated in pentane (100 mL) for 10 minutes, then filtered. The filtrate was concentrated in vacuo to afford product as a brown oil that turned to a crystalline solid on standing, 11.85 g, 89%). $^1$H NMR (DMSO-d6) δ 8.78 (s, 1H), 8.76 (s, 1H).

To a solution of 3-bromo-4-chloro-5-fluoro-pyridine (7.56 g, 32.18 mmol) in pentane (100 mL) was added hydrogen chloride (2M in ether) (17.7 mL of 2 M, 35.4 mmol). An off-white precipitate formed instantly. The mixture was stirred for 5 minutes then the solid was collected by filtration, washed with pentane and dried by suction to afford the desired product as an off-white solid (4.79 g, 60%). $^1$H NMR (DMSO-d6) δ 8.77 (s, 1H), 8.75 (s, 1H).

Step 2: (1-(3-bromo-5-fluoropyridin-4-yl)piperidin-4-yl)(4-methylpiperazin-1-yl)methanone 19

A mixture of (4-methylpiperazin-1-yl)-(4-piperidyl) methanone dihydrochloride (50.65 g, 178.2 mmol), 3-bromo-4-chloro-5-fluoro-pyridine hydrochloride 18 (40 g, 162 mmol) and dipotassium carbonate (94.04 g, 680.4 mmol) in NMP (400 mL) was heated at 150° C. overnight. The mixture was cooled to room temperature then filtered to remove inorganic salts and the filtrate was concentrated in vacuo. The residue was dissolved in EtOAc (800 mL), washed with brine (100 mL×4), dried (MgSO$_4$), filtered and concentrated in vacuo to afford a brown viscous oil. This residue was purified by silica gel column (approx 800 g of silica), product loaded onto silica in DCM, then eluting with 3% methanol (containing 10% ammonium hydroxide)/DCM to afford the desired product as a brown oil which crystallised on standing (27.44 g, 44%). MS (ES+) 387.1.

Step 3: (1-(3-amino-5-fluoropyridin-4-yl)piperidin-4-yl)(4-methylpiperazin-1-yl)methanone hydrochloride 17b Pd$_2$(dba$_3$) (3.818 g, 4.169 mmol) and Xantphos (4.824 g, 8.337 mmol) were added to a degassed (3× vacuum/N$_2$ cycles) mixture of diphenylmethanimine (16.62 g, 15.39 mL, 91.71 mmol), [1-(3-bromo-5-fluoro-4-pyridyl)-4-piperidyl]-(4-methylpiperazin-1-yl)methanone 19 (32.12 g, 83.37 mmol) and Cs$_2$CO$_3$ (81.49 g, 250.1 mmol) in dioxane (550 mL) in a round-bottom flask under N$_2$. The reaction mixture was flushed with nitrogen via 2× vacuum/N$_2$ cycles then stirred at 100° C. overnight under N$_2$. The mixture cooled to room temperature then partitioned between EtOAc (1 L) and water (100 mL). The organic layer was separated, washed with water (2×100 mL), brine (1×100 mL), dried (MgSO$_4$), filtered and concentrated in vacuo to afford a dark orange viscous oil (56.15 g). This crude residue was then dissolved in THF (482 mL) and hydrogen chloride (300 mL of 2 M, 600 mmol) and the mixture was heated at 60° C. for 30 minutes.

THF was removed in vacuo and the remaining aqueous solution was washed with EtOAc (2×) then basified to pH=8 with 2M NaOH solution (approx. 310 mL), and extracted with EtOAc (3×). The combined organic extracts were washed with brine (1×), dried (MgSO$_4$), filtered and concentrated in vacuo to afford an orange solid (25.44 g). The orange solid was dissolved in dioxane (300 mL) then 4M HCl in dioxane (19.8 mL, 79.16 mmol) was added slowly over 10 mins. The mixture was stirred for 20 minutes and the precipitate that formed was collected by filtration, washed with dioxane (approx 100 mL), diethyl ether (100 mL), dried by suction to afford desired product as a white solid (25.13 g, 84%). MS (ES+) 322.2.

The compounds below were all prepared using a methodology similar to one or several of the methods described above:

2-amino-N-(4-methoxypyridin-3-yl)-5-(trifluoromethyl) pyrazolo[1,5-a]pyrimidine-3-carboxamide (Compound I-O-1);

2-amino-N-(4-ethoxypyridin-3-yl)-5-(trifluoromethyl)pyrazolo[1,5-a]pyrimidine-3-carboxamide (Compound I-O-2);

2-amino-N-(4-(2,2,2-trifluoroethoxy)pyridin-3-yl)-5-(trifluoromethyl)pyrazolo[1,5-a]pyrimidine-3-carboxamide (Compound I-O-3);

2-amino-N-(4-isopropoxypyridin-3-yl)-5-(trifluoromethyl) pyrazolo[1,5-a]pyrimidine-3-carboxamide (Compound I-O-4);

2-amino-N-(4-cyclobutoxypyridin-3-yl)-5-(trifluoromethyl) pyrazolo[1,5-a]pyrimidine-3-carboxamide (Compound I-O-5);

2-amino-N-(4-(cyclopropylmethoxy)pyridin-3-yl)-5-(trifluoromethyl)pyrazolo[1,5-a]pyrimidine-3-carboxamide (Compound I-O-6);

N-(4-(1,4-dioxaspiro[4.5]decan-8-yloxy)pyridin-3-yl)-2-amino-5-(trifluoromethyl)pyrazolo[1,5-a]pyrimidine-3-carboxamide (Compound I-O-7);

2-amino-N-(4-(2-methoxyethoxy)pyridin-3-yl)-5-(trifluoromethyl)pyrazolo[1,5-a]pyrimidine-3-carboxamide (Compound I-O-8);

(R)-2-amino-N-(4-((tetrahydrofuran-3-yl)oxy)pyridin-3-yl)-5-(trifluoromethyl)pyrazolo[1,5-a]pyrimidine-3-carboxamide (Compound I-O-9);

(S)-2-amino-N-(4-((tetrahydrofuran-3-yl)oxy)pyridin-3-yl)-5-(trifluoromethyl)pyrazolo[1,5-a]pyrimidine-3-carboxamide (Compound I-O-10);

2-amino-N-(4-((tetrahydro-2H-pyran-4-yl)oxy)pyridin-3-yl)-5-(trifluoromethyl)pyrazolo[1,5-a]pyrimidine-3-carboxamide (Compound I-O-11);

2-amino-N-(4-((tetrahydro-2H-pyran-3-yl)oxy)pyridin-3-yl)-5-(trifluoromethyl)pyrazolo[1,5-a]pyrimidine-3-carboxamide (Compound I-O-12);

2-amino-N-(4-(2-hydroxyethoxy)pyridin-3-yl)-5-(trifluoromethyl)pyrazolo[1,5-a]pyrimidine-3-carboxamide (Compound I-O-13);

2-amino-N-(4-(3-hydroxypropoxy)pyridin-3-yl)-5-(trifluoromethyl)pyrazolo[1,5-a]pyrimidine-3-carboxamide (Compound I-O-14);

2-amino-N-(4-(pyridin-3-yloxy)pyridin-3-yl)-5-(trifluoromethyl)pyrazolo[1,5-a]pyrimidine-3-carboxamide (Compound I-O-15);

2-amino-N-(4-(pyridin-4-yloxy)pyridin-3-yl)-5-(trifluoromethyl)pyrazolo[1,5-a]pyrimidine-3-carboxamide (Compound I-O-16);

2-amino-N-(4-(2-(dimethylamino)ethoxy)pyridin-3-yl)-5-(trifluoromethyl)pyrazolo[1,5-a]pyrimidine-3-carboxamide (Compound I-O-17);

2-amino-N-(4-(azetidin-3-yloxy)pyridin-3-yl)-5-(trifluoromethyl)pyrazolo[1,5-a]pyrimidine-3-carboxamide (Compound I-O-18);

(R)-2-amino-N-(4-((1-methylpyrrolidin-3-yl)oxy)pyridin-3-yl)-5-(trifluoromethyl)pyrazolo[1,5-a]pyrimidine-3-carboxamide (Compound I-O-19);

2-amino-N-(4-(2-morpholinoethoxy)pyridin-3-yl)-5-(trifluoromethyl)pyrazolo[1,5-a]pyrimidine-3-carboxamide (Compound I-20);

(S)-2-amino-N-(4-(pyrrolidin-3-yloxy)pyridin-3-yl)-5-(trifluoromethyl)pyrazolo[1,5-a]pyrimidine-3-carboxamide (Compound I-O-21);

N-(4-((4s,6r)-1-azaspiro[3.3]heptan-6-yloxy)pyridin-3-yl)-2-amino-5-(trifluoromethyl)pyrazolo[1,5-a]pyrimidine-3-carboxamide (Compound I-O-22);

2-amino-N-(4-(piperidin-3-yloxy)pyridin-3-yl)-5-(trifluoromethyl)pyrazolo[1,5-a]pyrimidine-3-carboxamide (Compound I-O-23);

N-(4-((4r,6s)-1-azaspiro[3.3]heptan-6-yloxy)pyridin-3-yl)-2-amino-5-(trifluoromethyl)pyrazolo[1,5-a]pyrimidine-3-carboxamide (Compound I-O-24);

(R)-2-amino-N-(4-(pyrrolidin-3-yloxy)pyridin-3-yl)-5-(trifluoromethyl)pyrazolo[1,5-a]pyrimidine-3-carboxamide (Compound I-O-25);

2-amino-N-(4-((1-methylpiperidin-3-yl)oxy)pyridin-3-yl)-5-(trifluoromethyl)pyrazolo[1,5-a]pyrimidine-3-carboxamide (Compound I-O-26);

2-amino-N-(4-(3-(dimethylamino)propoxy)pyridin-3-yl)-5-(trifluoromethyl)pyrazolo[1,5-a]pyrimidine-3-carboxamide (Compound I-O-27);

(R)-2-amino-N-(4-((1-methylpyrrolidin-2-yl)methoxy)pyridin-3-yl)-5-(trifluoromethyl)pyrazolo[1,5-a]pyrimidine-3-carboxamide (Compound I-O-28);

2-amino-N-(4-(quinuclidin-3-yloxy)pyridin-3-yl)-5-(trifluoromethyl)pyrazolo[1,5-a]pyrimidine-3-carboxamide (Compound I-O-29);

2-amino-N-(4-(((1s,4s)-4-(dimethylamino)cyclohexyl)oxy)pyridin-3-yl)-5-(trifluoromethyl)pyrazolo[1,5-a]pyrimidine-3-carboxamide (Compound I-O-30);

2-amino-N-(4-((1-methylpiperidin-4-yl)oxy)pyridin-3-yl)-5-(trifluoromethyl)pyrazolo[1,5-a]pyrimidine-3-carboxamide (Compound I-O-31);

N-(4-(2-azaspiro[3.3]heptan-6-yloxy)pyridin-3-yl)-2-amino-5-(trifluoromethyl)pyrazolo[1,5-a]pyrimidine-3-carboxamide (Compound I-O-32);

(S)-2-amino-N-(4-((1-methylpyrrolidin-2-yl)methoxy)pyridin-3-yl)-5-(trifluoromethyl)pyrazolo[1,5-a]pyrimidine-3-carboxamide (Compound I-O-33);

2-amino-N-(4-((1s,3s)-3-(dimethylamino)cyclobutoxy)pyridin-3-yl)-5-(trifluoromethyl)pyrazolo[1,5-a]pyrimidine-3-carboxamide (Compound I-O-34);

2-amino-N-(4-((4-(dimethylamino)cyclohexyl)oxy)pyridin-3-yl)-5-(trifluoromethyl)pyrazolo[1,5-a]pyrimidine-3-carboxamide (Compound I-O-35);

2-amino-N-(4-(2-(2-(dimethylamino)ethoxy)ethoxy)pyridin-3-yl)-5-(trifluoromethyl)pyrazolo[1,5-a]pyrimidine-3-carboxamide (Compound I-O-36);

2-amino-N-(4-((4-aminocyclohexyl)methoxy)pyridin-3-yl)-5-(trifluoromethyl)pyrazolo[1,5-a]pyrimidine-3-carboxamide (Compound I-O-37);

N-(4-(2-(2-oxa-6-azaspiro[3.3]heptan-6-yl)ethoxy)pyridin-3-yl)-2-amino-5-(trifluoromethyl)pyrazolo[1,5-a]pyrimidine-3-carboxamide (Compound I-O-38);

2-amino-N-(4-((1-methylazetidin-3-yl)oxy)pyridin-3-yl)-5-(trifluoromethyl)pyrazolo[1,5-a]pyrimidine-3-carboxamide (Compound I-O-39);

(S)-2-amino-N-(4-((1-methylpyrrolidin-3-yl)oxy)pyridin-3-yl)-5-(trifluoromethyl)pyrazolo[1,5-a]pyrimidine-3-carboxamide (Compound I-O-40);

2-amino-N-(4-(piperidin-4-yloxy)pyridin-3-yl)-5-(trifluoromethyl)pyrazolo[1,5-a]pyrimidine-3-carboxamide (Compound I-O-41);

2-amino-N-(4-((4-(dimethylamino)cyclohexyl)methoxy)pyridin-3-yl)-5-(trifluoromethyl)pyrazolo[1,5-a]pyrimidine-3-carboxamide (Compound I-O-42);

(R)-2-amino-N-(4-((1-(2-methoxyethyl)piperidin-3-yl)oxy)pyridin-3-yl)-5-(trifluoromethyl)pyrazolo[1,5-a]pyrimidine-3-carboxamide (Compound I-O-43);

2-amino-N-(4-(((1s,4s)-4-(dimethylamino)cyclohexyl)oxy)pyridin-3-yl)-5-(trifluoromethyl)pyrazolo[1,5-a]pyrimidine-3-carboxamide (Compound I-O-44);

2-amino-N-(4-((6-((dimethylamino)methyl)pyridin-3-yl)oxy)pyridin-3-yl)-5-(trifluoromethyl)pyrazolo[1,5-a]pyrimidine-3-carboxamide (Compound I-O-45);

2-amino-N-(4-methoxy-6-methylpyridin-3-yl)-5-(trifluoromethyl)pyrazolo[1,5-a]pyrimidine-3-carboxamide (Compound I-O-46);

2-amino-N-(6-chloro-4-methoxypyridin-3-yl)-5-(trifluoromethyl)pyrazolo[1,5-a]pyrimidine-3-carboxamide (Compound I-O-47);

2-amino-N-(5-chloro-4-methoxypyridin-3-yl)-5-(trifluoromethyl)pyrazolo[1,5-a]pyrimidine-3-carboxamide (Compound I-O-48);

2-amino-N-(5-chloro-4-((1-methylpiperidin-4-yl)oxy)pyridin-3-yl)-5-(trifluoromethyl)pyrazolo[1,5-a]pyrimidine-3-carboxamide (Compound I-O-49);

2-amino-N-(6-chloro-4-(2-(dimethylamino)ethoxy)pyridin-3-yl)-5-(trifluoromethyl)pyrazolo[1,5-a]pyrimidine-3-carboxamide (Compound I-O-50);

2-amino-N-(4-(2-(dimethylamino)ethoxy)-6-(trifluoromethyl)pyridin-3-yl)-5-(trifluoromethyl)pyrazolo[1,5-a]pyrimidine-3-carboxamide (Compound I-O-51);

2-amino-5-(2-cyanopropan-2-yl)-N-(4-methoxypyridin-3-yl)pyrazolo[1,5-a]pyrimidine-3-carboxamide (Compound I-O-52);

2-amino-N-(4-(azetidin-3-yloxy)pyridin-3-yl)-5-(2-cyanopropan-2-yl)pyrazolo[1,5-a]pyrimidine-3-carboxamide (Compound I-O-53);

2-amino-5-(hydroxymethyl)-N-(4-methoxypyridin-3-yl)pyrazolo[1,5-a]pyrimidine-3-carboxamide (Compound I-O-54);

5-((allyloxy)methyl)-2-amino-N-(4-methoxypyridin-3-yl)pyrazolo[1,5-a]pyrimidine-3-carboxamide (Compound I-O-55);

2-amino-N-(4-methoxypyridin-3-yl)-5-(oxetan-3-yloxy)pyrazolo[1,5-a]pyrimidine-3-carboxamide (Compound I-O-56);

2-amino-N-(4-methoxypyridin-3-yl)-5-((1-methylpyrrolidin-3-yl)oxy)pyrazolo[1,5-a]pyrimidine-3-carboxamide (Compound I-O-57);

2-amino-N-(4-methoxypyridin-3-yl)-5-((1-methylpiperidin-3-yl)oxy)pyrazolo[1,5-a]pyrimidine-3-carboxamide (Compound I-O-58);

2-amino-5-(2-(azetidin-1-yl)ethoxy)-N-(4-methoxypyridin-3-yl)pyrazolo[1,5-a]pyrimidine-3-carboxamide (Compound I-O-59);

2-amino-N-(4-methoxypyridin-3-yl)-5-(2-(pyrrolidin-1-yl)ethoxy)pyrazolo[1,5-a]pyrimidine-3-carboxamide (Compound I-O-60);

2-amino-N-(4-methoxypyridin-3-yl)-5-((1-methylpiperidin-4-yl)oxy)pyrazolo[1,5-a]pyrimidine-3-carboxamide (Compound I-O-61);

2-amino-5-(2-(dimethylamino)ethoxy)-N-(4-methoxypyridin-3-yl)pyrazolo[1,5-a]pyrimidine-3-carboxamide (Compound I-O-62);
2-amino-5-(3-(azetidin-1-yl)propoxy)-N-(4-methoxypyridin-3-yl)pyrazolo[1,5-a]pyrimidine-3-carboxamide (Compound I-O-63);
2-amino-5-(2-(dimethylamino)ethoxy)-N-(4-isopropoxypyridin-3-yl)pyrazolo[1,5-a]pyrimidine-3-carboxamide (Compound I-O-64);
2-amino-N-(6-chloro-4-methoxypyridin-3-yl)-5-(2-(dimethylamino)ethoxy)pyrazolo[1,5-a]pyrimidine-3-carboxamide (Compound I-O-65);
2-amino-N-(4-methoxypyridin-3-yl)-5-((methylamino)methyl)pyrazolo[1,5-a]pyrimidine-3-carboxamide (Compound I-O-66);
2-amino-N-(4-methoxypyridin-3-yl)-5-(propylamino)pyrazolo[1,5-a]pyrimidine-3-carboxamide (Compound I-O-67);
2-amino-N-(4-methoxypyridin-3-yl)-5-((oxetan-3-ylmethyl)amino)pyrazolo[1,5-a]pyrimidine-3-carboxamide (Compound I-O-68);
2-amino-N-(4-methoxypyridin-3-yl)-5-(2-oxa-6-azaspiro[3.3]heptan-6-yl)pyrazolo[1,5-a]pyrimidine-3-carboxamide (Compound I-O-69);
2-amino-5-((2-(dimethylamino)ethyl)amino)-N-(4-methoxypyridin-3-yl)pyrazolo[1,5-a]pyrimidine-3-carboxamide (Compound I-O-70);
2-amino-N-(4-methoxypyridin-3-yl)-5-(((1-methylpyrrolidin-2-yl)methyl)amino)pyrazolo[1,5-a]pyrimidine-3-carboxamide (Compound I-O-71);
2-amino-N-(4-methoxypyridin-3-yl)-5-((2-(pyrrolidin-1-yl)ethyl)amino)pyrazolo[1,5-a]pyrimidine-3-carboxamide (Compound I-O-72);
2-amino-N-(4-methoxypyridin-3-yl)-5-(methyl((1-methylpyrrolidin-2-yl)methyl)amino)pyrazolo[1,5-a]pyrimidine-3-carboxamide (Compound I-O-73);
2-amino-N-(4-methoxypyridin-3-yl)-5-(3-(trifluoromethyl)piperazin-1-yl)pyrazolo[1,5-a]pyrimidine-3-carboxamide (Compound I-O-74);
(R)-2-amino-5-(hexahydropyrrolo[1,2-a]pyrazin-2(1H)-yl)-N-(4-methoxypyridin-3-yl)pyrazolo[1,5-a]pyrimidine-3-carboxamide (Compound I-O-75);
2-amino-N-(4-methoxypyridin-3-yl)-5-(piperazin-1-yl)pyrazolo[1,5-a]pyrimidine-3-carboxamide (Compound I-O-76);
2-amino-N-(4-methoxypyridin-3-yl)-5-(3-methylpiperazin-1-yl)pyrazolo[1,5-a]pyrimidine-3-carboxamide (Compound I-O-77);
2-amino-N-(4-methoxypyridin-3-yl)-5-(4-methylpiperazin-1-yl)pyrazolo[1,5-a]pyrimidine-3-carboxamide (Compound I-O-78);
2-amino-N-(4-isopropoxypyridin-3-yl)-5-(4-methylpiperazin-1-yl)pyrazolo[1,5-a]pyrimidine-3-carboxamide (Compound I-O-79);
2-amino-5-(4-(dimethylamino)piperidin-1-yl)-N-(4-methoxypyridin-3-yl)pyrazolo[1,5-a]pyrimidine-3-carboxamide (Compound I-O-80);
2-amino-N-(4-methoxypyridin-3-yl)-5-(3-(methylamino)pyrrolidin-1-yl)pyrazolo[1,5-a]pyrimidine-3-carboxamide (Compound I-O-81);
2-amino-N-(4-methylpyridin-3-yl)-5-(trifluoromethyl)pyrazolo[1,5-a]pyrimidine-3-carboxamide (Compound I-C-1);
2-amino-N-(4-phenylpyridin-3-yl)-5-(trifluoromethyl)pyrazolo[1,5-a]pyrimidine-3-carboxamide (Compound I-C-2);
2-amino-5-(2-(dimethylamino)ethoxy)-N-(4-methylpyridin-3-yl)pyrazolo[1,5-a]pyrimidine-3-carboxamide (Compound I-C-3);
2-amino-N-(4-(4-methylpiperazin-1-yl)pyridin-3-yl)-5-(trifluoromethyl)pyrazolo[1,5-a]pyrimidine-3-carboxamide (Compound I-N-1);
2-amino-N-(4-(4-(aminomethyl)piperidin-1-yl)pyridin-3-yl)-5-(trifluoromethyl)pyrazolo[1,5-a]pyrimidine-3-carboxamide (Compound I-N-2); and
2-amino-N-(4-(4-(2-hydroxyethyl)piperazin-1-yl)pyridin-3-yl)-5-(trifluoromethyl)pyrazolo[1,5-a]pyrimidine-3-carboxamide (Compound I-N-3).

Compound Analytical Data

| Cmpds of formula I | LCMS ES+ | LCMS (Rt min) | HNMR |
|---|---|---|---|
| I-O-1 | 353.1 | 2.32 | $^1$H NMR (500 MHz, DMSO-d6) δ 9.94 (s, 1H), 9.56 (s, 1H), 9.27 (d, J = 6.9 Hz, 1H), 8.23 (d, J = 5.5 Hz, 1H), 7.51 (d, J = 6.9 Hz, 1H), 7.18 (d, J = 5.5 Hz, 1H), 7.00 (s, 2H), 4.00 (s, 3H). |
| I-O-2 | 367.0 | 2.52 | $^1$H NMR (500 MHz, DMSO-d6) δ 9.62 (s, 1H), 9.50 (s, 1H), 9.27 (dt, J = 6.8, 0.6 Hz, 1H), 8.21 (d, J = 5.5 Hz, 1H), 7.50 (d, J = 6.9 Hz, 1H), 7.18 (d, J = 5.6 Hz, 1H), 7.02 (s, 2H), 4.33 (q, J = 7.0 Hz, 2H), 1.40 (t, J = 7.0 Hz, 3H). |
| I-O-3 | 421.1 | 2.57 | $^1$H NMR (500 MHz, DMSO-d6) δ 9.56 (s, 1H), 9.49 (s, 1H), 9.27 (dt, J = 6.8, 0.6 Hz, 1H), 8.29 (d, J = 5.6 Hz, 1H), 7.50 (d, J = 6.9 Hz, 1H), 7.41 (d, J = 5.6 Hz, 1H), 7.02 (s, 2H), 5.05 (q, J = 8.7 Hz, 2H). |
| I-O-4 | 381.1 | 2.67 | $^1$H NMR (500 MHz, DMSO-d6) δ 9.42 (s, 1H), 9.37 (s, 1H), 9.30-9.24 (m, 1H), 8.20 (d, J = 5.6 Hz, 1H), 7.50 (d, J = 6.9 Hz, 1H), 7.20 (d, J = 5.6 Hz, 1H), 7.03 (s, 2H), 4.92 (p, J = 6.1 Hz, 1H), 1.36 (d, J = 6.0 Hz, 6H). |
| I-O-5 | 393.0 | 2.79 | $^1$H NMR (500 MHz, DMSO-d6) δ 9.46 (s, 1H), 9.43 (s, 1H), 9.27 (dd, J = 6.8, 0.6 Hz, 1H), 8.19 (d, J = 5.5 Hz, 1H), 7.51 (d, J = 6.9 Hz, 1H), 7.05-6.99 (m, 3H), 4.95 (p, J = 7.2 Hz, 1H), 2.16 (qdd, J = 10.0, 7.8, 2.8 Hz, 2H), 1.88-1.77 (m, 1H), 1.75 - 1.62 (m, 1H). |
| I-O-6 | 393.1 | 2.72 | $^1$H NMR (500 MHz, DMSO-d6) δ 9.66 (s, 1H), 9.51 (s, 1H), 9.30-9.24 (m, 1H), 8.20 (d, J = 5.5 Hz, 1H), 7.50 (d, J = 6.9 Hz, 1H), 7.22 (d, J = 5.6 Hz, 1H), 7.02 (s, 2H), 4.15 (d, J = 7.2 Hz, 2H), 1.38-1.27 (m, 1H), 0.61-0.53 (m, 2H), 0.41-0.34 (m, 2H). |

-continued

| Cmpds of formula I | LCMS ES+ | LCMS (Rt min) | HNMR |
|---|---|---|---|
| I-O-7 | 479.0 | 2.53 | ¹H (500 MHz, DMSO-d6) δ 9.54 (d, J = 1.0 Hz, 1H), 9.51 (s, 1H), 9.31 (d, J = 6.9 Hz, 1H), 8.56 (d, J = 6.7 Hz, 1H), 7.80 (d, J = 6.5 Hz, 1H), 7.56 (d, J = 6.9 Hz, 1H), 7.06 (s, 2H), 5.03 (dt, J = 9.6, 5.2 Hz, 1H), 3.88 (s, 4H), 2.04 (dd, J = 12.4, 4.5 Hz, 2H), 1.97-1.81 (m, 2H), 1.79-1.61 (m, 4H). |
| I-O-8 | 397.1 | 2.30 | ¹H NMR (500 MHz, DMSO-d6) δ 9.60 (s, 1H), 9.47 (s, 1H), 9.27 (dd, J = 6.9, 0.6 Hz, 1H), 8.21 (d, J = 5.5 Hz, 1H), 7.51 (d, J = 6.9 Hz, 1H), 7.23 (d, J = 5.6 Hz, 1H), 7.02 (s, 2H), 4.45-4.39 (m, 2H), 3.76-3.70 (m, 2H), 3.25 (s, 3H). |
| I-O-9 | 409.3 | 2.23 | ¹H NMR (500 MHz, DMSO-d6) δ 9.39 (s, 1H), 9.27 (dd, J = 6.9, 0.7 Hz, 1H), 9.24 (s, 1H), 8.23 (d, J = 5.6 Hz, 1H), 7.50 (d, J = 6.9 Hz, 1H), 7.16 (d, J = 5.6 Hz, 1H), 7.04 (s, 2H), 5.27 (ddt, J = 7.1, 4.7, 2.1 Hz, 1H), 4.03 (dd, J = 10.4, 5.0 Hz, 1H), 3.87-3.73 (m, 3H), 2.40-2.29 (m, 1H), 2.12-2.02 (m, 1H). |
| I-O-10 | 409.0 | 2.22 | ¹H NMR (500 MHz, DMSO-d6) δ 9.39 (s, 1H), 9.29-9.24 (m, 1H), 9.23 (s, 1H), 8.23 (d, J = 5.6 Hz, 1H), 7.50 (d, J = 6.9 Hz, 1H), 7.15 (d, J = 5.6 Hz, 1H), 7.04 (s, 2H), 5.27 (ddt, J = 7.2, 4.7, 2.1 Hz, 1H), 4.03 (dd, J = 10.4, 5.0 Hz, 1H), 3.88-3.73 (m, 3H), 2.34 (dtd, J = 13.4, 7.9, 6.6 Hz, 1H), 2.12-2.02 (m, 1H). |
| I-O-11 | 423.1 | 2.30 | ¹H NMR (500 MHz, DMSO-d6) δ 9.38 (s, 1H), 9.35 (s, 1H), 9.27 (dt, J = 6.8, 0.6 Hz, 1H), 8.21 (d, J = 5.6 Hz, 1H), 7.51 (d, J = 6.9 Hz, 1H), 7.31 (d, J = 5.7 Hz, 1H), 7.03 (s, 2H), 4.87 (tt, J = 9.2, 4.3 Hz, 1H), 3.88 (dt, J = 11.6, 4.1 Hz, 2H), 3.49 (ddd, J = 11.7, 10.4, 2.5 Hz, 2H), 2.03 (ddt, J = 14.7, 4.4, 2.5 Hz, 2H), 1.69 (dtd, J = 13.4, 9.9, 4.3 Hz, 2H). |
| I-O-12 | 423.1 | 2.43 | ¹H NMR (500 MHz, DMSO-d6) δ 9.34 (s, 1H), 9.31-9.25 (m, 2H), 8.21 (d, J = 5.6 Hz, 1H), 7.51 (d, J = 6.9 Hz, 1H), 7.30 (d, J = 5.6 Hz, 1H), 7.03 (s, 2H), 4.68 (td, J = 8.1, 3.8 Hz, 1H), 3.94 (ddd, J = 11.3, 3.9, 1.6 Hz, 1H), 3.74 (dt, J = 11.4, 4.0 Hz, 1H), 3.43 (dd, J = 11.2, 7.9 Hz, 1H), 3.36 (ddd, J = 10.7, 9.5, 2.8 Hz, 1H), 2.23-2.15 (m, 1H), 1.81-1.57 (m, 3H). |
| I-O-13 | 383.0 | 1.91 | ¹H NMR (500 MHz, DMSO-d6) δ 9.96 (s, 1H), 9.64 (d, J = 0.9 Hz, 1H), 9.32 (d, J = 6.9 Hz, 1H), 8.54 (dd, J = 6.5, 1.0 Hz, 1H), 7.74 (d, J = 6.5 Hz, 1H), 7.57 (d, J = 6.9 Hz, 1H), 7.13-6.98 (m, 2H), 5.02 (s, 1H), 4.58 (t, J = 5.0 Hz, 2H), 3.84 (t, J = 5.0 Hz, 2H). |
| I-O-14 | 397.0 | 2.00 | ¹H NMR (500 MHz, DMSO-d6) δ 9.80 (s, 1H), 9.63 (d, J = 1.0 Hz, 1H), 9.32 (d, J = 6.9 Hz, 1H), 8.61-8.47 (m, 1H), 7.69 (d, J = 6.4 Hz, 1H), 7.57 (d, J = 6.9 Hz, 1H), 7.06 (s, 2H), 4.58 (t, J = 6.7 Hz, 2H), 3.53 (t, 2H), 2.01 (m, 2H). |
| I-O-15 | 416.0 | 2.26 | ¹H NMR (500 MHz, DMSO-d6) δ 10.34 (s, 1H), 9.79 (s, 1H), 9.38-9.19 (m, 1H), 8.72-8.59 (m, 2H), 8.37 (d, J = 6.0 Hz, 1H), 7.86 (ddd, J = 8.4, 2.8, 1.4 Hz, 1H), 7.64 (ddd, J = 8.4, 4.8, 0.6 Hz, 1H), 7.49 (d, J = 6.9 Hz, 1H), 7.06 (d, J = 6.2 Hz, 2H). |
| I-O-16 | 416.0 | 1.58 | ¹H NMR (500 MHz, DMSO-d6) δ 9.17 (s, 1H), 9.12 (s, 1H), 8.55 (s, 1H), 7.87 (d, J = 7.8 Hz, 2H), 7.56 (s, 1H), 7.42 (s, 1H), 6.23 (d, J = 7.8 Hz, 2H). |
| I-O-17 | 410.1 | 2.21 | ¹H NMR (500 MHz, DMSO-d6) δ 9.55 (s, 1H), 9.46 (s, 1H), 9.30-9.25 (m, 1H), 8.22 (d, J = 5.5 Hz, 1H), 7.51 (d, J = 6.9 Hz, 1H), 7.23 (d, J = 5.6 Hz, 1H), 7.03 (s, 2H), 4.34 (t, J = 6.4 Hz, 2H), 2.69 (t, J = 6.4 Hz, 2H), 2.19 (s, 6H). |
| I-O-18 | 394.1 | 1.88 | ¹H NMR (500 MHz, DMSO-d6) δ 9.47 (d, J = 9.9 Hz, 2H), 9.28 (d, J = 6.9 Hz, 1H), 8.19 (d, J = 5.5 Hz, 1H), 7.51 (d, J = 6.9 Hz, 1H), 7.03 (s, 2H), 6.89 (d, J = 5.5 Hz, 1H), 5.22 (p, J = 6.2 Hz, 1H), 3.89-3.79 (m, 2H), 3.67-3.60 (m, 2H). |
| I-O-19 | 422.1 | 2.30 | ¹H NMR (500 MHz, DMSO-d6) δ 9.56 (s, 1H), 9.34 (s, 1H), 9.33 (s, 1H), 8.59 (d, J = 6.0 Hz, 1H), 7.66-7.63 (m, 1H), 7.59 (d, J = 7.0 Hz, 1H), 7.09 (brs, 2H), 5.64 (br s, 1H), 3.89-3.26 (br m, 4H), 2.86 (s, 3H), 2.50 (masked signal, 1H), 2.38-2.36 (br m, 1H). |
| I-O-20 | 452.1 | 2.10 | ¹H NMR (500 MHz, DMSO-d6) δ 9.67 (s, 1H), 9.62 (s, 1H), 9.32 (d, J = 7.1 Hz, 1H), 8.64 (d, J = 6.4 Hz, 1H), 7.74 (d, J = 6.4 Hz, 1H), 7.57 (dd, J = 6.7, 1.5 Hz, 1H), 7.06 (br s, 2H), 4.88-4.86 (m, 2H), 3.75 (br s, 4H), 3.68-3.56 (br m, 2H), 3.22 (br s, 4H). |

| Cmpds of formula I | LCMS ES+ | LCMS (Rt min) | HNMR |
|---|---|---|---|
| I-O-21 | 408.1 | 1.95 | ¹H NMR (500 MHz, DMSO-d6) δ 9.36 (s, 1H), 9.29-9.25 (m, 1H), 9.22 (s, 1H), 8.22 (d, J = 5.5 Hz, 1H), 7.50 (d, J = 6.9 Hz, 1H), 7.14 (d, J = 5.6 Hz, 1H), 7.03 (s, 2H), 5.07 (ddt, J = 8.2, 5.6, 2.6 Hz, 1H), 3.18 (dd, J = 12.5, 5.7 Hz, 1H), 2.94-2.84 (m, 2H), 2.79 (m, J = 10.9, 8.0, 4.9 Hz, 1H), 2.18-2.07 (m, 1H), 1.87 (m, J = 13.3, 7.6, 4.9, 2.4 Hz, 1H). |
| I-O-22 | 434.0 | 2.02 | ¹H NMR (500 MHz, DMSO-d6) δ 9.61 (s, 1H), 9.52 (s, 1H), 9.33 (d, J = 6.9 Hz, 1H), 9.03 (s, 2H), 8.51 (d, J = 5.3 Hz, 1H), 7.58 (d, J = 7.0 Hz, 1H), 7.23 (s, 1H), 7.08 (s, 2H), 5.28-5.16 (m, 1H), 3.82 (ddt, J = 12.0, 7.9, 4.0 Hz, 2H), 3.31 (dd, J = 15.0, 7.1 Hz, 2H), 2.66-2.58 (m, 2H), 2.52 (m, 2H). |
| I-O-23 | 422.1 | 2.13 | ¹H NMR (500 MHz, DMSO-d6) δ 9.36 (s, 1H), 9.32 (s, 1H), 9.27 (d, J = 6.9 Hz, 1H), 8.20 (d, J = 5.6 Hz, 1H), 7.50 (d, J = 6.9 Hz, 1H), 7.24 (d, J = 5.7 Hz, 1H), 7.02 (s, 2H), 4.52 (ddt, J = 13.6, 9.2, 4.2 Hz, 1H), 3.20-3.13 (m, 1H), 2.87-2.76 (m, 1H), 2.49-2.27 (m, 2H), 2.13 (dd, J = 10.2, 5.0 Hz, 1H), 1.73-1.64 (m, 1H), 1.53 (m, 2H). |
| I-O-24 | 434.0 | 2.02 | ¹H NMR (500 MHz, DMSO-d6) δ 9.66-9.54 (m, 1H), 9.33 (d, J = 6.9 Hz, 1H), 9.15 (d, J = 19.2 Hz, 2H), 8.52 (d, J = 6.7 Hz, 1H), 7.58 (d, J = 6.9 Hz, 1H), 7.43 (d, J = 4.9 Hz, 1H), 7.08 (s, 2H), 5.02 (d, J = 5.7 Hz, 1H), 3.91-3.74 (m, 2H), 3.14 (d, J = 19.8 Hz, 2H), 2.76 (s, 2H), 2.65 (dd, J = 8.9, 7.6 Hz, 2H). |
| I-O-25 | 408.1 | 1.95 | ¹H NMR (500 MHz, DMSO-d6) δ 9.36 (s, 1H), 9.27 (d, J = 6.9 Hz, 1H), 9.22 (s, 1H), 8.22 (d, J = 5.5 Hz, 1H), 7.50 (d, J = 6.9 Hz, 1H), 7.14 (d, J = 5.6 Hz, 1H), 7.03 (s, 2H), 5.07 (tt, J = 5.4, 2.8 Hz, 1H), 3.19 (dd, J = 12.5, 5.7 Hz, 1H), 2.89 (ddd, J = 13.6, 11.1, 5.2 Hz, 2H), 2.80 (ddd, J = 10.7, 8.0, 5.0 Hz, 1H), 2.13 (dq, J = 14.6, 7.4 Hz, 1H), 1.87 (m, 1H). |
| I-O-26 | 436.2 | 2.38 | ¹H NMR (500 MHz, DMSO-d6) δ 9.38 (s, 1H), 9.30 (s, 1H), 9.27 (d, J = 6.9 Hz, 1H), 8.20 (d, J = 5.6 Hz, 1H), 7.50 (d, J = 6.9 Hz, 1H), 7.27 (d, J = 5.7 Hz, 1H), 7.03 (s, 2H), 4.73-4.58 (m, 1H), 3.08-2.93 (m, 1H), 2.73-2.65 (m, 1H), 2.19 (s, 3H), 2.15-2.08 (m, 1H), 2.08-2.02 (m, 1H), 1.93-1.83 (m, 1H), 1.81-1.68 (m, 1H), 1.68-1.54 (m, 1H), 1.44-1.27 (m, 1H). |
| I-O-27 | 424.1 | 2.25 | ¹H NMR (500 MHz, DMSO-d6) δ 9.57 (s, 1H), 9.46 (s, 1H), 9.26 (d, J = 6.9 Hz, 1H), 8.20 (d, J = 5.7 Hz, 1H), 7.49 (d, J = 7.0 Hz, 1H), 7.18 (d, J = 5.7 Hz, 1H), 7.02 (s, 2H), 4.29 (t, J = 7.0 Hz, 2H), 2.32 (t, J = 6.9 Hz, 2H), 2.10 (s, 6H), 1.91 (p, J = 7.0 Hz, 2H). |
| I-O-28 | 436.2 | 2.36 | ¹H NMR (500 MHz, DMSO-d6) δ 1.55-1.66 (3H, m), 1.87-1.91 (1H, m), 2.15 (1H, m), 2.31 (3H, s), 2.68 (1H, m), 2.93 (1H, m), 4.05-4.09 (1H, m), 4.29-4.33 (1H, m), 7.02 (2H, br s), 7.22 (1H, m), 7.51 (1H, m), 8.22 (1H, m), 9.26 (1H, m), 9.38 (1H, s) and 9.48 (1H, br s) |
| I-O-29 | 448.0 | 2.15 | ¹H NMR (500 MHz, DMSO-d6) δ 10.10 (s, 1H), 9.37 (s, 1H), 9.32 (d, J = 6.8 Hz, 1H), 9.26 (s, 1H), 8.54 (d, J = 6.1 Hz, 1H), 7.56 (d, J = 6.9 Hz, 1H), 7.51 (d, J = 5.6 Hz, 1H), 7.06 (s, 2H), 5.33-5.21 (m, 1H), 3.98-3.82 (m, 1H), 3.34 (d, J = 13.8 Hz, 1H), 3.31-3.13 (m, 3H), 2.05 (d, J = 18.3 Hz, 1H), 1.94 (d, J = 5.3 Hz, 1H), 1.74 (d, J = 7.1 Hz, 1H). |
| I-O-30 | 464.0 | 2.26 | ¹H NMR (500 MHz, CDCl3) δ 9.60 (s, 1H), 9.36 (s, 1H), 8.68 (d, J = 6.9 Hz, 1H), 8.30 (d, J = 5.6 Hz, 1H), 7.19 (d, J = 6.9 Hz, 1H), 6.88 (d, J = 5.6 Hz, 1H), 6.04 (s, 2H), 4.44 (d, J = 10.5 Hz, 1H), 2.96 (s, 1H), 2.73 (s, 4H), 2.36 (m, 3H), 1.71 (s, |
| I-O-31 | 436.1 | 2.16 | ¹H NMR (500 MHz, DMSO-d6) δ 9.34 (d, J = 12.9 Hz, 2H), 9.27 (dd, J = 6.8, 0.6 Hz, 1H), 8.20 (d, J = 5.6 Hz, 1H), 7.51 (d, J = 6.9 Hz, 1H), 7.25 (d, J = 5.7 Hz, 1H), 7.03 (s, 2H), 4.61 (tt, J = 9.2, 3.9 Hz, 1H), 2.71-2.62 (m, 2H), 2.18-2.08 (m, 5H), 2.03-1.95 (m, 2H), 1.78-1.67 (m, 2H). |
| I-O-32 | 434.0 | 1.84 | ¹H NMR (500 MHz, DMSO-d6) δ 9.62 (s, 1H), 9.57 (s, 1H), 9.36-9.28 (m, 1H), 8.78 (s, 2H), 8.53 (d, J = 6.2 Hz, 1H), 7.58 (d, J = 6.9 Hz, 1H), 7.48-7.33 (m, 1H), 7.08 (s, 2H), 5.09 (t, J = 7.0 Hz, 1H), 4.11 (t, J = 6.1 Hz, 2H), 3.96 (t, J = 6.1 Hz, 2H), 2.96 (ddd, J = 10.3, 6.9, 3.3 Hz, 2H), 2.48-2.36 (m, 2H). |

| Cmpds of formula I | LCMS ES+ | LCMS (Rt min) | HNMR |
|---|---|---|---|
| I-O-33 | 436.3 | 2.39 | ¹H NMR (500 MHz, DMSO-d6) δ 1.62 (3H, m), 1.86 (1H, m), 2.15 (1H, m), 2.32 (3H, s), 2.70 (1H, m), 2.94 (1H, m), 4.08 (1H, m), 4.31 (1H, m), 7.02 (2H, br s), 7.22 (1H, m), 7.50 (1H, d), 8.22 (1H, m), 9.26 (1H, m), 9.38 (1H, s) and 9.48 (1H, s) |
| I-O-34 | 436.0 | 2.43 | ¹H NMR (500 MHz, DMSO-d6) δ 9.48 (s, 1H), 9.40 (s, 1H), 9.26 (dd, J = 6.9, 0.6 Hz, 1H), 8.19 (d, J = 5.5 Hz, 1H), 7.50 (d, J = 6.9 Hz, 1H), 7.06-6.98 (m, 3H), 4.67 (p, J = 7.1 Hz, 1H), 2.75-2.67 (m, 2H), 2.39 (tt, J = 7.9, 6.6 Hz, 1H), 2.05 (s, 7H), 1.95 (dt, J = 11.6, 8.6 Hz, 2H). |
| I-O-35 | 464.0 | 2.21 | — |
| I-O-36 | 454.1 | 2.16 | ¹H NMR (500 MHz, DMSO-d6) δ 9.62 (s, 1H), 9.45 (s, 1H), 9.28 (d, J = 6.9 Hz, 1H), 8.21 (d, J = 5.5 Hz, 1H), 7.51 (d, J = 6.9 Hz, 1H), 7.24 (d, J = 5.6 Hz, 1H), 7.01 (s, 2H), 4.44-4.38 (m, 2H), 3.80-3.74 (m, 2H), 3.46 (t, J = 6.0 Hz, 2H), 2.27 (t, J = 6.0 Hz, 2H), 1.99 (s, 6H). |
| I-O-37 | 450.0 | 2.01 | ¹H NMR (500 MHz, DMSO-d6) δ 9.53 (s, 1H), 9.40 (s, 1H), 9.27 (d, J = 6.7 Hz, 1H), 8.21 (d, J = 5.6 Hz, 1H), 7.50 (d, J = 6.9 Hz, 1H), 7.19 (d, J = 5.6 Hz, 1H), 7.01 (s, 2H), 4.08 (d, J = 6.5 Hz, 2H), 2.43 (ddt, J = 10.3, 7.2, 3.7 Hz, 1H), 1.75 (tdd, J = 14.2, 8.8, 3.7 Hz, 5H), 1.39 (s, 2H), 1.04-0.85 (m, 4H). |
| I-O-38 | 464.1 | 2.05 | ¹H NMR (500 MHz, DMSO-d6) δ 9.51 (s, 1H), 9.44 (s, 1H), 9.29 (d, J = 6.5 Hz, 1H), 8.21 (d, J = 5.6 Hz, 1H), 7.52 (d, J = 6.9 Hz, 1H), 7.17 (d, J = 5.6 Hz, 1H), 7.03 (s, 2H), 4.46 (s, 4H), 4.20 (t, J = 5.9 Hz, 2H), 3.29 (s, 4H), 2.75 (t, J = 5.8 Hz, 2H). |
| I-O-39 | 408.1 | 1.97 | ¹H NMR (500 MHz, DMSO-d6) δ 9.08 (d, J = 9.0 Hz, 1H), 7.98 (br s, 2H), 7.27 (d, J = 6.9 Hz, 1H), 7.16 (s, 1H), 7.04 (s, 1H), 6.41-6.34 (br m, 2H), 4.80-4.76 (m, 1H), 3.94 (br s, 1H), 3.78 (dd, J = 14.7, 4.2 Hz, 1H), 3.70-3.40 (br s, 2H), 3.18 (s, 3H). |
| I-O-40 | 422.1 | 2.30 | ¹H NMR (500 MHz, DMSO-d6) δ 9.56 (s, 1H), 9.34 (s, 1H), 9.33 (s, 1H), 8.59 (d, J = 6.0 Hz, 1H), 7.66-7.63 (m, 1H), 7.59 (d, J = 7.0 Hz, 1H), 7.09 (brs, 2H), 5.64 (br s, 1H), 3.89-3.26 (br m, 4H), 2.86 (s, 3H), 2.50 (masked signal, 1H), 2.38-2.36 (br m, 1H). |
| I-O-41 | 422.1 | 1.92 | ¹H NMR (500 MHz, DMSO-d6) δ 9.34 (d, J = 8.5 Hz, 2H), 9.26 (d, J = 6.9 Hz, 1H), 8.19 (d, J = 5.6 Hz, 1H), 7.50 (d, J = 6.9 Hz, 1H), 7.24 (d, J = 5.7 Hz, 1H), 7.02 (s, 2H), 4.67 (tt, J = 9.4, 4.2 Hz, 1H), 2.95 (dt, J = 12.4, 4.2 Hz, 2H), 2.60 (ddd, J = 13.0, 10.7, 2.7 Hz, 2H), 1.97 (dq, J = 11.8, 3.8 Hz, 2H), 1.55 (dtd, J = 14.1, 10.3, 4.0 Hz, 2H). |
| I-O-42 | 478.0 | 2.21 | — |
| I-O-43 | 480.2 | 2.47 | ¹H NMR (500 MHz, DMSO-d6) δ 9.39 (s, 1H), 9.30 (s, 1H), 9.27 (d, J = 6.8 Hz, 1H), 8.20 (d, J = 5.6 Hz, 1H), 7.51 (d, J = 6.9 Hz, 1H), 7.27 (d, J = 5.7 Hz, 1H), 7.03 (s, 2H), 4.74-4.57 (m, 1H), 3.42 (d, J = 5.9 Hz, 1H), 3.36 (td, J = 5.7, 1.5 Hz, 1H), 3.21 (s, 3H), 3.13 (d, J = 20.5 Hz, 1H), 2.96 (d, J = 4.3 Hz, 1H), 2.82 (d, J = 10.9 Hz, 1H), 2.32 (td, J = 9.0, 7.4 Hz, 1H), 2.22-2.06 (m, 2H), 1.99 (t, J = 12.6 Hz, 1H), 1.71 (d, J = 3.6 Hz, 1H), 1.60 (d, J = 13.8 Hz, 1H), 1.47-1.29 (m, 1H). |
| I-O-44 | 464.0 | 2.22 | ¹H NMR (500 MHz, CDCl3) δ 9.28 (s, 1H), 9.23 (s, 1H), 8.68 (d, J = 5.7 Hz, 1H), 8.33 (d, J = 5.7 Hz, 1H), 7.17 (d, J = 6.9 Hz, 1H), 6.88 (d, J = 5.7 Hz, 1H), 5.99 (d, J = 14.9 Hz, 2H), 4.73 (s, 1H), 2.58 (s, 1H), 2.28 (s, 8H), 1.83-1.63 (m, 7H). |
| I-O-45 | 473.0 | 2.28 | ¹H NMR (500 MHz, DMSO-d6) δ 10.14 (s, 1H), 9.70 (s, 1H), 9.26 (d, J = 6.9 Hz, 1H), 8.46 (d, J = 2.8 Hz, 1H), 8.20 (d, J = 5.5 Hz, 1H), 7.71 (dd, J = 8.5, 2.8 Hz, 1H), 7.60-7.53 (m, 1H), 7.44 (d, J = 6.9 Hz, 1H), 7.03 (s, 2H), 6.79 (d, J = 5.5 Hz, 1H), 3.59 (s, 2H), 2.22 (s, 6H). |
| I-O-46 | 367.1 | 2.47 | ¹H NMR (500 MHz, DMSO-d6) δ 10.14 (s, 1H), 9.47 (s, 1H), 9.32 (d, J = 6.9 Hz, 1H), 7.65 (s, 1H), 7.58 (d, J = 6.9 Hz, 1H), 7.03 (s, 2H), 4.19 (s, 3H), 2.65 (s, 3H). |
| I-O-47 | 387.0 | 2.70 | ¹H NMR (500 MHz, DMSO-d6) δ 9.94 (s, 1H), 9.35 (s, 1H), 9.28 (dd, J = 6.9, 0.6 Hz, 1H), 7.52 (d, J = 6.9 Hz, 1H), 7.31 (s, 1H), 7.00 (s, 2H), 4.04 (s, 3H). |

| Cmpds of formula I | LCMS ES+ | LCMS (Rt min) | HNMR |
|---|---|---|---|
| I-O-48 | 387.0 | 2.84 | ¹H NMR (500 MHz, DMSO-d6) δ 4.04 (3H, s), 7.05 (2H, br s), 7.44 (1H, m), 8.38 (1H, s), 9.30 (1H, m), 9.64 (1H, s) and 9.95 (1H, s) ppm. |
| I-O-49 | 470.1 | 2.66 | ¹H NMR (500 MHz, Methanol-d4) δ 2.02 (2H, m), 2.36 (2H, m), 2.81-2.88 (3H, m), 3.09 (1H, m), 3.44 (2H, m), 3.53 (2H, m), 4.67 (1H, m), 7.45 (1H, d), 8.46 (1H, m), 9.08 (1H, m) and 9.43 (1H, m) ppm. |
| I-O-50 | 444.1 | 2.55 | ¹H NMR (500 MHz, DMSO-d6) δ 9.77 (s, 1H), 9.43 (s, 1H), 9.31 (d, J = 6.9 Hz, 1H), 9.22 (s, 1H), 7.55 (d, J = 6.9 Hz, 1H), 7.46 (s, 1H), 7.04 (s, 2H), 4.68 (t, J = 5.3 Hz, 2H), 3.60-3.50 (m, 2H), 2.82 (s, 6H). |
| I-O-51 | 478.2 | 2.82 | ¹H NMR (500 MHz, DMSO-d6) δ 9.73 (s, 1H), 9.64 (s, 1H), 9.33-9.25 (m, 1H), 7.72 (s, 1H), 7.54 (d, J = 6.9 Hz, 1H), 7.06 (s, 2H), 4.49 (t, J = 6.3 Hz, 2H), 2.71 (t, J = 6.3 Hz, 2H), 2.19 (s, 6H). |
| I-O-52 | 352.1 | 2.08 | ¹H NMR (500 MHz, DMSO-d6) δ 9.77 (s, 1H), 9.50 (s, 1H), 9.05 (d, J = 7.0 Hz, 1H), 8.23 (d, J = 5.5 Hz, 1H), 7.26 (d, J = 7.0 Hz, 1H), 7.19 (d, J = 5.5 Hz, 1H), 6.76 (s, 2H), 4.01 (s, 3H), 1.87 (s, 6H). |
| I-O-53 | 393.0 | 1.72 | ¹H NMR (500 MHz, Methanol-d4) δ 9.80 (s, 1H), 9.61 (d, J = 2.3 Hz, 1H), 8.81 (dd, J = 7.1, 1.0 Hz, 1H), 8.52 (d, J = 6.5 Hz, 1H), 7.45 (d, J = 6.6 Hz, 1H), 7.21 (d, J = 7.1 Hz, 1H), 5.65-5.57 (m, 1H), 4.76-4.68 (m, 2H), 4.53 (dd, J = 12.6, 5.0 Hz, 2H), 1.88 (s, 6H). |
| I-O-54 | 315.2 | 1.54 | ¹H NMR (500 MHz, DMSO-d6) δ 10.23 (s, 1H), 9.52 (s, 1H), 8.94 (d, J = 6.9 Hz, 1H), 8.21 (d, J = 5.5 Hz, 1H), 7.16 (d, J = 5.5 Hz, 1H), 7.14 (d, J = 6.9 Hz, 1H), 6.58 (s, 2H), 5.77 (t, J = 6.0 Hz, 1H), 4.71 (d, J = 6.0 Hz, 2H), 4.03 (s, 3H). |
| I-O-55 | 355.2 | 2.25 | ¹H NMR (500 MHz, DMSO-d6) δ 10.19 (s, 1H), 9.52 (s, 1H), 8.95 (d, J = 6.9 Hz, 1H), 8.21 (d, J = 5.5 Hz, 1H), 7.16 (d, J = 5.5 Hz, 1H), 7.09 (d, J = 6.9 Hz, 1H), 6.62 (s, 2H), 6.01 (ddt, J = 17.3, 10.6, 5.4 Hz, 1H), 5.37 (dq, J = 17.3, 1.8 Hz, 1H), 5.24 (ddt, J = 10.5, 2.0, 1.3 Hz, 1H), 4.71 (s, 2H), 4.18 (dt, J = 5.4, 1.5 Hz, 2H), 4.03 (s, 3H). |
| I-O-56 | 357.3 | 1.79 | ¹H NMR (500 MHz, DMSO-d6) δ 4.65-4.7 (2H, m), 4.67-4.7 (2H, m), 4.95-5.0 (2H, m), 5.9-5.95 (1H, m), 6.45 (2H, brs), 6.67 (1H, d), 7.62-7.65 (1H, m), 8.1 (1H, brs), 8.55 (1H, s), 8.82 (1H, d), 9.47 (1H, s), 9.65 (1H, s). |
| I-O-57 | 384.2 | 1.95 | ¹H NMR (500 MHz, DMSO-d6) δ 2.2-2.3 (1H, m), 2.7-2.8 (1H, m), 2.95 (3H, s), 3.2-3. (1H, m), 3.35-3.4 (1H, m), 3.65-3.7 (1H, m), 3.98-4.02 (1H, m), 4.2 (3H, s), 5.8 (1H, brs), 6.4-6.63 (3H, m), 7.6-7.65 (1H, m), 8.55 (1H, d), 8.9 (1H, d), 9.55 (1H, s), 9.6 (1H, s), 10.35 (1H, brs). |
| I-O-58 | 398.2 | 2.08 | ¹H NMR (500 MHz, METHANOL-D4) δ 1.95-2.03 (2H, m), 2.2-2.3 (1H, m), 2.4-2.5 (1H, m), 2.96 (3H, s), 3.15-3.22 (1H, m), 3.5-3.55 (1H, m), 3.58-3.63 (1H, m), 3.95-4.02 (1H, m), 4.35 (3H, s), 5.85 (1H, s), 6.62 (1H, d), 7.7 (1H, d), 8.48-8.52 (1H, m), 8.62 (1H, d), 9.82 (1H, brs). |
| I-O-59 | 384.2 | 1.95 | ¹H NMR (500 MHz, DMSO-d6) δ 2.25-2.35 (2H, m), 3.7-3.73 (2H, m), 4.12 (3H, s), 4.18-4.23 (4H, m), 4.7-4.73 (2H, m), 6.45 (2H, brs), 6.58 (1H, d), 7.62-7.65 (1H, m), 8.48-8.53 (1H, m), 8.82 (1H, d), 9.65 (2H, brs), 10.15 (1H, brs). |
| I-O-60 | 398.2 | 2.00 | ¹H NMR (500 MHz, DMSO-d6) δ 1.9-1.95 (2H, m), 2.02-2.08 (2H, m), 3.15-3.2 (2H, m), 3.67-3.72 (2H, m), 3.75-3.8 (2H, m), 4.18 (3H, s), 4.84-4.88 (2H, m), 6.5 (2H, brs), 6.62 (1H, d), 7.7 (1H, d), 8.58 (1H, d), 8.85 (1H, d), 9.65 (1H, s), 9.7 (1H, s), 9.9 (1H, brs). |
| I-O-61 | 398.3 | 1.96 | ¹H NMR (500 MHz, DMSO-d6) δ 2.25-2.35 (2H, m), 2.4-2.5 (2H, m), 2.98 (3H, s), 3.3-3.55 (5H, m), 4.3 (3H, s), 5.7 (1H, s), 6.6 (1H, d), 7.67-7.71 (1H, m), 8.47 (1H, s), 8.6 (1H, d), 9.8 (1H, s). |
| I-O-62 | 372.2 | 1.93 | ¹H NMR (500 MHz, DMSO-d6) δ 2.8 (6H, s), 3.66-3.69 (2H, m), 4.13 (3H, s), 4.85-4.88 (2H, m), 6.47 (2H, brs), 6.5 (1H, d), 7.65-7.67 (1H, m), 8.53-8.56 (1H, m), 8.87 (1H, d), 9.65 (1H, s), 9.68 (1H, s). |
| I-O-63 | 398.2 | 1.97 | ¹H NMR (500 MHz, DMSO-d6) δ 2.02-2.07 (2H, m), 2.28-2.37 (2H, m), 3.35-3.4 (2H, m), 4.0-4.08 (2H, m), 4.15 (3H, s), 4.15-4.21 (4H, m), 4.6-4.63 (2H, m), 6.47 |

| Cmpds of formula I | LCMS ES+ | LCMS (Rt min) | HNMR |
|---|---|---|---|
| | | | (2H, brs), 6.58 (1H, d), 7.62-7.65 (1H, m), 8.53-8.58 (1H, m), 8.82 (1H, d), 9.65 (2H, brs), 9.75 (1H, brs). |
| I-O-64 | 400.2 | 2.18 | ¹H NMR (500 MHz, DMSO-d6) δ 1.4 (6H, d), 2.95 (6H, s), 3.58-32.6 (2H, m), 4.78-4.81 (2H, m), 5.04-5.07 (1H, m), 6.5 (2H, brs), 6.62 1H, d), 7.62 (1H, d), 8.5 (1H, d), 8.85 (1H, d), 9.3 (1H, brs), 9.35 (1H, brs), 9.8 (1H, brs). |
| I-O-65 | 406.1 | 2.18 | ¹H NMR (500 MHz, DMSO-d6) δ 2.25 (6H, s), 2.7-2.75 (2H, m), 4.1 (3H, s), 4.65-4.68 (2H, m), 6.4 (2H, brs), 6.6 (1H, d), 7.4 (1H, s), 8.75 (1H, d), 9.4 (1H, s), 9.6 (1H, s). |
| I-O-66 | 328.2 | 1.65 | ¹H NMR (500 MHz, DMSO-d6) δ 9.86 (s, 1H), 9.40 (s, 1H), 9.25 (s, 2H), 9.11 (d, J = 6.9 Hz, 1H), 8.54 (d, J = 6.2 Hz, 1H), 7.56 (d, J = 6.1 Hz, 1H), 7.19 (d, J = 6.9 Hz, 1H), 6.77 (s, 2H), 4.48 (s, 2H), 4.16 (s, 3H), 2.78 (s, 3H). |
| I-O-67 | 342.2 | 2.07 | ¹H NMR (500 MHz, DMSO-d6) δ 1.0 (3H, t), 1.63-1.7 (2H, m), 2.95 (2H, t), 4.22 (3H, s), 6.25 (1H, d), 7.78 (1H, d), 7.97-8.03 (1H, m), 8.3 (1H, d), 8.62 (1H, d), 9.7 (1H, s), 10.1 (1H, s) |
| I-O-68 | 370.3 | 1.66 | ¹H NMR (500 MHz, DMSO-d6) δ 3.2-3.3 (1H, m), 3.67-3.71 (2H, m), 4.15 (3H, s), 4.36-4.4 (2H, m), 4.67-4.7 (2H, m), 6.15 (1H, brs), 6.25 (1H, d), 7.62-7.65 (1H, m), 8.1 (1H, brs), 8.3 (1H, d), 8.52 (1H, s), 9.6 (1H, s), 9.95 (1H, s). |
| I-O-69 | 382.3 | 1.79 | ¹H NMR (500 MHz, Methanol-d4) δ 3.6-3.75 (8H, m), 5.3 (1H, d), 6.9 (1H, d), 7.1 (1H, s), 7.4 (1H, d), 7.7 (1H, d), 9.1 (1H, brs), 9.35 (1H, brs). |
| I-O-70 | 371.3 | 1.82 | ¹H NMR (500 MHz, Methanol-d4) δ 2.95 (6H, s), 3.5-3.55 (2H, m), 4.07-4.12 (2H, m), 4.32 (3H, s), 6.325 (1H, d), 7.72 (1H, d), 8.22 (1H, d), 8.5 (1H, d), 9.88 (1H, s). |
| I-O-71 | 397.3 | 1.90 | ¹H NMR (500 MHz, Methanol-d4) δ 1.15-1.2 (1H, m), 2.0-2.12 (4H, m), 2.3-2.4 (2H, m), 2.65-2.7 (1H, m), 3.28-3.31 (2H, m), 3.48-3.53 (1H, m), 3.6-3.67 (1H, m), 3.78-3.88 (3H, m), 6.13 (1H, d), 6.9-6.95 (1H, brs), 7.88-8.05 (2H, m), 9.4-9.45 (1H, brs). |
| I-O-72 | 397.3 | 1.92 | ¹H NMR (500 MHz, DMSO-d6) δ 1.8-1.9 (2H, m), 1.9-2.0 (2H, m), 3.0-3.1 (2H, m), 3.42-3.48 (2H, m), 3.55-3.61 (2H, m), 3.87-3.93 (2H, m), 4.15 (3H, s), 6.1-6.2 (1H, brs), 6.25 (1H, d), 7.65 (1H, d), 8.2 (1H, brs), 8.4 (1H, d), 8.52 (1H, d), 9.63 (1H, s), 9.85 (1H, s). |
| I-O-73 | 411.3 | 1.95 | ¹H NMR (500 MHz, DMSO-d6) δ 1.6-1.67 (1H, m), 1.8-1.9 (1H, m), 2.0-2.1 (1H, m), 2.1-2.2 (1H, m), 2.7 (3H, s), 2.9-3.0 (2H, m), 3.1-3.2 (1H, m), 3.5-3.8 (4H, m), 4.1 (3H, s), 6.25 (2H, brs), 6.65 (1H, brs), 7.6 (1H, s), 8.48-8.54 (2H, m), 9.65 (1H, brs), 9.75-9.9 (2H, m). |
| I-O-74 | 437.0 | 1.94 | ¹H NMR (500 MHz, DMSO-d6) δ 2.83-2.9 (1H, m), 3.1-3.18 (1H, m), 3.47-3.52 (1H, m), 3.62-3.67 (1H, m), 3.66-3.73 (1H, m), 4.15-4.21 (2H, m), 4.88-4.93 (1H, m), 7.45 (2H, brs), 6.87 (1H, d), 7.876 (1H, d), 8.56 (1H, d), 8.62 (1H, d), 9.63 (1H, s), 9.83 (1H, s). |
| I-O-75 | 409.3 | 2.05 | ¹H NMR (500 MHz, Methanol-d4) δ 1.2 (2H, t), 1.98-2.03 (1H, m), 2.15-2.3 (3H, m), 2.4-2.5 (1H, m), 3.6-3.65 (2H, m), 3.72-3.76 (2H, m), 4.4 (3H, s), 4.95-5.0 (1H, m), 6.7 (1H, brs), 7.7 (1H, d), 8.35 (1H, d), 8.5 (1H, d), 9.85 (1H, s) |
| I-O-76 | 369.2 | 1.65 | ¹H NMR (500 MHz, DMSO-d6) δ 3.3-3.35 (4H, m), 3.95-4.02 (4H, m), 4.12 (3H, s), 6.2-6.35 (2H, brs), 6.73 (1H, d), 7.62 (1H, d), 8.52 (1H, d), 8.61 (1H, d), 9.0-9.1 (2H, brs), 9.6 (1H, s), 9.75 (1H, s) |
| I-O-77 | 383.2 | 1.75 | ¹H NMR (500 MHz, DMSO-d6) δ 1.2 (3H, d), 2.83-3.0 (2H, m), 3.17-3.23 (2H, m), 3.97 (3H, s), 4.35-4.4 (1H, m), 4.55-4.6 (1H, m), 6.22 (2H, s), 6.7 (1H, d), 7.2 (1H, d), 8.2 (1H, d), 8.5 (1H, d), 9.42 (1H, d), 9.6 (1H, s). |
| I-O-78 | 383.3 | 1.85 | ¹H NMR (500 MHz, DMSO-d6) δ 2.88 (3H, s), 3.3-3.6 (8H, m), 4.1 (3H, s), 6.3 (2H, brs), 6.75 (1H, d), 7.6 (1H, brs), 8.5 (1H, brs), 8.63 (1H, d), 9.6 (1H, brs), 9.7 (1H, s). |
| I-O-79 | 411.2 | 2.09 | ¹H NMR (500 MHz, Methanol-d4) δ 1.52 (6H, d), 2.97 (3H, s), 3.2-3.5 (8H, m), 5.13-5.2 (1H, m), 6.75 1H, d), 7.75 (1H,d), 8.4 (1H,d), 8.48 (1H,d), 9.47. |
| I-O-80 | 411.3 | 1.93 | ¹H NMR (500 MHz, DMSO-d6) δ 1.6-1.7 (2H, m), 2.1-2.2 (2H, m), 2.78 (6H, s), 3.1-3.2 (2H, m), 3.5-3.6 (1H, m), 4.18 (3H, s), 4.7-4.8 (2H, m), 6.2-6.3 (2H, m), |

-continued

| Cmpds of formula I | LCMS ES+ | LCMS (Rt min) | HNMR |
|---|---|---|---|
| I-O-81 | 383.3 | 1.81 | 6.72 (1H, d), 7.68 (1H, d), 8.5-8.57 (2H, m), 9.6-9.7 (2H, m), 9.8 (1H, s). $^1$H NMR (500 MHz, DMSO-d6) δ 2.2-2.3 (2H, m), 2.4-2.5 (1H, m), 2.78 (3h, s), 3.65-4.0 (4H, m), 4.18 (3H, s), 6.28 (1H, brs), 6.42 (1H, d), 7.63-7.66 (1H, m), 8.52-8.57 (2H, m), 8.7 (2H, brs), 9.7 (1H, s), 9.95 (1H, s). |
| I-C-1 | 337.2 | 2.43 | $^1$H NMR (500 MHz, DMSO-d6) δ 9.45 (s, 1H), 9.40 (s, 1H), 9.30 (dd, J = 6.9, 0.6 Hz, 1H), 8.22 (d, J = 4.7 Hz, 1H), 7.52 (d, J = 6.9 Hz, 1H), 7.33 (d, J = 4.8 Hz, 1H), 7.01 (s, 2H), 2.42 (s, 3H). |
| I-C-2 | 399.0 | 2.75 | $^1$H NMR (500 MHz, DMSO-d6) δ 9.37 (s, 1H), 9.31 (s, 1H), 9.25-9.21 (m, 1H), 8.56 (d, J = 5.3 Hz, 1H), 7.62 (d, J = 5.3 Hz, 1H), 7.59-7.54 (m, 2H), 7.52-7.46 (m, 3H), 7.40 (d, J = 6.9 Hz, 1H), 7.00 (s, 2H). |
| I-C-3 | 356.2 | 1.85 | $^1$H NMR (500 MHz, DMSO-d6) δ 2.55 (3H, s,), 2.95 (6H, s), 3.6-3.63 (2H, m), 4.78-4.81 (2H, m), 6.5 (2H, brs), 6.62 (1H, d), 7.62-7.66 (1H, m), 8.43-8.5 (1H, m), 8.82 (1H, d), 9.2 (1H, brs), 9.38 (1H, brs), 9.8 (1H, brs). |
| I-N-1 | 421.0 | 2.18 | $^1$H NMR (500 MHz, DMSO-d6) δ 9.32-9.25 (m, 1H), 9.12 (s, 1H), 9.02 (s, 1H), 8.23 (d, J = 5.4 Hz, 1H), 7.52 (d, J = 6.9 Hz, 1H), 7.12 (dd, J = 5.4, 0.5 Hz, 1H), 7.03 (s, 2H), 2.98 (m, 4H), 2.44 (m, 4H), 2.17 (s, 3H). |
| I-N-2 | 435.2 | 1.97 | $^1$H NMR (500 MHz, DMSO-d6) δ 1.29 (2H, m), 1.81 (3H, m), 2.70 (2H, m), 3.03 (2H, m), 3.81 (2H, m), 7.05 (2H, br s), 7.47 (1H, m), 7.57 (1H, m), 7.89 (2H, br s), 8.42 (1H, m), 9.03 (1H, s), 9.14 (1H, s) and 9.33 (1H, m) ppm. |
| I-N-3 | 451.0 | 1.95 | $^1$H NMR (500 MHz, DMSO-d6) δ 9.24 (d, J = 6.9 Hz, 1H), 9.13 (s, 1H), 9.04 (s, 1H), 8.35 (d, J = 5.9 Hz, 1H), 7.48 (d, J = 6.9 Hz, 1H), 7.32 (d, J = 5.9 Hz, 1H), 3.83-3.69 (m, 2H), 3.55 (d, J = 5.0 Hz, 4H), 3.28 (d, J = 6.4 Hz, 4H), 3.18-3.00 (m, 2H). |

Example 10

Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media from a final concentration of 25 μM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0cx for Macintosh, GraphPad Software, San Diego, Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry,* 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 11

ATR Inhibition Assay

Compounds were screened for their ability to inhibit ATR kinase using a radioactive-phosphate incorporation assay. Assays were carried out in a mixture of 50 mM Tris/HCl (pH 7.5), 10 mM $MgCl_2$ and 1 mM DTT. Final substrate concentrations were 10 μM [γ-33P]ATP (3 mCi 33P ATP/mmol ATP, Perkin Elmer) and 800 μM target peptide (ASELPASQPQPFSAKKK (SEQ. ID NO: 1)).

Assays were carried out at 25° C. in the presence of 5 nM full-length ATR. An assay stock buffer solution was prepared containing all of the reagents listed above, with the exception of ATP and the test compound of interest. 13.5 μL of the stock solution was placed in a 96 well plate followed by addition of 2 μL of DMSO stock containing serial dilutions of the test compound (typically starting from a final concentration of 15 μM with 3-fold serial dilutions) in duplicate (final DMSO concentration 7%). The plate was pre-incubated for 10 minutes at 25° C. and the reaction initiated by addition of 15 μL [γ-33P]ATP (final concentration 10 μM).

The reaction was stopped after 24 hours by the addition of 30 μL, 0.1M phosphoric acid containing 2 mM ATP. A multiscreen phosphocellulose filter 96-well plate (Millipore, Cat no. MAPHN0B50) was pretreated with 100 μL 0.2M phosphoric acid prior to the addition of 45 μL of the stopped assay mixture. The plate was washed with 5×200 μL 0.2M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Table 2, below, shows the ATR Inhibition Ki values of compounds of the disclosure. Compounds with a Ki value of <0.01 μM are marked with "+++." Compounds with a Ki value >0.01 μM but <1 μM are marked with "++." Compounds with a Ki value >1 μM but <5 μM are marked with "+."

TABLE 2

| Cmpd. # | ATR Ki |
|---|---|
| I-O-1 | +++ |
| I-O-2 | +++ |
| I-O-3 | +++ |
| I-O-4 | ++ |
| I-O-5 | ++ |
| I-O-6 | +++ |
| I-O-7 | ++ |
| I-O-8 | ++ |
| I-O-9 | ++ |
| I-O-10 | ++ |
| I-O-11 | ++ |
| I-O-12 | ++ |
| I-O-13 | +++ |
| I-O-14 | +++ |
| I-O-15 | +++ |
| I-O-16 | ++ |
| I-O-17 | ++ |
| I-O-18 | ++ |
| I-O-19 | ++ |

TABLE 2-continued

| Cmpd. # | ATR Ki |
|---|---|
| I-O-20 | ++ |
| I-O-21 | ++ |
| I-O-22 | ++ |
| I-O-23 | ++ |
| I-O-24 | ++ |
| I-O-25 | ++ |
| I-O-26 | ++ |
| I-O-27 | ++ |
| I-O-28 | ++ |
| I-O-29 | ++ |
| I-O-30 | ++ |
| I-O-31 | ++ |
| I-O-32 | ++ |
| I-O-33 | ++ |
| I-O-34 | ++ |
| I-O-35 | ++ |
| I-O-36 | ++ |
| I-O-37 | ++ |
| I-O-38 | ++ |
| I-O-39 | ++ |
| I-O-40 | ++ |
| I-O-41 | ++ |
| I-O-42 | ++ |
| I-O-43 | ++ |
| I-O-44 | + |
| I-O-45 | ++ |
| I-O-46 | ++ |
| I-O-47 | ++ |
| I-O-48 | ++ |
| I-O-49 | + |
| I-O-50 | ++ |
| I-O-51 | ++ |
| I-O-52 | ++ |
| I-O-53 | ++ |
| I-O-54 | ++ |
| I-O-55 | ++ |
| I-O-56 | ++ |
| I-O-57 | ++ |
| I-O-58 | ++ |
| I-O-59 | ++ |
| I-O-60 | ++ |
| I-O-61 | ++ |
| I-O-62 | ++ |
| I-O-63 | ++ |
| I-O-64 | + |
| I-O-65 | ++ |
| I-O-66 | ++ |
| I-O-67 | ++ |
| I-O-68 | +++ |
| I-O-69 | ++ |
| I-O-70 | ++ |
| I-O-71 | ++ |
| I-O-72 | ++ |
| I-O-73 | ++ |
| I-O-74 | +++ |
| I-O-75 | ++ |
| I-O-76 | ++ |
| I-O-77 | ++ |
| I-O-78 | ++ |
| I-O-79 | + |
| I-O-80 | ++ |
| I-O-81 | ++ |
| I-C-1 | ++ |
| I-C-2 | ++ |
| I-C-3 | + |
| I-N-1 | ++ |
| I-N-2 | ++ |
| I-N-3 | ++ |

Example 12

Cisplatin Sensitization Assay

Compounds can be screened for their ability to sensitize HCT116 colorectal cancer cells to Cisplatin using a 96 h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) are plated at 470 cells per well in 96-well polystyrene plates (Costar 3596) in 150 μl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 μM as a full matrix of concentrations in a final cell volume of 200 μl, and the cells are then incubated at 37° C. in 5% $CO_2$. After 96 h, 40 μl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and the concentration of compound required to reduce the IC50 of Cisplatin alone by at least 3-fold (to 1 decimal place) can be reported.

Table 3, below, shows the Cisplatin sensitization values of compounds of the disclosure. Compounds with a Cisplatin sensitization value of <0.02 μM are marked with "+++." Compounds with a Cisplatin sensitization value >0.02 μM but <0.2 μM are marked with "++." Compounds with a Cisplatin sensitization value >0.2 μM but <5 μM are marked with "+."

TABLE 3

| Cmpd. # | Synergy with Cisplatin |
|---|---|
| I-O-1 | +++ |
| I-O-2 | +++ |
| I-O-3 | +++ |
| I-O-4 | +++ |
| I-O-5 | +++ |
| I-O-6 | +++ |
| I-O-7 | — |
| I-O-8 | +++ |
| I-O-9 | +++ |
| I-O-10 | +++ |
| I-O-11 | +++ |
| I-O-12 | +++ |
| I-O-13 | +++ |
| I-O-14 | +++ |
| I-O-15 | +++ |
| I-O-16 | + |
| I-O-17 | ++ |
| I-O-18 | ++ |
| I-O-19 | ++ |
| I-O-20 | ++ |
| I-O-21 | ++ |
| I-O-22 | ++ |
| I-O-23 | ++ |
| I-O-24 | +++ |
| I-O-25 | ++ |
| I-O-26 | +++ |
| I-O-27 | ++ |
| I-O-28 | ++ |
| I-O-29 | — |
| I-O-30 | +++ |
| I-O-31 | ++ |
| I-O-32 | ++ |
| I-O-33 | ++ |
| I-O-34 | ++ |
| I-O-35 | +++ |
| I-O-36 | ++ |
| I-O-37 | ++ |
| I-O-38 | + |
| I-O-39 | — |
| I-O-40 | ++ |
| I-O-41 | ++ |
| I-O-42 | +++ |
| I-O-43 | ++ |
| I-O-44 | + |
| I-O-45 | +++ |
| I-O-46 | ++ |
| I-O-47 | ++ |
| I-O-48 | ++ |
| I-O-49 | + |
| I-O-50 | ++ |
| I-O-51 | + |
| I-O-52 | +++ |
| I-O-53 | — |
| I-O-54 | ++ |
| I-O-55 | +++ |
| I-O-56 | +++ |
| I-O-57 | ++ |
| I-O-58 | ++ |
| I-O-59 | ++ |
| I-O-60 | ++ |
| I-O-61 | ++ |
| I-O-62 | ++ |
| I-O-63 | ++ |
| I-O-64 | + |
| I-O-65 | + |
| I-O-66 | ++ |
| I-O-67 | ++ |
| I-O-68 | ++ |
| I-O-69 | — |
| I-O-70 | + |
| I-O-71 | + |
| I-O-72 | + |
| I-O-73 | + |
| I-O-74 | +++ |
| I-O-75 | ++ |
| I-O-76 | ++ |
| I-O-77 | ++ |
| I-O-78 | + |
| I-O-79 | + |
| I-O-80 | + |
| I-O-81 | — |
| I-C-1 | ++ |
| I-C-2 | + |
| I-C-3 | ++ |
| I-N-1 | + |
| I-N-2 | — |
| I-N-3 | — |

Example 13

Single Agent HCT116 Activity

Compounds can be screened for single agent activity against HCT116 colorectal cancer cells using a 96 h cell viability (MTS) assay. HCT116 are plated at 470 cells per well in 96-well polystyrene plates (Costar 3596) in 150 μl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media in 2-fold serial dilutions from a top final concentration of 10 μM as a full matrix of concentrations in a final cell volume of 200 μl, and the cells are then incubated at 37° C. in 5% $CO_2$. After 96 h, 40 μl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and IC50 values can be calculated.

Example 14

ATR-Complex Inhibition Assay

Compounds were screened for their ability to inhibit ATR kinase, in the presence of partner proteins ATRIP, CLK2 and TopBP1, using a radioactive-phosphate incorporation assay. Assays were carried out in a mixture of 50 mM Tris/HCl (pH 7.5), 10 mM $MgCl_2$ and 1 mM DTT. Final substrate concentrations were 10 μM [g-33P]ATP (3.5 μCi 33P ATP/nmol ATP, Perkin Elmer, Massachusetts, USA) and 800 μM target peptide (ASELPASQPQPFSAKKK (SEQ. ID NO: 1)), Isca Biochemicals, Cambridgeshire, UK).

Assays were carried out at 25° C. in the presence of 4 nM full-length ATR, 40 nM full-length ATRIP, 40 nM full-length CLK2 and 600 nM TopBP1(A891-S1105). An enzyme stock buffer solution was prepared containing all of the reagents listed above, with the exception of target peptide, ATP and the test compound of interest. This enzyme stock was pre-incubated for 30 minutes at 25° C. 8.5 μL of the enzyme stock solution was placed in a 96-well plate followed by addition of 5 μl of target peptide and 2 μL of DMSO stock containing serial dilutions of the test compound (typically starting from a final concentration of 1.5 μM with 2.5-fold serial dilutions) in duplicate (final DMSO concentration 7%). The plate was pre-incubated for 10 minutes at 25° C. and the reaction initiated by addition of 15 μL [g-33P]ATP (final concentration 10 μM).

The reaction was stopped after 20 hours by the addition of 30 μL 0.3 M phosphoric acid containing 2 mM ATP. A phosphocellulose filter 96-well plate (Multiscreen HTS MAPH-NOB50, Merck-Millipore, Mass., USA) was pretreated with 100 μL 0.1 M phosphoric acid prior to the addition of 45 μL of the stopped assay mixture. The plate was washed with 5×200 μL 0.1 M phosphoric acid. After drying, 50 μL Optiphase 'SuperMix' liquid scintillation cocktail (Perkin Elmer, Mass., USA) was added to the well prior to scintillation counting (Wallac 1450 Microbeta Liquid Scintillation Counter, Perkin Elmer, Mass., USA).

After removing mean background values for all of the data points, Ki(app) data were calculated from non-linear regression analysis of the initial rate data using the Prism software package (GraphPad Prism version 6.0c for Macintosh, GraphPad Software Inc., San Diego, USA).

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A compound of formula I:

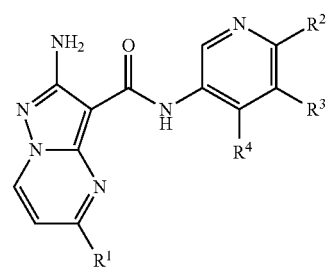

or a pharmaceutically acceptable salt thereof, wherein:
$R^1$ is independently selected from $-(L^1)_n-W$ or M;
M and $L^1$ are a $C_{1-8}$aliphatic wherein up to three methylene units are optionally replaced with —O—, —NR—, —C(O)—, or —S(O)$_z$—, each M and $L^1$ is optionally substituted with 0-3 occurrences of $J^{LM}$;
$J^{LM}$ is independently selected from halo, —CN, or a $C_{1-4}$aliphatic chain wherein up to two methylene units of the aliphatic chain are optionally replaced with —O—, —NR—, —C(O)—, or —S(O)$_z$—;
n is independently selected from 0 or 1;
W is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein W is optionally substituted with 0-5 occurrences of $J^W$;
$J^W$ is independently selected from —CN, halo, —CF$_3$; a $C_{1-4}$aliphatic wherein up to two methylene units are optionally replaced with —O—, —NR—, —C(O)—, or —S(O)$_z$—; or a 3-6 membered non-aromatic ring having 0-2 heteroatoms selected from oxygen, nitrogen, or sulfur;
two occurrences of $J^W$ on the same atom, together with atom to which they are joined, form a 3-6 membered ring having 0-2 heteroatoms selected from oxygen, nitrogen, or sulfur; or
two occurrences of $J^W$, together with W, form a 6-10 membered saturated or partially unsaturated bridged ring system;

---

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ser Glu Leu Pro Ala Ser Gln Pro Gln Pro Phe Ser Ala Lys Lys
1               5                   10                  15

Lys $R^2$ is independently selected from H; halo; —CN; a $C_{1-2}$alkyl optionally substituted with 1-3 occurrences of fluoro; or a $C_{1-3}$aliphatic chain wherein up to two methylene units of the aliphatic chain are optionally replaced with —O—, —NR—, —C(O)—, or —S(O)$_z$;

$R^3$ is independently selected from H; halo; $C_{1-4}$alkyl optionally substituted with 1-3 occurrences of halo; $C_{3-4}$cycloalkyl; 3-4 membered heterocyclyl; —CN; or a $C_{1-3}$aliphatic chain wherein up to two methylene units of the aliphatic chain are optionally replaced with —O—, —NR—, —C(O)—, or —S(O)$_z$;

$R^4$ is independently selected from -(L$^2$)$_k$-Q$^1$ or T;

$L^2$ and T are each independently a $C_{1-10}$aliphatic chain wherein up to three methylene units of the aliphatic chain are optionally replaced with —O—, —NR—, —C(O)—, or —S(O)$_z$—; each $L^2$ and T is optionally substituted with 0-5 occurrences of $J^{LT}$;

$J^{LT}$ is independently selected from —CN; halo or a $C_{1-4}$aliphatic chain wherein up to two methylene units of the aliphatic chain are optionally replaced with —O—, —NR—, —C(O)—, or —S(O)$_z$—;

k is 0 or 1;

$Q^1$ is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein $Q^1$ is independently substituted with 0-5 occurrences of $J^Q$;

$J^Q$ is independently selected from —CN; halo; =O; $Q^2$; or a $C_{1-8}$aliphatic chain wherein up to three methylene units of the aliphatic chain are optionally replaced with —O—, —NR—, —C(O)—, or —S(O)$_z$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with $Q^1$, form a 6-10 membered saturated or partially unsaturated bridged ring system;

$Q^2$ is independently a 3-7 membered fully saturated, partially unsaturated, or aromatic monocyclic ring having 0-3 heteroatoms selected from oxygen, nitrogen, or sulfur; or a 7-12 membered fully saturated, partially unsaturated, or aromatic bicyclic ring having 0-5 heteroatoms selected from oxygen, nitrogen, or sulfur $J^R$ is independently selected from —CN, halo; =O; →O; $Q^3$; or a $C_{1-6}$aliphatic chain wherein up to two methylene units of the aliphatic chain are optionally replaced with —O—, —NR—, —S—, —C(O)—, or —S(O)$_z$—; each $J^R$ is optionally substituted with 0-3 occurrences of $J^P$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from oxygen, nitrogen, or sulfur; or a 7-12 membered fully saturated, partially unsaturated, or aromatic bicyclic ring having 0-5 heteroatoms selected from oxygen, nitrogen, or sulfur;

$J^X$ is independently selected from —CN, halo or a $C_{1-4}$aliphatic chain wherein up to two methylene units of the aliphatic chain are optionally replaced with —O—, —NR—, —C(O)—, or —S(O)$_z$—; or $J^P$ is independently selected from —CN; =O; halo; a $C_{1-6}$aliphatic chain wherein up to two methylene units of the aliphatic chain are optionally replaced with —O—, —NR—, —C(O)—, or —S(O)$_z$—; or a 3-6 membered non-aromatic ring having 0-2 heteroatoms selected from oxygen, nitrogen, or sulfur; each $J^P$ is optionally substituted with 0-3 occurrences of $J^M$; or two occurrences of $J^P$ on the same atom, together with the atom to which they are joined, form a 3-6 membered ring having 0-2 heteroatoms selected from oxygen, nitrogen, or sulfur; or two occurrences of $J^P$, together with $Q^3$, form a 6-10 membered saturated or partially unsaturated bridged ring system;

$J^M$ is independently selected from halo or $C_{1-6}$aliphatic;

z is 0, 1 or 2; and

R is independently selected from H or $C_{1-4}$aliphatic.

2. The compound of claim 1, wherein $R^1$ is M.

3. The compound of claim 2, wherein M is a $C_{1-8}$aliphatic wherein up to three methylene units are optionally replaced with —O— or —NR—.

4. The compound of claim 3, wherein M is $C_{1-4}$alkyl, —(C$_{1-4}$alkyl)O(C$_{1-3}$aliphatic), —(C$_{1-3}$alkyl)OH, —O(C$_{1-4}$alkyl)N(C$_{1-2}$alkyl)$_2$, —NH(C$_{1-4}$alkyl), or —(C$_{1-4}$alkyl)NH(C$_{1-4}$alkyl).

5. The compound of claim 4, wherein M is $C_{1-4}$alkyl.

6. The compound of claim 2, wherein $J^{LM}$ is halo.

7. The compound of claim 1, wherein $R^1$ is -(L$^1$)$_n$-W.

8. The compound of claim 7, wherein n is 1.

9. The compound of claim 8, wherein $L^1$ is a $C_{1-8}$aliphatic wherein up to three methylene units are optionally replaced with —O— or —NR—.

10. The compound of claim 9, wherein $L^1$ is —O—, —O(C1-4aliphatic)-, or —NR(C$_{1-3}$alkyl)-.

11. The compound of claim 1, wherein n is 0.

12. The compound of claim 7, wherein W is a 3-7 membered fully saturated, partially unsaturated, or aromatic monocyclic ring having 0-3 heteroatoms selected from oxygen, nitrogen or sulfur.

13. The compound of claim 12, wherein W is a 3-7 membered heterocyclyl.

14. The compound of claim 13, wherein W is independently selected from pyrrolidinyl, piperidinyl, piperazinyl, oxetanyl, or azetidinyl.

15. The compound of claim 7, wherein W is a 7-12 membered fully saturated, partially unsaturated, or aromatic bicyclic ring having 0-5 heteroatoms selected from oxygen, nitrogen, or sulfur.

16. The compound of claim 15, wherein W is octahydropyrrolo[1,2-a]pyrazine.

17. The compound of claim 7, wherein $J^W$ is selected form $C_{1-3}$alkyl or CF$_3$.

18. The compound of claim 12, wherein two occurrences of $J^W$ on the same atom, together with atom to which they are joined, form a 3-6 membered ring having 0-2 heteroatoms selected from oxygen, nitrogen, or sulfur.

19. The compound of claim 18, wherein the ring formed by the two occurrences of $J^W$ is an oxetanyl.

20. The compound of claim 1, wherein $R^2$ is H or chloro.

21. The compound of claim 20, wherein $R^2$ is H.

22. The compound of claim 1, wherein $R^3$ is H or chloro.

23. The compound of claim 22, wherein $R^3$ is H.

24. The compound of claim 1, wherein $R^4$ is $-(L^2)_m-Q^1$.

25. The compound of claim 24, wherein m is 1.

26. The compound of claim 25, wherein $L^2$ is —O—.

27. The compound of claim 24, wherein m is 0.

28. The compound of claim 24, wherein $Q^1$ is independently selected from a 3-7 membered fully saturated, partially unsaturated, or aromatic monocyclic ring having 0-3 heteroatoms selected from oxygen, nitrogen or sulfur.

29. The compound of claim 28, wherein $Q^1$ is a 3-7 membered heterocyclyl or carbocycle.

30. The compound of claim 29, wherein $Q^1$ is independently selected from cyclopropyl, cyclobutyl, cyclopentyl, cyclohexyl, cycloheptyl, pyrrolidinyl, piperidinyl, azepanyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, dihydroimidazolyl, 1,3-tetrahydropyrimidinyl, dihydropyrimidinyl, 1,4-diazepanyl, 1,4-oxazepanyl, 1,4-thiazepanyl, and azetidinyl.

31. The compound of claim 30, wherein $Q^1$ is independently selected from pyrrolidinyl, cyclopropyl, cyclohexyl, piperidinyl or piperazinyl.

32. The compound of claim 28, wherein $Q^1$ is a 5-6 membered aryl or heteroaryl.

33. The compound of claim 32, wherein $Q^1$ is independently selected from phenyl, pyridinyl, pyrazinyl, pyrimidinyl, tetrahydropyridinyl, pyrrolyl, imidazolyl, pyrazolyl, 1,2,3-triazolyl, or 1,2,4-triazolyl.

34. The compound of claim 33, wherein $Q^1$ is pyridinyl.

35. The compound of claim 24, wherein $Q^1$ is a 7-12 membered fully saturated, partially unsaturated, or aromatic bicyclic ring having 1-5 heteroatoms selected from oxygen, nitrogen, or sulfur.

36. The compound of claim 35, wherein $Q^1$ is independently selected from octahydropyrrolo[1,2-a]pyrazinyl, 5,6,7,8-tetrahydroimidazo[1,2-a]pyridinyl, octahydro-1H-pyrazino[1,2-a]pyrazinyl, 5,6,7,8-tetrahydroimidazo[1,5-a]pyrazinyl, 2,5-diazabicyclo[4.1.0]heptane, or octahydropyrazino[2,1-c][1,4]oxazinyl.

37. The compound of claim 24, wherein $J^Q$ is $C_{1-6}$ aliphatic chain wherein up to two methylene units of the aliphatic chain are optionally replaced with —O—, —NR—, or —C(O)—.

38. The compound of claim 37, wherein $J^Q$ is independently selected from —C(O)—, $C_{1-4}$ alkyl, —$(C_{0-4}$alkyl)$NH_2$, —$(C_{0-4}$alkyl)NH($C_{1-4}$ alkyl), —$(C_{0-4}$alkyl)N$(C_{1-4}$alkyl)$_2$, —$(C_{0-4}$alkyl)OH, —$(C_{0-4}$alkyl)O($C_{1-4}$alkyl), —C(O)OH, —C(O)O($C_{1-4}$alkyl), N($C_{1-4}$alkyl)$_2$, —C(O)N($C_{1-4}$alkyl)$_2$, or —$(C_{1-3}$alkyl)O($C_{1-2}$alkyl)N($C_{1-3}$alkyl)$_2$.

39. The compound of claim 38, wherein $J^Q$ is independently selected from —C(O)—, $C_{1-4}$alkyl, or —$(C_{0-4}$alkyl)$NH_2$.

40. The compound of claim 24, wherein $J^Q$ is $Q^2$.

41. The compound of claim 40, wherein $Q^2$ is a 3-7 membered fully saturated, partially unsaturated, or aromatic monocyclic ring having 0-3 heteroatoms selected from oxygen, sulfur, or nitrogen.

42. The compound of claim 41, wherein $Q^2$ is independently selected from selected from cyclopropyl, cyclobutyl, cyclopentyl, cyclohexyl, oxetanyl, tetrahydropyranyl, tetrahydrofuranyl, azetidinyl, pyrrolidinyl, piperidinyl, piperazinyl, thiomorpholinyl, or morpholinyl.

43. The compound of claim 42, wherein $Q^2$ is oxetanyl, pyrrolidinyl, or tetrahydropyranyl.

44. The compound of claim 40, wherein $Q^2$ is a 7-12 membered fully saturated, partially unsaturated, or aromatic bicyclic ring having 0-5 heteroatoms selected from oxygen, nitrogen, or sulfur.

45. The compound of claim 44, wherein $Q^2$ is independently selected from 5,6,7,8-tetrahydroimidazo[1,5-a]pyrazinyl or 5,6,7,8-tetrahydroimidazo[1,2-a]pyrazinyl.

46. The compound of claim 24, wherein two occurrences of $J^Q$, together with $Q^1$, form a bridged ring system.

47. The compound of claim 24, wherein $J^Q$ is =O, halo, or →O.

48. The compound of claim 28, wherein two occurrences of $J^Q$ on the same atom, taken together with the atom to which they are joined, form a 3-6 membered non-aromatic ring having 0-2 heteroatoms selected from oxygen, nitrogen, or sulfur.

49. The compound of claim 48, wherein the ring formed by the two occurrences of $J^Q$ on the same atom, taken together with the atom to which they are joined, is selected from oxetanyl, cyclobutyl, or azetidinyl.

50. The compound of claim 24, wherein $J^R$ is a 3-6 membered heterocyclyl having 1-3 heteroatoms selected from oxygen, nitrogen, or sulfur.

51. The compound of claim 50, wherein $J^R$ is independently selected from oxetanyl, piperadinyl, azetidinyl, piperazinyl, pyrrolidinyl, or morpholinyl.

52. The compound of claim 51, wherein $J^R$ is a piperazinyl.

53. The compound of claim 24, wherein $J^R$ is independently selected from halo, =O, —OH, $C_{1-4}$alkyl, —$(C_{0-4}$alkyl)N($C_{1-4}$alkyl)$_2$, or —$(C_{0-4}$alkyl)O($C_{1-4}$alkyl).

54. The compound of claim 40, wherein two occurrences of $J^R$ on the same atom, together with the atom to which they are joined, form a 3-6 membered aromatic or non-aromatic ring having 0-2 heteroatoms selected from oxygen, nitrogen, or sulfur.

55. The compound of claim 50, wherein $J^P$ is —$C_{1-4}$alkyl.

56. The compound of claim 1, wherein $R^4$ is T.

57. The compound of claim 56, wherein T is independently selected from —$(C_{1-4}$alkyl), —$(C_{1-4}$alkyl)N($C_{1-4}$alkyl)$_2$, —$(C_{1-3}$alkyl)O($C_{1-2}$alkyl)N($C_{1-3}$alkyl)$_2$, —$(C_{1-4}$alkyl)OH, —$(C_{1-4}$alkyl)$NH_2$, or —$(C_{1-4}$alkyl)O($C_{1-4}$alkyl).

58. The compound of claim 56, wherein $J^{LT}$ is halo or $C_{1-3}$alkyl.

59. The compound of claim 1 independently selected from:

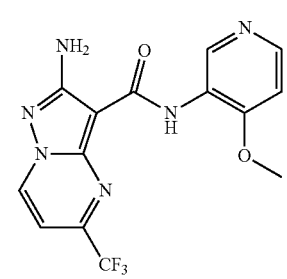

I-O-1

-continued
I-O-2
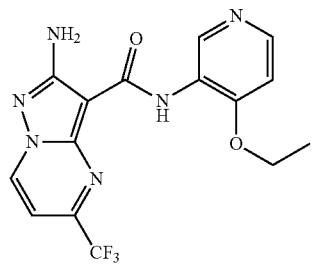
I-O-3
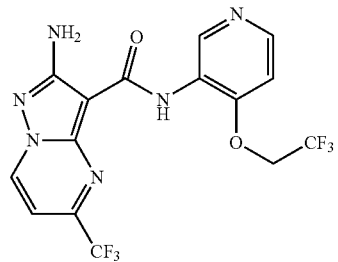
I-O-4
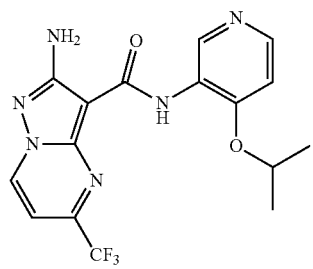
I-O-5
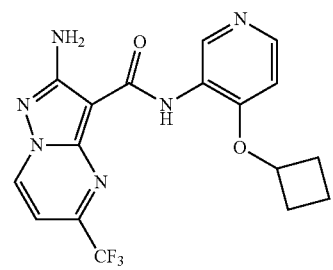
I-O-6
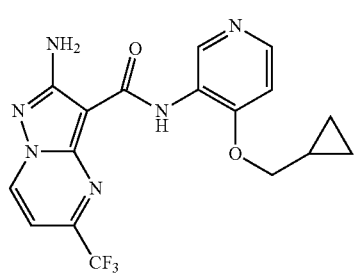
I-O-7
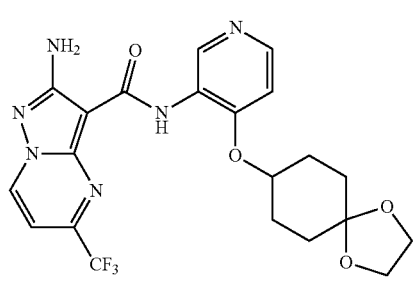
-continued
I-O-8
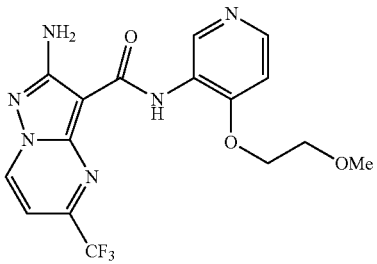
I-O-9
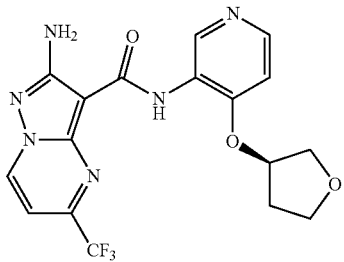
I-O-10
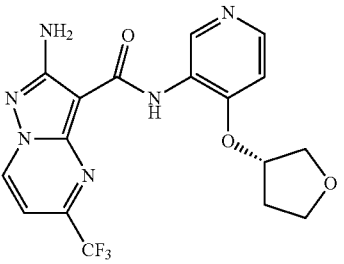
I-O-11
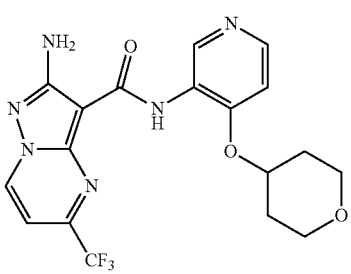
I-O-12
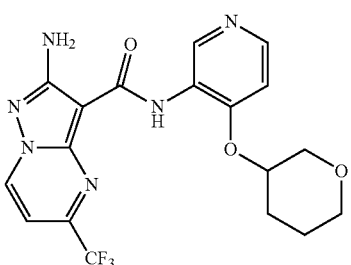
I-O-13
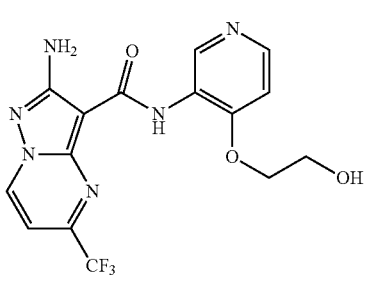

I-O-14
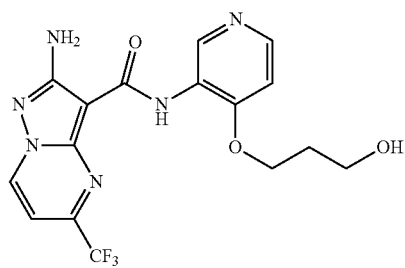
I-O-15
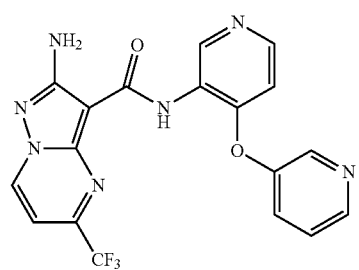
I-O-16
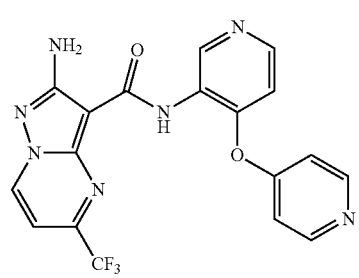
I-O-17
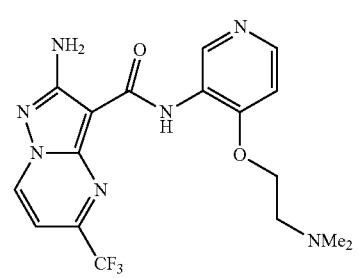
I-O-18
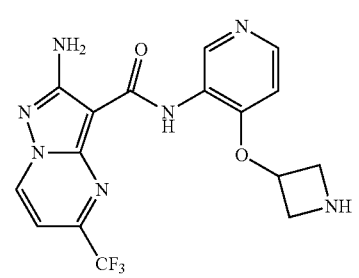
I-O-19
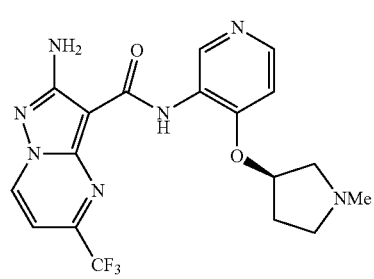
I-O-20
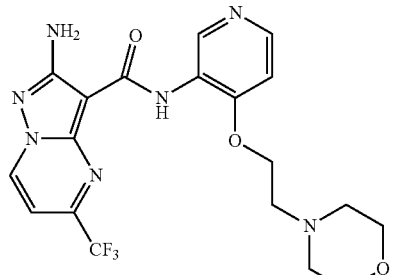
I-O-21
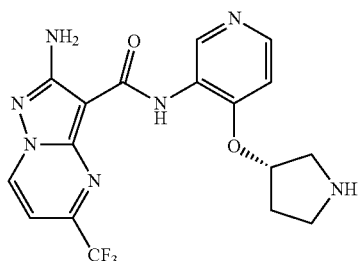
I-O-22
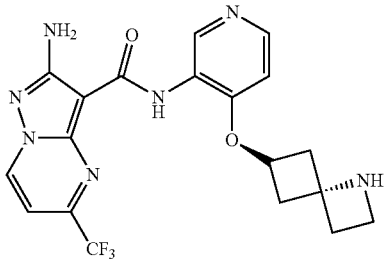
I-O-23
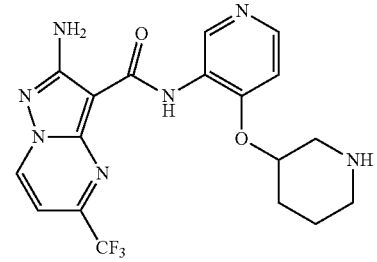
I-O-24
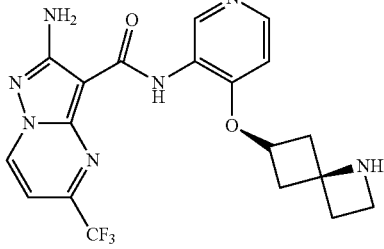
I-O-25
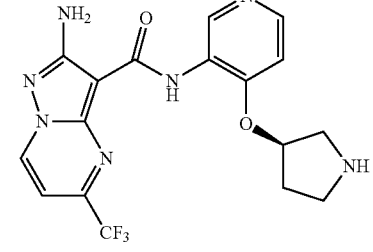

I-O-26 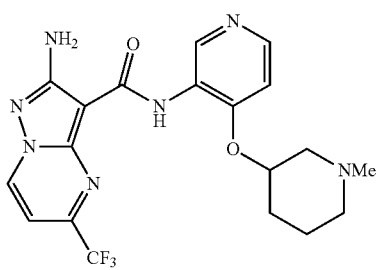
I-O-27 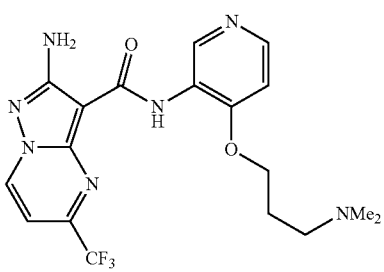
I-O-28 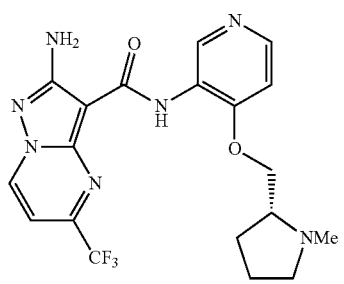
I-O-29 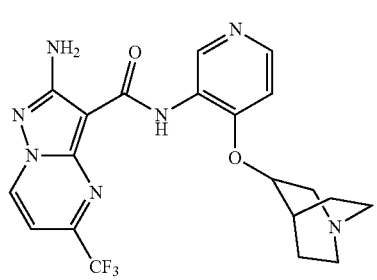
I-O-30 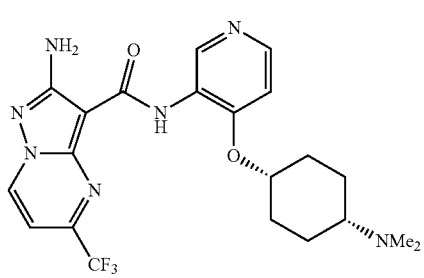
I-O-31 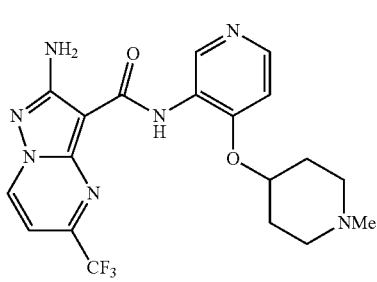
I-O-32 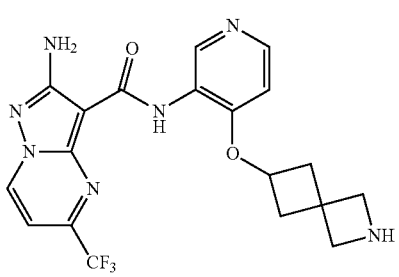
I-O-33 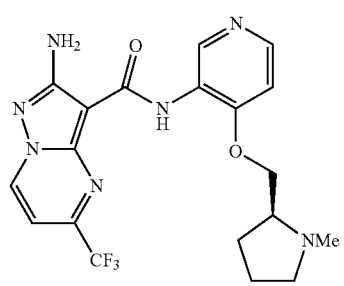
I-O-34 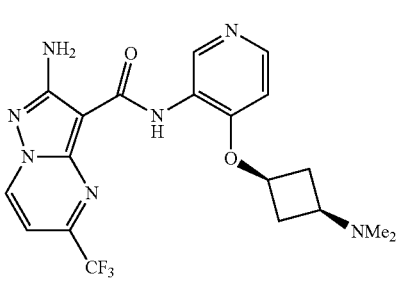
I-O-35 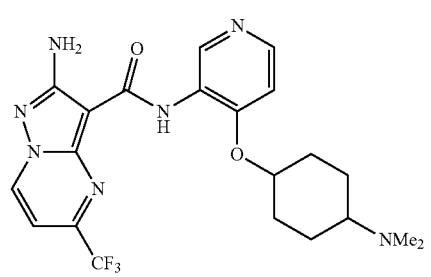
I-O-36 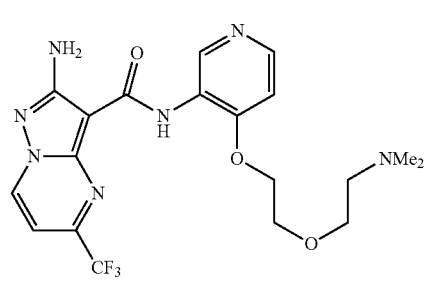

I-O-37
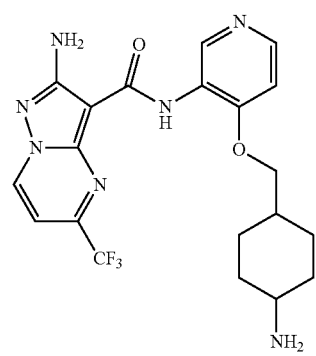
I-O-38
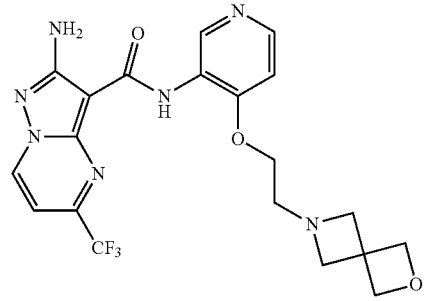
I-O-39
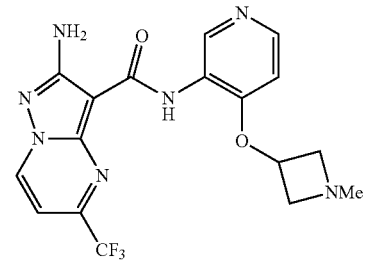
I-O-40
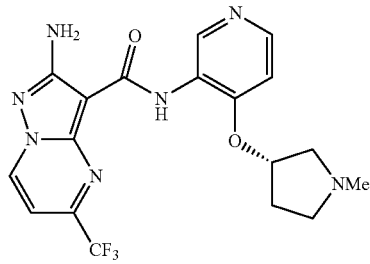
I-O-41
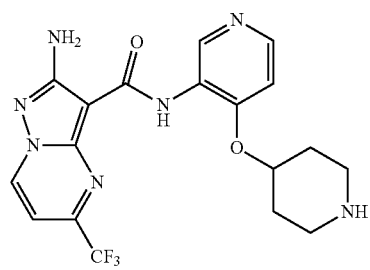
I-O-42
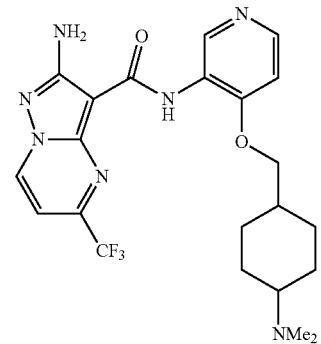
I-O-43
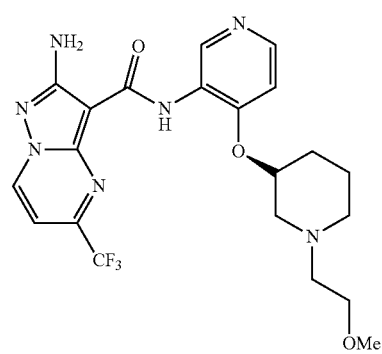
I-O-44
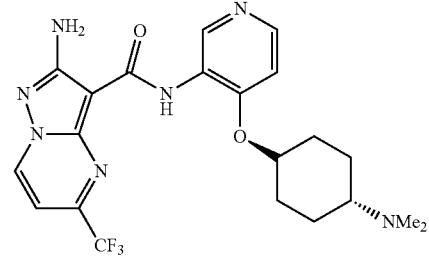
I-O-45
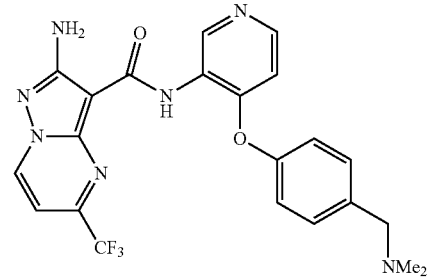
I-O-46
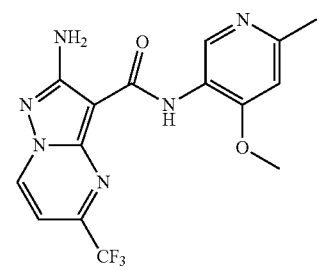

| | |
|---|---|
| 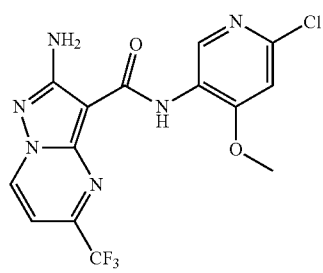 I-O-47 | 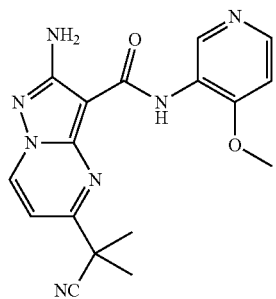 I-O-52 |
| 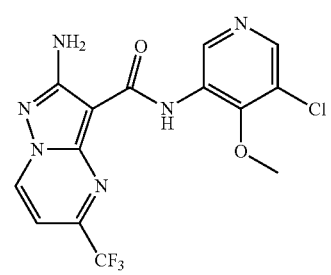 I-O-48 | 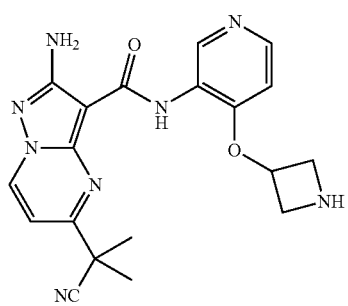 I-O-53 |
| 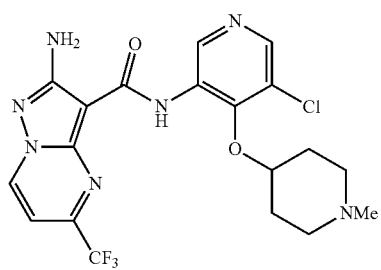 I-O-49 | 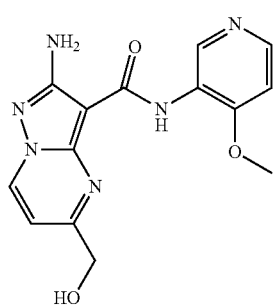 I-O-54 |
| 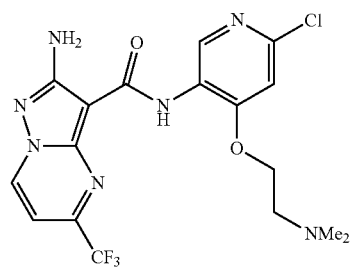 I-O-50 | 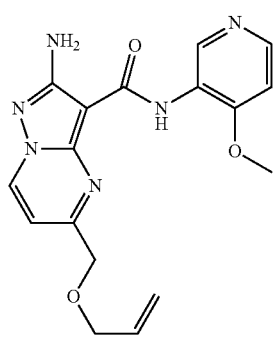 I-O-55 |
| 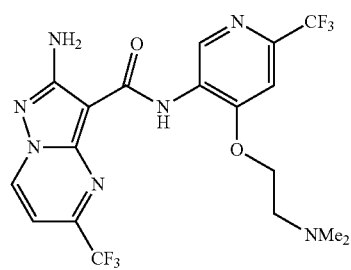 I-O-51 | 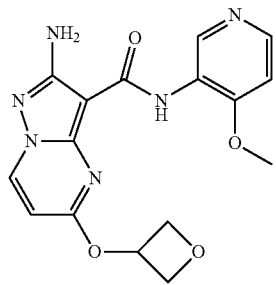 I-O-56 |

I-O-57
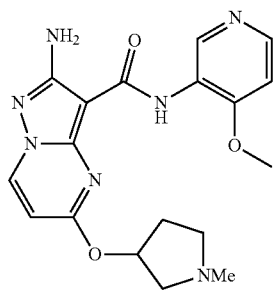
I-O-58
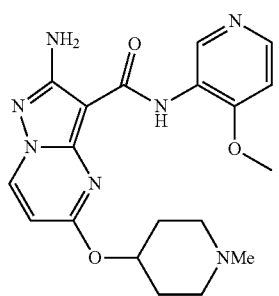
I-O-59
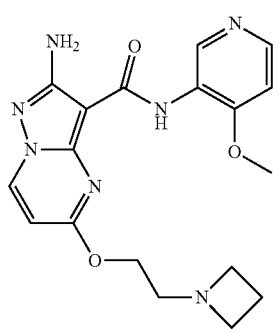
I-O-60
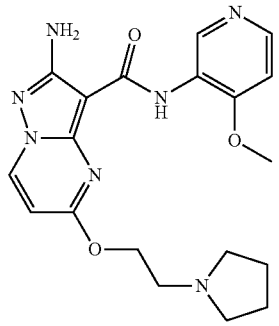
I-O-61
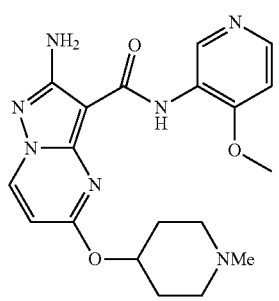
I-O-62
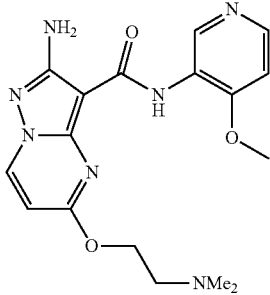
I-O-63
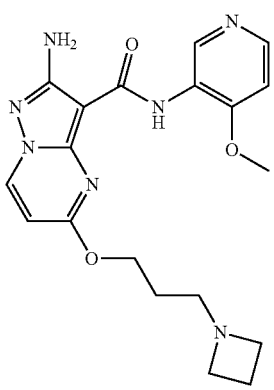
I-O-64
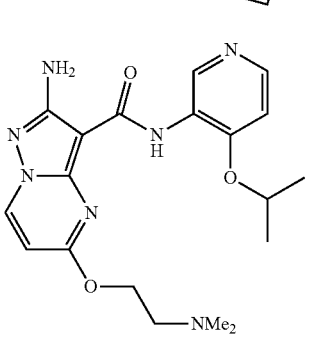
I-O-65
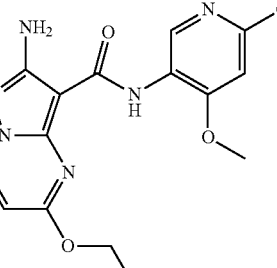
I-O-66
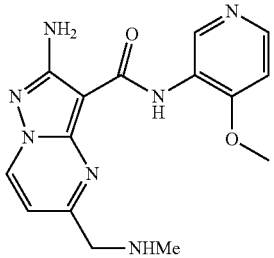

I-O-67
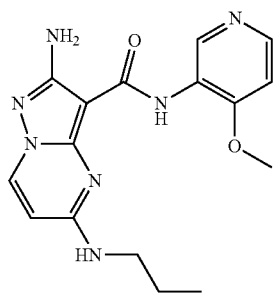
I-O-68
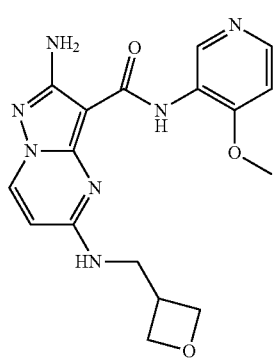
I-O-69
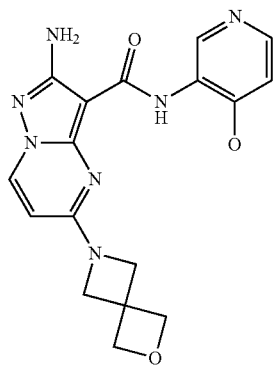
I-O-70
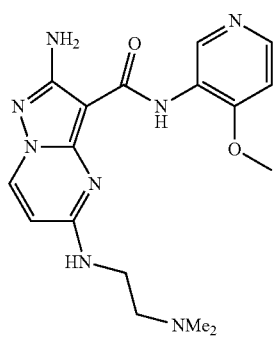
I-O-71
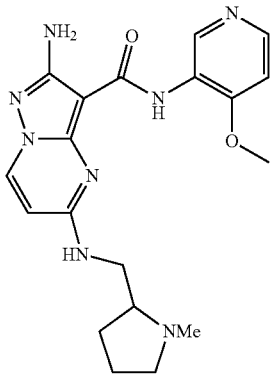
I-O-72
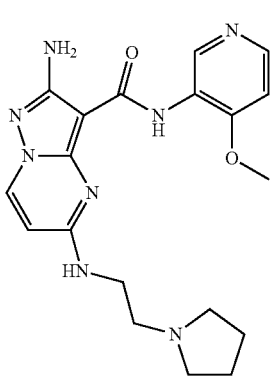
I-O-73
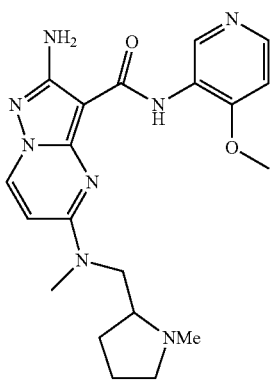
I-O-74
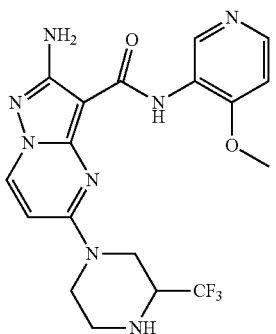

I-O-75
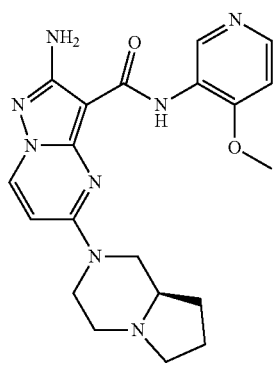
I-O-76
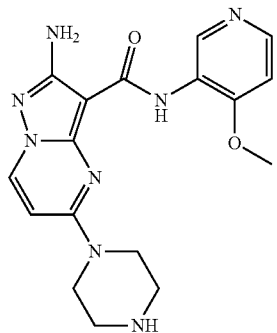
I-O-77
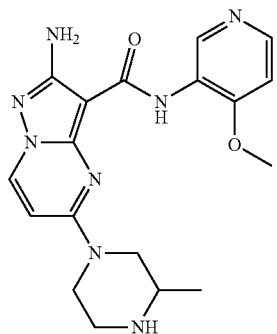
I-O-78
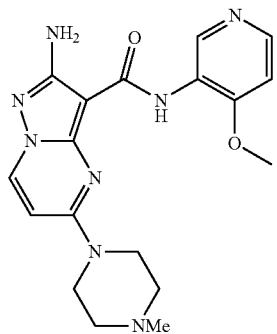
I-O-79
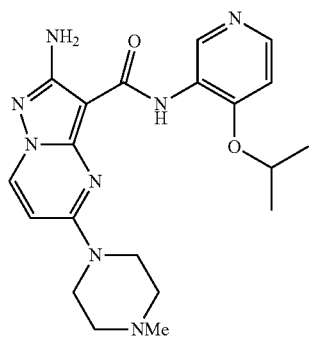
I-O-80
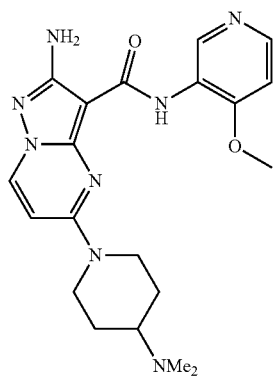
I-O-81
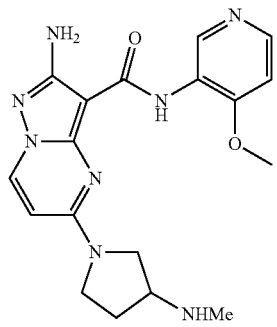
I-C-1
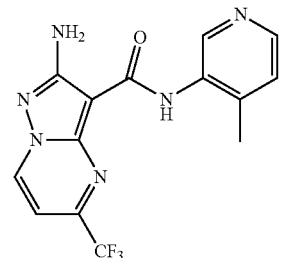
I-C-2
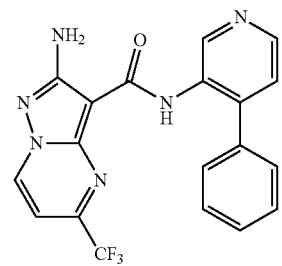

-continued

I-C-3
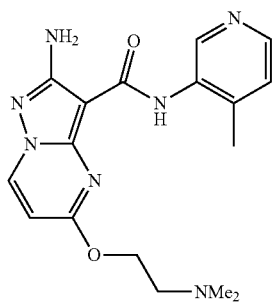

I-N-1
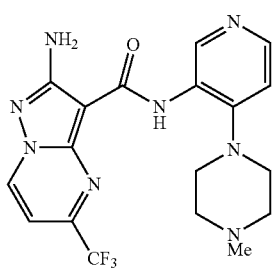

I-N-2
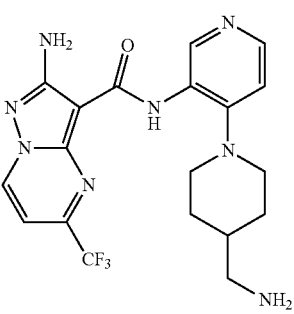

I-N-3
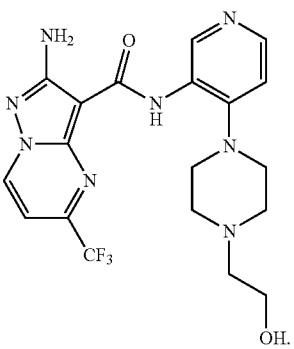

60. A pharmaceutical composition comprising a compound of any one of claim 1 or 59 and a pharmaceutically acceptable carrier.

61. A process for preparing a compound of formula I:

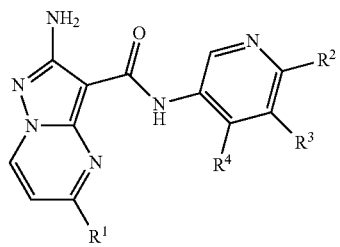

comprising reacting a compound of formula 6:

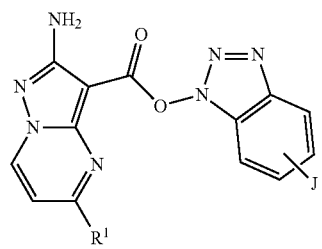

under suitable conditions to form an amide bond, wherein:
J is H or Cl; and
$R^1$, $R^2$, $R^3$ and $R^4$ are as defined in claim 1; and
the suitable conditions for forming the amide bond comprises reacting the compound of formula 6 with a substituted 3-amino pyridine in an aprotic solvent under heat.

62. The process of claim 61, further comprising the step of preparing a compound of formula 6:

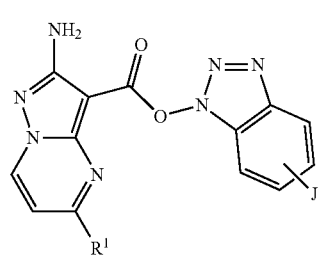

by reacting a compound of formula 5:

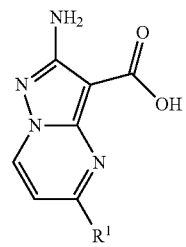

under suitable conditions to form an activated ester, wherein the suitable conditions for forming the activated ester comprises reacting the compound of formula 5 with an amide coupling agent in the presence of an organic base.

63. A process for preparing a compound of formula I:

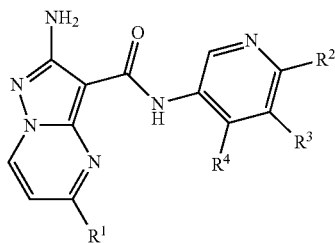

I comprising reacting a compound of formula 5:

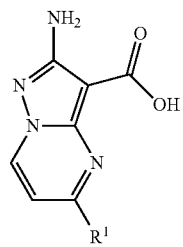

5 under suitable conditions to form an amide bond, wherein $R^1$, $R^2$, $R^3$ and $R^4$ are as defined in claim 1 and the suitable conditions for forming the amide bond comprises reacting the compound of formula 5 with a substituted 3-amino pyridine in an aprotic solvent under heat.

64. The process of any one of claims 62-63, further comprising the step of preparing a compound of formula 5:

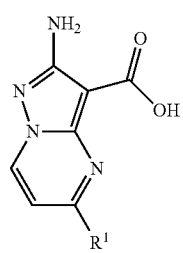

5 by reacting a compound of formula 4:

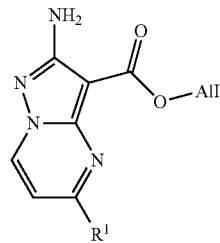

4 under suitable deprotection conditions, wherein the suitable deprotection conditions comprise reacting the compound of formula 4 with a silane in the presence of a metal catalyst.

65. The process of claim 64, further comprising the step of preparing a compound of formula 4:

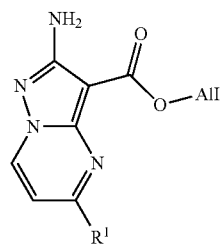

4 by reacting a compound of formula 3:

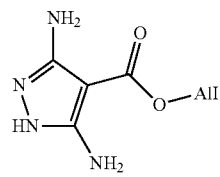

3 under suitable condensation conditions to form a pyrimidine ring, wherein the suitable condensation conditions for forming the pyrimidine ring comprises reacting a compound of formula 3 with a 1,3-dielectrophilic species in the presence of a solvent.

66. The process of claim 65, further comprising the step of preparing the compound of formula 3:

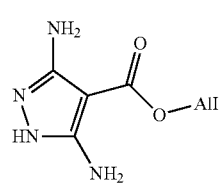

3 by reacting a compound of formula 2:

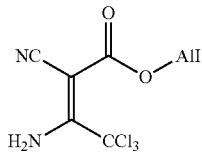

2 under suitable condensation conditions to form a pyrazole ring, wherein the suitable condensation conditions to form the pyrazole ring comprises reacting the compound of formula 2 with a hydrazine or hydrazine hydrate in the presence of an aprotic solvent under basic conditions.

67. The process of claim 66, further comprising the step of preparing a compound of formula 2:

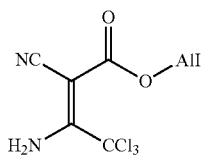

2 by reacting a compound of formula 1:

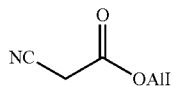

1 under suitable anion condensation conditions, wherein the suitable anion condensation conditions comprises:

1) reacting the compound of formula 1 with a base, in the presence of a solvent, to generate the anion of the compound of formula 1; and 2) reacting the anion of the compound of formula 1 with trichloroacetonitrile.

68. A process for preparing a compound of formula I:

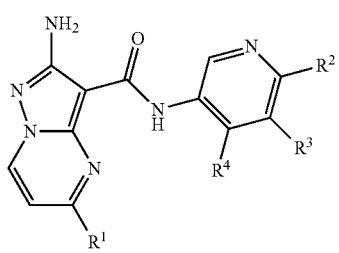

I comprising reacting a compound of formula 9:

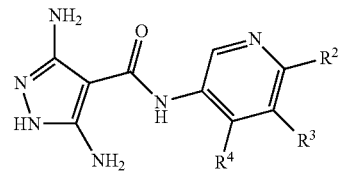

9 under suitable condensation conditions to form a pyrimidine ring, wherein $R^1$, $R^2$, $R^3$ and $R^4$ are as defined in claim 1, and the suitable condensation conditions for forming the pyrimidine ring comprises reacting the compound of formula 9 with a 1,3-dielectrophilic species in the presence of a solvent.

69. The process of claim 68, further comprising the step of preparing a compound of formula 9:

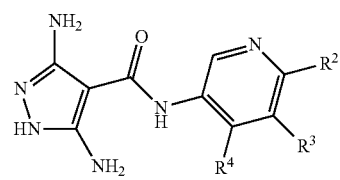

9 by reacting a compound of formula 8:

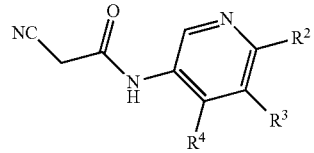

8 under suitable condensation conditions to form a pyrazole ring, wherein the suitable condensation conditions to form the pyrazole ring comprises:

1) reacting the compound of formula 8 with a base, in the presence of a solvent to generate the anion of formula 8;

2) reacting the anion with trichloroacetonitrile; and 3) reacting the product from 2) with a hydrazine or hydrazine hydrate in the presence of an aprotic solvent.

70. The process of claim 69, further comprising the step of preparing a compound of formula 8:

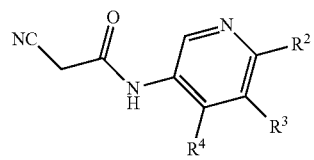

8 by reacting a compound of formula 7:
under suitable conditions to form an amide bond, wherein the suitable conditions for forming the amide bond comprises reacting the compound of formula 7 with a substituted 3-amino pyridine with an amide coupling agent in the presence of an aprotic solvent and an organic base.
* * * * *